US011834476B2

(12) United States Patent
Beernink

(10) Patent No.: US 11,834,476 B2
(45) Date of Patent: *Dec. 5, 2023

(54) FACTOR H BINDING PROTEIN VARIANTS AND METHODS OF USE THEREOF

(71) Applicant: Children's Hospital & Research Center at Oakland, Oakland, CA (US)

(72) Inventor: Peter T. Beernink, Walnut Creek, CA (US)

(73) Assignee: Children's Hospital & Research Center at Oakland, Oakland, CA (US)

( * ) Notice: Subject to any disclaimer, the term of this patent is extended or adjusted under 35 U.S.C. 154(b) by 334 days.

This patent is subject to a terminal disclaimer.

(21) Appl. No.: 17/065,386

(22) Filed: Oct. 7, 2020

(65) Prior Publication Data

US 2021/0101942 A1  Apr. 8, 2021

Related U.S. Application Data

(60) Continuation of application No. 16/600,259, filed on Oct. 11, 2019, now Pat. No. 10,836,799, which is a continuation of application No. 16/288,760, filed on Feb. 28, 2019, now Pat. No. 10,487,122, which is a division of application No. 15/327,346, filed as application No. PCT/US2015/041616 on Jul. 22, 2015, now Pat. No. 10,266,572.

(60) Provisional application No. 62/028,123, filed on Jul. 23, 2014.

(51) Int. Cl.
*A61K 39/095* (2006.01)
*C07K 14/22* (2006.01)
*A61K 39/00* (2006.01)

(52) U.S. Cl.
CPC ............ *C07K 14/22* (2013.01); *A61K 39/095* (2013.01); *A61K 2039/55505* (2013.01); *A61K 2039/575* (2013.01)

(58) Field of Classification Search
None
See application file for complete search history.

(56) References Cited

U.S. PATENT DOCUMENTS

| | | | |
|---|---|---|---|
| 7,628,995 B2 | 12/2009 | Bos et al. | |
| 8,101,194 B2 | 1/2012 | Zlotnick et al. | |
| 8,470,340 B2 | 6/2013 | Beernink et al. | |
| 8,968,748 B2 | 3/2015 | Granoff et al. | |
| 9,266,942 B2 | 2/2016 | Granoff et al. | |
| 9,827,300 B2 | 11/2017 | Beernink et al. | |
| 10,266,572 B2 | 4/2019 | Beernink et al. | |
| 10,487,122 B2* | 11/2019 | Beernink | A61K 39/095 |
| 2004/0167068 A1 | 8/2004 | Zlotnick et al. | |
| 2006/0171957 A1 | 8/2006 | Pizza et al. | |
| 2006/0251670 A1 | 11/2006 | Comanducci et al. | |
| 2006/0257413 A1 | 11/2006 | Zlotnick et al. | |
| 2007/0026021 A1 | 2/2007 | Fraser et al. | |
| 2008/0248065 A1 | 10/2008 | Granoff et al. | |
| 2009/0035328 A1 | 2/2009 | Granoff et al. | |
| 2011/0256180 A1 | 10/2011 | Beernink et al. | |
| 2011/0318378 A1 | 12/2011 | Beernink et al. | |
| 2012/0052092 A1 | 3/2012 | Exley et al. | |
| 2012/0107339 A1 | 5/2012 | Granfoff et al. | |
| 2012/0288517 A1 | 11/2012 | Beernink et al. | |
| 2013/0022633 A1 | 1/2013 | Banci et al. | |
| 2013/0149326 A1 | 6/2013 | Contorni et al. | |
| 2013/0217859 A1 | 8/2013 | Masignani et al. | |
| 2014/0294886 A1 | 10/2014 | Pizza | |

FOREIGN PATENT DOCUMENTS

| | | |
|---|---|---|
| AU | 2013206190 | 6/2013 |
| CN | 104072590 | 6/2020 |
| WO | WO 1999057280 | 11/1999 |
| WO | WO 2001052885 | 7/2001 |
| WO | WO 2003063766 | 8/2003 |
| WO | WO 2004048404 | 10/2004 |
| WO | WO 2005102384 | 11/2005 |
| WO | WO 2006024954 | 3/2006 |
| WO | WO 2006081259 | 8/2006 |
| WO | WO 2007060548 | 5/2007 |
| WO | WO 2009038889 | 3/2009 |
| WO | WO 2009104097 | 8/2009 |
| WO | WO 2009114485 | 9/2009 |
| WO | WO 2010027872 | 3/2010 |
| WO | WO 2010028096 | 3/2010 |
| WO | WO 2010028859 | 3/2010 |
| WO | WO 2010046715 | 4/2010 |
| WO | WO 2010127172 | 11/2010 |
| WO | WO 2011051893 | 5/2011 |
| WO | WO 2013006055 | 1/2013 |
| WO | WO 2013078223 | 5/2013 |
| WO | 2014030003 | 2/2014 |
| WO | 2015128480 | 9/2015 |
| WO | WO 2016008960 | 1/2016 |

OTHER PUBLICATIONS

Beernink et al. (2011) "A Meningococcal Factor H Binding Protein Mutant That Eliminates Factor H Binding Enhances Protective Antibody Responses to Vaccination" The Journal of Immunology, 186(6):3606-3614.

Beernink, P.T., et al., Abstracts of 16th International Pathogenic Neisseria Conference, Rotterdam, Netherlands, p. 194, #P126, Sep. 7-12, 2008.

Beernink et al. In: Program and Abstract Guide, 17th International Pathogenic Neisseria Conference, Banff, Alberta, Canada, p. 58, #OM42, Sep. 11-16, 2010.

Beernink, et al (2006) "Rapid Genetic Grouping of Factor h-binding Protein (Genome-Derived neisserial antigen 1870), a Promising Group B Meningococcal Vaccine Candidate", *Clin. Vaccine Immunol.* 13(7):758-763.

(Continued)

*Primary Examiner* — S. Devi
(74) *Attorney, Agent, or Firm* — Shweta Chandra; Bozicevic, Field & Francis LLP

(57) ABSTRACT

Variant factor H binding proteins that can elicit antibodies that are bactericidal for at least one strain of *Neisseria meningitidis*, compositions comprising such proteins, and methods of use of such proteins, are provided.

18 Claims, 24 Drawing Sheets

Specification includes a Sequence Listing.

(56) References Cited

OTHER PUBLICATIONS

Beernink, et al., "A Region of the N-Terminal Domain of Meningococcal Factor H-Binding Protein that Elicits Bactericidal Antibody Across Antigenic Variant Groups", Molecular Immunology, 2009, 46(8-9):1647-1653.
Beernink, et al., "Fine Antigenic Specificity and Cooperative Bactericidal Activity of Monoclonal Antibodies Directed at the Meningococcal Vaccine Candidate Factor H-Binding Protein", Infection and Immunity, 2008, 76(9):4232-4940.
Beernink, et al., "Prevalence of Factor H-Binding Protein Variants and NadA Among Meningococcal Group B Isolates from the United States: Implications for the Development of a Multicomponent Group B Vaccine", Journal of Infectious Disease, 2007, 195(10):1472-1479.
Beernink, et al., The Modular Architecture of Meningococcal Factor H-Binging Protein, Microbiology, 2009, 155:2873-2883.
Beernink, et al., Factor H Binding Protein. GenBank Direct Submission Accession ACJ45782 [online]. Nov. 23, 2009 [retrieved on Aug. 2, 2011], retrieved from the Internet:URL:http://www.ncbi.nlm.nih.gov/proteinacj45782, p. 1.
Beernink. et al., "Bactericidal Antibody Responses Induced by Meningococcal Recombinant Chimeric Factor H-Binding Protein Vaccines", Infection and Immunity, 2008, 76(6):2568-2575.
Borrow et al., "Serological Basis for Use of Meningococcal Serogroup C Conjugate Vaccines in the United Kingdom: Reevaluation of Correlates of Protection", Infect. Immun. (2001) 69(3):1568-1573.
Davila et al. (2010) "Genome-wide association study identifies variants in the CFH region associated with host susceptibility to meningococcal disease" Nat Genetics 42(9):772-776. doi:10.1038/ng.640.
De Filippis, et al., Factor H Binding Protein. Gen Bank Direct Submission Accession ACZ93150 [online]. Dec. 15, 2009 [retrieved on Aug. 2, 2011], retrieved from the internet:URL:http://www.ncbi.nlm.nih.gov/protein/acz93150,p. 1.
De Filippis, et al., Factor H Binding Protein. GenBank Direct Submission Accession ACZ93290 [online]. Dec. 15, 2009] retrieved on Aug. 2, 2011], retrieved from the Internet:URL:http://www.ncbi.nlm.nih.gov/protein/acz93290, p. 1.
Dunphy, et al., "Effect of Factor H-Binding Protein Sequence Variation on Factor H Binding and Survival of Neisseria meningitidis in Human Blood", 2011, Infection and Immunity, vol. 79, No. 1, pp. 353-359.
Fletcher, et al. (2004) "Vaccine potential of the Neisseria meningitidis 2086 lipoprotein" Infect Immun. 72(4):2088-2100.
Fukasawa, et al., Immune Response to Naitive NadA from Neisseria Meningitidis and its Expression in Clinical Isolates in Mrazil, Journal of Medical Microbiology, 2003, 52:121-125.
Genbank Accession No. AAW88802, Factor H binding protein from Neisseria Gonorrhoeae (strain ATCC 700825/FA 1090) Mar. 15, 2005.
GenBank Accession No. AY548370 "Neisseria meningitidis strain H44/76 lipoprotein (gna1870) gene, complete cds" (AAT01289.1) (from N. meningitidis strain H44/76), dated May 1, 2004.
GenBank Accession No. AY548371 "Neisseria meningitidis strain CU385 lipoprotein (gna1870) gene, complete cd" (AAT01290.1) (from N. meningitidis strain CU385), dated May 1, 2004.
GenBank Accession No. AY548372 "Neisseria meningitidis strain BZ83 lipoprotein GNA1870 (gna1870) gene, complete cd" (AAS56915.1) (from N. meningitidis strain BZ83), dated Apr. 22, 2004.
GenBank Accession No. AY548373 "Neisseria meningitidis strain 4243 lipoprotein GNA1870 (gna1870) gene, complete cd" (AAS56916.1) (from N. meningitidis strain 4243), dated Apr. 22, 2004.
GenBank Accession No. AY548374 "Neisseria meningitidis strain M6190 lipoprotein GNA1870 (gna1870) gene, complete cd" (AAS56917.1) (from N. meningitidis strain M6190), dated Apr. 22, 2004.
GenBank Accession No. AY548375 "Neisseria meningitidis strain N98/254 lipoprotein GNA1870 (gna1870) gene, complete cd" (AAS56918.1) (from N. meningitidis strain NZ98/254), dated Apr. 22, 2004.
GenBank Accession No. AY548376 "Neisseria meningitidis strain M1390 lipoprotein GNA1870 (gna1870) gene, complete cds" (AAS56919.1) (from N. meningitidis strain M1390), dated Apr. 22, 2004.
GenBank Accession No. AY548377 "Neisseria meningitidis strain M4105 lipoprotein GNA1870 (gna1870) gene, complete cd" (AAS56920.1) (fHbp ID 4 from N. meningitidis strain M4105), dated Apr. 22, 2004.
GenBank Accession No. NC_003112, "Neisseria meningitidis MC58, complete genom" GeneID: 904318 (NCBI Ref. NP_274866), fHbp ID 1 from N. meningitidis strain MC58, ), dated May 24, 2010.
GenBank Accession No. NP_000177 (P08603), and its encoding nucleic acid as NM_000186, "complement factor H isoform a precursor [Homo sapiens]" dated Mar. 21, 2010.
Giuliani, et al. (2005) "The region comprising amino acids 100 to 255 of Neisseria meningitidis lipoprotein GNA 1870 elicits bactericidal antibodies" Infect. Immun. 73(2):1151-1160.
Goldschneider, et al. (1969) "Human Immunity to the Meningococcus: I. The Role of the Humoral Antibodies" J. Exp. Med. 129(6):1307-1326.
Granoff, et al. (1998) "Bacterial Monoclonal Antibodies That Define Unique Meningococcal B Polysaccharide Epitopes That Do Not Cross-React with Human Polysialic Acid" J. Immunol. 160(10):5028-5036.
Granoff, et al. (2009) "Binding of complement factor H (fH) to Neisseria meningitidis is specific for human fH and inhibits complement activation by rat and rabbit sera" Infect. Immun. 77(2):764-769.
Huo et al. (2005) "Protective antibody responses elicited by a meningococcal outer membrane vesicle vaccine with overexpressed genome-derived neisserial antigen 1870" Journal of Infectious Diseases; 192(4):580-590.
Johnson S. et al., "Design and Evaluation of Meningococcal Vaccines through Structure-Based Modification of Host and Pathogen Molecules", PLOS Pathogens (2012) 8(10): e1002981.
Konar et al. (2015) "A Mutant Library Approach to Identify Improved Meningococcal Factor H Binding Protein Vaccine Antigens" PLoS One. 10(6):e0128185.
Lazar et al. (1988) "Transforming Growth Factor alpha: Mutation of Aspartic Acid 47 and Leucine 48 Results in Different Biological Activities" Cellular Biol. 8(3):1247-1252.
Lewis, et al., The Meningococcal Vaccine Candidate Neisserial Surface Protein A (NspA) Binds to Factor H and Enhances Meningococcal Resistance to Complement, PLOS Pathogens, 2010, 6(7):1-20.
Madico, et al., "The Meningococcal Vaccine Candidate GNA1870 Binds the Complement Regulatory Protein Factor H and Enhances Serum Resistance", 2006, The Journal of Immunology, 177:501-510.
Madico, et al., Factor H Binding Protein. GenBank Direct Submission Accession ABC59063 [online], Jun. 20, 2006 [retrieved on Aug. 2, 2011], retrieved from the Internet:URL:http://www.ncbi.nlm.nih.gov/protein/abc59063, p. 1.
Mascioni et al. (2009) "Structural Basis for the Immunogenic Properties of the Meningococcal Vaccine Candidate LP2086" Journal of Bio. Chem.; 284(13):8738-8746.
Masignani, et al., "Vaccination against Neisseria meningitides Using Three Variants of the Lipoprotein GNA1879," Journal Exp. Med., 2003, 197(6):789-799.
Maslanka, et al., "Standardization and a Multilaboratory Comparison of Neisseria Meningitidis Serogroup A and C Serum Bactericidal Assays", Clinical Diagnostic Laboratory Immunology, 1997, 4(2):156-157.
McDowell, et al., "Demonstration of the Involvement of Outer Surface Protein E Coiled Coil Structure and Higher Order Structural Elements in the Binding of Infection-Induced Antibody and the Complement-Regulatory Protein, Factor H", Journal of Immunology, 2004, vol. 173, pp. 7471-7480.
Morrison, K.L., et al., "Combination alanine-scanning," Curr. Opin. Chem. Biol. (2001) 5:302.307.

(56) References Cited

OTHER PUBLICATIONS

Murphy, et al., Factor H Binding Protein Variant A72_001. GenBank Direct Submission Accession ACI46937 [online]. Aug. 4, 2009 [retrieved from the internet]:URL:http://www.ncbi.nim.nih.gov/protein/aci46937, p. 1.
Murphy, et al., "Sequence Diversity of the Factor H Binding Protein Vaccine Candidate in Epidemiologically Relevant Strains of Serogroup B Neisseria meningitidis", The Journal of Infectious Diseases, 2009, pp. 379-389.

Ngampasutadol et al., "A Novel Interaction Between Factor H SCR 6 and the Meningococcal Vaccine Candidate GNA 1870: Implications for Meningococcal Pathogenesis and Vaccine Development", Molecular Immunology, 2007, 44(1-3):220.

Ngampasutadol et al., "Human Factor H Interacts Selectively with Neisseria Gonorrhoeae and Results in Species-Specific Complement Evasion", The Journal of Immunology, 2008, 180(5):3426-3435.
Pajon, et al. "Design of meningococcal factor H binding protein mutant vaccines that do not bind human complement factor H", Infect Immun. (2012) 80(8):2667-77.
Pajon, et al. (2010) "Frequency of factor H-binding protein modular groups and susceptibility to cross-reactive bactericidal activity in invasive meningococcal isolates" *Vaccine* 28(9):2122-2129.
Scarselli, et al. (2009) "Epitope mapping of a bactericidal monoclonal antibody against the factor H binding protein of Neisseria meningitidis" *J. Mol. Biol*. 386(1):97-108.
Schneider, et al. "Supplemental Methods for Neisseria Meningitides Recruits Factor H Using Protein Mimicry of Host Carbohydrates", Nature, 2009, 1-17.
Schneider, et al. "Neisseria Meningitides Recruits Factor H Using Protein Mimicry of Host Carbohydrates", Nature, 2009, 458:890-895.
Seib, et al., "Characterization of Diverse Subvariants of the Meningococcal Factor H (fH) Binding Protein for Their Ability to Bind fH, to Mediate Serum Resistance, and to Induce Bactericidal Antibodies", 2011, Infection and Immunity, vol. 79, No. 2, pp. 970-981.
Shaughnessy, et al. (2009) "Functional comparison of the binding of factor H short consensus repeat 6 (SCR 6) to factor H binding protein from Neisseria meningitidis and the binding of factor H SCR 18 to 20 to Neisseria gonorrhoeae porin" *Infect. Immun*. 77(5):2094-2103.
Skolnick et al. (2000) "From genes to protein structure and function: novel applications of computational approaches in the genomic era" Trends in Biotechnology. 18:34-39.
Tettelin, et al., Uniprot Q9JXV4 [online] Oct. 1, 2000 [retrieved on Aug. 2, 2011], retrieved from the internet: URL:http://www.uniprot.org/uniprot/Q9JXV4.txt, p. 1.
Vu et al., "A Broadly Cross-Reactive Monoclonal Antibody Against an Epitope on the N-terminus of Meningococcal fHbp",Scientic Reports (2012) 2(341):1-8.
Welsch, et al., Complement-Dependent Synergistic Bactericidal Activity of Antibodies Against Factor H-Binding Protein, a Sparsely Distributed Meningococcal Vaccine Antigen, The Journal of Infectious Disease, 2008, 197:1053-61.
Welsch, et al., "Protective Activity of Monoclonal Antibodies to Genome-Derived Neisserial Antigen 1870, a Neisseria Meningitidis Candidate Vaccine", Journal of Immunology, 2004, 172:5606-5615.
Welsch, et al., Lipoprotein GNA1870. GenBank Direct Submission Accession AAS56918 [online], Apr. 22, 2004 [retrieved on Aug. 2, 2011], retrieved from the Internet:<URL:http://www.ncbi.nlm.nih.gov/protein/AAS56918, p. 1.
(2012) "Factor H binding protein, partial [Neisseria meningitidis]." NCBI, GenBank Accession No. AGA84494.1, Case No. 729206, retrieved from https://www.ncbi.nlm.nih.gov/protein/AGA84494.1/, 5 pages.

* cited by examiner

FIG. 17

| Residue in ID 1 | Position[a] | Residue in library mutant | Residue conserved across variant groups | Alternative residue(s) in other variant groups | Hydrogen bond with FH | Position reported as contact residue[b] | Fold-change for Ala mutant[c,d] |
|---|---|---|---|---|---|---|---|
| Q | 38 | R | No | D | Yes | Yes [b] | n/d |
| E | 92 | K | No | A | No | No | n/d |
| R | 130 | G | No | L | Yes | Yes [c] | 90.6 |
| S | 223 | R | No | H | No | No | 1.2 |
| H | 248 | L | No | E | No | No | 9.6 |
| | | | | | | | |
| Residue in ID 22 | Position[a] | Residue in library mutant | Residue conserved across variant groups | Alternative residue(s) in other variant groups[e] | Hydrogen bond with FH | Position reported as contact residue[b] | Fold-change for Ala mutant[c,d] |
| N | 115 | I | No | Q | Yes | Yes | n/d |
| D | 121 | G | No | G | No | No | n/d |
| S | 128 | T | No | Q, R | Yes | Yes | >100 |
| V | 131 | D | No | I | No | No | 11.5 |
| K | 219 | N | Yes | n/a | No | No | n/d |
| G | 220 | S | Yes | n/a | No | No | n/d |

[a] Position is according to mature FHbp ID1 sequence, with the lapidated cysteine as position 1.
[b] Position reported as contact residue by Schneider et al. (Nature 2009;458:890-3)
[c] Position tested as alanine mutant for FH binding by Johnson et al. (PLoS Pathog 2012;8:e1002981)
[d] n/d, not done
[e] n/a, not applicable

Fig. 18

Human factor H

```
MRLLAKIICLMLWAICVAEDCNELPPRRNTEILTGSWSDQTYPEGTQAIYKCRPGYRSLG     60
NVIMVCRKGEWVALNPLRKCQKRPCGHPGDTPFGTFTLTGGNVFEYGVKAVYTCNEGYQL    120
LGEINYRECDTDGWTNDIPICEVVKCLPVTAPENGKIVSSAMEPDREYHFGQAVRFVCNS    180
GYKIEGDEEMHCSDDGFWSKEKPKCVEISCKSPDVINGSPISQKIIYKENERFQYKCNMG    240
YEYSERGDAVCTESGWRPLPSCEEKSCDNPYIPNGDYSPLRIKHRTGDEITYQCRNGFYP    300
ATRGNTAKCTSTGWIPAPRCTLKPCDYPDIKHGGLYHENMRRPYFPVAVGKYYSYYCDEH    360
FETPSGSYWDHIHCTQDGWSPAVPCLRKCYFPYLENGYNQNYGRKFVQGKSIDVACHPGY    420
ALPKAQTTVTCMENGWSPTPRCIRVKTCSKSSIDIENGFISESQYTYALKEKAKYQCKLG    480
YVTADGETSGSITCGKDGWSAQPTCIKSCDIPVFMNARTKNDFTWFKLNDTLDYECHDGY    540
ESNTGSTTGSIVCGYNGWSDLPICYERECELPKIDVHLVPDRKKDQYKVGEVLKFSCKPG    600
FTIVGPNSVQCYHFGLSPDLPICKEQVQSCGPPPELLNGNVKEKTKEEYGHSEVVEYYCN    660
PRFLMKGPNKIQCVDGEWTTLPVCIVEESTCGDIPELEHGWAQLSSPPYYYGDSVEFNCS    720
ESFTMIGHRSITCIHGVWTQLPQCVAIDKLKKCKSSNLIILEEHLKNKKEFDHNSNIRYR    780
CRGKEGWIHTVCINGRWDPEVNCSMAQIQLCPPPPQIPNSHNMTTTLNYRDGEKVSVLCQ    840
ENYLIQEGEEITCKDGRWQSIPLCVEKIPCSQPPQIEHGTINSSRSSQESYAHGTKLSYT    900
CEGGFRISEENETTCYMGKWSSPPQCEGLPCKSPPEISHGVVAHMSDSYQYGEEVTYKCF    960
EGFGIDGPAIAKCLGEKWSHPPSCIKTDCLSLPSFENAIPMGEKKDVYKAGEQVTYTCAT   1020
YYKMDGASNVTCINSRWTGRPTCRDTSCVNPPTVQNAYIVSRQMSKYPSGERVRYQCRSP   1080
YEMFGDEEVMCLNGNWTEPPQCKDSTGKCGPPPPIDNGDITSFPLSVYAPASSVEYQCQN   1140
LYQLEGNKRITCRNGQWSEPPKCLHPCVISREIMENYNIALRWTAKQKLYSRTGESVEFV   1200
CKRGYRLSSRSHTLRTTCWDGKLEYPTCAKR   1231   (SEQ ID NO:4)
```

Fig. 19

```
            1         10        20        30        40        50
            |         |         |         |         |         |
ID_1        CS------SGGGGVAADIGAGLADALTAPLDHKDKGLQSLTLD SVRKNEKLKLAAQGAEK   55
ID_22       CS------SGGGGVAADIGAGLADALTAPLDHKDKSLQSLTLDQSVRKNEKLKLAAQGAEK   55
ID_55       CSSGGGGSGGGGVTADIGTGLADALTAPLDHKDKGLKSLTLEDSISQNGTLTLSAQGAEK    60

60        70        80        90       100       110
            |         |         |         |         |         |
ID_1        TYGNGDSLNTGKLKNDKVSRFDFIRQIEVDGQLITL SGEFQVYKQSHSALTAFQTEQIQ    115
ID_22       TYGNGDSLNTGKLKNDKVSRFDFIRQIEVDGQLITLESGEFQIYKQDHSAVVALQIEKI     115
ID_55       TYGNGDSLNTGKLKNDKVSRFDFIRQIEVDGQLITL SGEFQVYKQSHSALTALQTEQEQ    120

120       130       140       150       160       170
            |         |         |         |         |         |
ID_1        DSEHSGKMVAKRQF IGDIAGEHTSFDKLPEGGRATYRGTAFGSDDAGGKLTYTIDFAAK   175
ID_22       NPDKI SLINQR FL SGLGGEHTAFNQLPSG-KAEYHGKAFSSDDPNGRLHYSIDFTKK    174
ID_55       DPEHSEKMVAKRRFRIGDIAGEHTSFDKLPKDVMATYRGTAFGSDDAGGKLTYTIDFAAK    180

180       190       200       210       220       230
            |         |         |         |         |         |
ID_1        QGNGKIEHLKSPELNVDLAAADIKPDGKRHAVISGSVLYNQAEKGSY LGIFGGKAQEVA    235
ID_22       QGYGRIEHLKTPEQNVELASAELKADEKSHAVILGDTRYGGEE TYHLALFGDRAQEIA    234
ID_55       QGHGKIEHLKSPELNVDLAVAYIKPDEKHHAVISGSVLYNQDEKGSY LGIFGEKAQEVA    240

240       250
            |         |
ID_1        GSAEVKIVNGIR IGLAAKQ  255  (SEQ ID NO:1)
ID_22       GSATVKIREKVHEIGIAGKQ  254  (SEQ ID NO:2)
ID_55       GSAEVETANGIH IGLAAKQ  260  (SEQ ID NO:3)
```

Fig. 20
fHbp ID1 Q38R variant

CSSGGGGVAADIGAGLADALTAPLDHKDKGLQSLTLDRSVRKNEKLKLAAQGA
EKTYGNGDSLNTGKLKNDKVSRFDFIRQIEVDGQLITLESGEFQVYKQSHSALTA
FQTEQIQDSEHSGKMVAKRQFRIGDIAGEHTSFDKLPEGGRATYRGTAFGSDDA
GGKLTYTIDFAAKQGNGKIEHLKSPELNVDLAAADIKPDGKRHAVISGSVLYNQ
AEKGSYSLGIFGGKAQEVAGSAEVKTVNGIRHIGLAAKQ (SEQ ID NO:5)

Fig. 21
fHbp ID1 E92K variant

CSSGGGGVAADIGAGLADALTAPLDHKDKGLQSLTLDQSVRKNEKLKLAAQGA
EKTYGNGDSLNTGKLKNDKVSRFDFIRQIEVDGQLITLKSGEFQVYKQSHSALTA
FQTEQIQDSEHSGKMVAKRQFRIGDIAGEHTSFDKLPEGGRATYRGTAFGSDDA
GGKLTYTIDFAAKQGNGKIEHLKSPELNVDLAAADIKPDGKRHAVISGSVLYNQ
AEKGSYSLGIFGGKAQEVAGSAEVKTVNGIRHIGLAAKQ (SEQ ID NO:6)

Fig. 22
fHbp ID1 R130G variant

CSSGGGGVAADIGAGLADALTAPLDHKDKGLQSLTLDQSVRKNEKLKLAAQGA
EKTYGNGDSLNTGKLKNDKVSRFDFIRQIEVDGQLITLESGEFQVYKQSHSALTA
FQTEQIQDSEHSGKMVAKRQFGIGDIAGEHTSFDKLPEGGRATYRGTAFGSDDA
GGKLTYTIDFAAKQGNGKIEHLKSPELNVDLAAADIKPDGKRHAVISGSVLYNQ
AEKGSYSLGIFGGKAQEVAGSAEVKTVNGIRHIGLAAKQ (SEQ ID NO:7)

Fig. 23
fHbp ID1 S223R variant

CSSGGGGVAADIGAGLADALTAPLDHKDKGLQSLTLDQSVRKNEKLKLAAQGA
EKTYGNGDSLNTGKLKNDKVSRFDFIRQIEVDGQLITLESGEFQVYKQSHSALTA
FQTEQIQDSEHSGKMVAKRQFRIGDIAGEHTSFDKLPEGGRATYRGTAFGSDDA
GGKLTYTIDFAAKQGNGKIEHLKSPELNVDLAAADIKPDGKRHAVISGSVLYNQ
AEKGSYRLGIFGGKAQEVAGSAEVKTVNGIRHIGLAAKQ (SEQ ID NO:8)

Fig. 24
fHbp ID1 H248L variant

CSSGGGGVAADIGAGLADALTAPLDHKDKGLQSLTLDQSVRKNEKLKLAAQGA
EKTYGNGDSLNTGKLKNDKVSRFDFIRQIEVDGQLITLESGEFQVYKQSHSALTA
FQTEQIQDSEHSGKMVAKRQFRIGDIAGEHTSFDKLPEGGRATYRGTAFGSDDA
GGKLTYTIDFAAKQGNGKIEHLKSPELNVDLAAADIKPDGKRHAVISGSVLYNQ
AEKGSYSLGIFGGKAQEVAGSAEVKTVNGIRLIGLAAKQ (SEQ ID NO:9)

Fig. 25
fHbp ID22 N115I variant

CSSGGGGVAADIGAGLADALTAPLDHKDKSLQSLTLDQSVRKNEKLKLAAQGA
EKTYGNGDSLNTGKLKNDKVSRFDFIRQIEVDGQLITLESGEFQIYKQDHSAVVA
LQIEKI<u>I</u>NPDKIDSLINQRSFLVSGLGGEHTAFNQLPSGKAEYHGKAFSSDDPNGR
LHYSIDFTKKQGYGRIEHLKTPEQNVELASAELKADEKSHAVILGDTRYGGEEKG
TYHLALFGDRAQEIAGSATVKIREKVHEIGIAGKQ (SEQ ID NO:10)

Fig. 26
fHbp ID22 D121G variant

CSSGGGGVAADIGAGLADALTAPLDHKDKSLQSLTLDQSVRKNEKLKLAAQGA
EKTYGNGDSLNTGKLKNDKVSRFDFIRQIEVDGQLITLESGEFQIYKQDHSAVVA
LQIEKINNPDKI<u>G</u>SLINQRSFLVSGLGGEHTAFNQLPSGKAEYHGKAFSSDDPNGR
LHYSIDFTKKQGYGRIEHLKTPEQNVELASAELKADEKSHAVILGDTRYGGEEKG
TYHLALFGDRAQEIAGSATVKIREKVHEIGIAGKQ (SEQ ID NO:11)

Fig. 27
fHbp ID22 S128T variant

CSSGGGGVAADIGAGLADALTAPLDHKDKSLQSLTLDQSVRKNEKLKLAAQGA
EKTYGNGDSLNTGKLKNDKVSRFDFIRQIEVDGQLITLESGEFQIYKQDHSAVVA
LQIEKINNPDKIDSLINQR<u>T</u>FLVSGLGGEHTAFNQLPSGKAEYHGKAFSSDDPNGR
LHYSIDFTKKQGYGRIEHLKTPEQNVELASAELKADEKSHAVILGDTRYGGEEKG
TYHLALFGDRAQEIAGSATVKIREKVHEIGIAGKQ (SEQ ID NO:12)

Fig. 28
fHbp ID22 V131D variant

CSSGGGGVAADIGAGLADALTAPLDHKDKSLQSLTLDQSVRKNEKLKLAAQGA
EKTYGNGDSLNTGKLKNDKVSRFDFIRQIEVDGQLITLESGEFQIYKQDHSAVVA
LQIEKINNPDKIDSLINQRSFL<u>D</u>SGLGGEHTAFNQLPSGKAEYHGKAFSSDDPNGR
LHYSIDFTKKQGYGRIEHLKTPEQNVELASAELKADEKSHAVILGDTRYGGEEKG
TYHLALFGDRAQEIAGSATVKIREKVHEIGIAGKQ (SEQ ID NO:13)

Fig. 29
fHbp ID22 K219N variant

CSSGGGGVAADIGAGLADALTAPLDHKDKSLQSLTLDQSVRKNEKLKLAAQGA
EKTYGNGDSLNTGKLKNDKVSRFDFIRQIEVDGQLITLESGEFQIYKQDHSAVVA
LQIEKINNPDKIDSLINQRSFLVSGLGGEHTAFNQLPSGKAEYHGKAFSSDDPNGR
LHYSIDFTKKQGYGRIEHLKTPEQNVELASAELKADEKSHAVILGDTRYGGEE<u>N</u>G
TYHLALFGDRAQEIAGSATVKIREKVHEIGIAGKQ (SEQ ID NO:14)

Fig. 30
fHbp ID22 G220S variant

CSSGGGGVAADIGAGLADALTAPLDHKDKSLQSLTLDQSVRKNEKLKLAAQGA
EKTYGNGDSLNTGKLKNDKVSRFDFIRQIEVDGQLITLESGEFQIYKQDHSAVVA
LQIEKINNPDKIDSLINQRSFLVSGLGGEHTAFNQLPSGKAEYHGKAFSSDDPNGR
LHYSIDFTKKQGYGRIEHLKTPEQNVELASAELKADEKSHAVILGDTRYGGEEKS
TYHLALFGDRAQEIAGSATVKIREKVHEIGIAGKQ (SEQ ID NO:15)

Fig. 31
fHbp ID55 E92K variant

CSSGGGGSGGGGVTADIGTGLADALTAPLDHKDKGLKSLTLEDSISQNGTLTLSA
QGAEKTYGNGDSLNTGKLKNDKVSRFDFIRQIEVDGQLITLKSGEFQVYKQSHS
ALTALQTEQEQDPEHSEKMVAKRRFRIGDIAGEHTSFDKLPKDVMATYRGTAFG
SDDAGGKLTYTIDFAAKQGHGKIEHLKSPELNVDLAVAYIKPDEKHHAVISGSVL
YNQDEKGSYSLGIFGEKAQEVAGSAEVETANGIHHIGLAAKQ (SEQ ID NO:16)

Fig. 32
fHbp ID55 S223R variant

CSSGGGGSGGGGVTADIGTGLADALTAPLDHKDKGLKSLTLEDSISQNGTLTLSA
QGAEKTYGNGDSLNTGKLKNDKVSRFDFIRQIEVDGQLITLESGEFQVYKQSHSA
LTALQTEQEQDPEHSEKMVAKRRFRIGDIAGEHTSFDKLPKDVMATYRGTAFGS
DDAGGKLTYTIDFAAKQGHGKIEHLKSPELNVDLAVAYIKPDEKHHAVISGSVL
YNQDEKGSYRLGIFGEKAQEVAGSAEVETANGIHHIGLAAKQ (SEQ ID NO:17)

Fig. 33
fHbp ID55 H248L variant

CSSGGGGSGGGGVTADIGTGLADALTAPLDHKDKGLKSLTLEDSISQNGTLTLSA
QGAEKTYGNGDSLNTGKLKNDKVSRFDFIRQIEVDGQLITLESGEFQVYKQSHSA
LTALQTEQEQDPEHSEKMVAKRRFRIGDIAGEHTSFDKLPKDVMATYRGTAFGS
DDAGGKLTYTIDFAAKQGHGKIEHLKSPELNVDLAVAYIKPDEKHHAVISGSVL
YNQDEKGSYSLGIFGEKAQEVAGSAEVETANGIHLIGLAAKQ (SEQ ID NO:18)

Fig. 34
fHbp ID1 R41S/S223R variant

CSSGGGGVAADIGAGLADALTAPLDHKDKGLQSLTLDQSVSKNEKLKLAAQGA
EKTYGNGDSLNTGKLKNDKVSRFDFIRQIEVDGQLITLESGEFQVYKQSHSALTA
FQTEQIQDSEHSGKMVAKRQFRIGDIAGEHTSFDKLPEGGRATYRGTAFGSDDA
GGKLTYTIDFAAKQGNGKIEHLKSPELNVDLAAADIKPDGKRHAVISGSVLYNQ
AEKGSYRLGIFGGKAQEVAGSAEVKTVNGIRHIGLAAKQ (SEQ ID NO:19)

Fig. 35
fHbp ID1 R41S/H248L variant

CSSGGGGVAADIGAGLADALTAPLDHKDKGLQSLTLDQSVSKNEKLKLAAQGA
EKTYGNGDSLNTGKLKNDKVSRFDFIRQIEVDGQLITLESGEFQVYKQSHSALTA
FQTEQIQDSEHSGKMVAKRQFRIGDIAGEHTSFDKLPEGGRATYRGTAFGSDDA
GGKLTYTIDFAAKQGNGKIEHLKSPELNVDLAAADIKPDGKRHAVISGSVLYNQ
AEKGSYSLGIFGGKAQEVAGSAEVKTVNGIRLIGLAAKQ (SEQ ID NO:20)

Fig. 36
fHbp ID 1 S223R/H248L variant

CSSGGGGVAADIGAGLADALTAPLDHKDKGLQSLTLDQSVRKNEKLKLAAQGA
EKTYGNGDSLNTGKLKNDKVSRFDFIRQIEVDGQLITLESGEFQVYKQSHSALTA
FQTEQIQDSEHSGKMVAKRQFRIGDIAGEHTSFDKLPEGGRATYRGTAFGSDDA
GGKLTYTIDFAAKQGNGKIEHLKSPELNVDLAAADIKPDGKRHAVISGSVLYNQ
AEKGSYRLGIFGGKAQEVAGSAEVKTVNGIRLIGLAAKQ (SEQ ID NO:21)

Fig. 37
fHbp ID22 L130R/G133D (stability double mutant "DM") variant

CSSGGGGVAADIGAGLADALTAPLDHKDKSLQSLTLDQSVRKNEKLKLAAQGA
EKTYGNGDSLNTGKLKNDKVSRFDFIRQIEVDGQLITLESGEFQIYKQDHSAVVA
LQIEKINNPDKIDSLINQRSFRVSDLGGEHTAFNQLPSGKAEYHGKAFSSDDPNGR
LHYSIDFTKKQGYGRIEHLKTPEQNVELASAELKADEKSHAVILGDTRYGGEEKG
TYHLALFGDRAQEIAGSATVKIREKVHEIGIAGKQ (SEQ ID NO:22)

Fig. 38
fHbp ID22 L130R/G133D/K219N (DM-K219N) variant

CSSGGGGVAADIGAGLADALTAPLDHKDKSLQSLTLDQSVRKNEKLKLAAQGA
EKTYGNGDSLNTGKLKNDKVSRFDFIRQIEVDGQLITLESGEFQIYKQDHSAVVA
LQIEKINNPDKIDSLINQRSFRVSDLGGEHTAFNQLPSGKAEYHGKAFSSDDPNGR
LHYSIDFTKKQGYGRIEHLKTPEQNVELASAELKADEKSHAVILGDTRYGGEENG
TYHLALFGDRAQEIAGSATVKIREKVHEIGIAGKQ (SEQ ID NO:23)

Fig. 39
fHbp ID22 L130R/G133D/G220S (DM-G220S) variant

CSSGGGGVAADIGAGLADALTAPLDHKDKSLQSLTLDQSVRKNEKLKLAAQGA
EKTYGNGDSLNTGKLKNDKVSRFDFIRQIEVDGQLITLESGEFQIYKQDHSAVVA
LQIEKINNPDKIDSLINQRSFRVSDLGGEHTAFNQLPSGKAEYHGKAFSSDDPNGR
LHYSIDFTKKQGYGRIEHLKTPEQNVELASAELKADEKSHAVILGDTRYGGEEKS
TYHLALFGDRAQEIAGSATVKIREKVHEIGIAGKQ (SEQ ID NO:24)

Fig. 40

NspA

GenBank Accession No. AAD53286

```
  1 mkkalatlia lalpaaalae gasgfyvqad aahakasssl gsakgfspri sagyrindlr
 61 favdytrykn ykapstdfkl ysigasaiyd fdtqspvkpy lgarlslnra svdlggsdsf
121 sqtsiglgvl tgvsyavtpn vdldagyryn yigkvntvkn vrsgelsvgv rvkf
(SEQ ID NO:25)
```

US 11,834,476 B2

FACTOR H BINDING PROTEIN VARIANTS AND METHODS OF USE THEREOF

CROSS-REFERENCE

This application is a continuation of U.S. application Ser. No. 16/600,259 filed on Oct. 11, 2019, now U.S. Pat. No. 10,836,799; which is a continuation of U.S. application Ser. No. 16/288,760 filed on Feb. 28, 2019, now U.S. Pat. No. 10,487,122; which is a divisional of U.S. application Ser. No. 15/327,346 filed Jan. 18, 2017, now U.S. Pat. No. 10,266,572; which is a national phase of PCT/US2015/041616 filed on Jul. 22, 2015; which claims the benefit of U.S. Provisional Patent Application No. 62/028,123, filed Jul. 23, 2014, which application is incorporated herein by reference in its entirety.

STATEMENT OF GOVERNMENT SUPPORT

This invention was made with government support under grant number R01 AI99125 awarded by the National Institutes of Health. The government has certain rights in the invention.

INTRODUCTION

*Neisseria meningitidis* is a Gram-negative bacterium that colonizes the human upper respiratory tract and is responsible for worldwide sporadic and cyclical epidemic outbreaks of, most notably, meningitis and sepsis. The attack and morbidity rates are highest in children under 2 years of age. Like other Gram-negative bacteria, *Neisseria meningitidis* typically possess a cytoplasmic membrane, a peptidoglycan layer, an outer membrane, which together with the capsular polysaccharide constitute the bacterial wall, and pili, which project into the outside environment. Encapsulated strains of *Neisseria meningitidis* are a major cause of bacterial meningitis and septicemia in children and young adults. The prevalence and economic importance of invasive *Neisseria meningitidis* infections have driven the search for effective vaccines that can confer immunity across different strains, and particularly across genetically diverse serogroup B strains with different serotypes or serosubtypes.

Factor H Binding Protein (fHbp, also referred to in the art as lipoprotein 2086 (Fletcher et al (2004) *Infect Immun* 72:2088-2100), Genome-derived Neisserial antigen (GNA) 1870 (Masignani et al. (2003) *J Exp Med* 197:789-99) or "741") is an *N. meningitidis* protein that is expressed in the bacterium as a surface-exposed lipoprotein. An important function of fHbp is to bind human complement factor H (fH), which down-regulates complement activation. Binding of fH to the bacterial surface is an important mechanism by which the pathogen survives in non-immune human serum or blood and evades innate host defenses. Recently, genetic variation in the human factor H gene cluster was found to affect susceptibility to developing meningococcal disease (Davila S et al. (2010) Nat Genetics doi:10.1038/ng.640). Binding of fH to fHbp is specific for human fH, and several non-human primates and could partially explain why *Neisseria meningitidis* is strictly a human pathogen. fHbp occurs in many natural sequence variants that are designated by identification (ID) numbers as assigned in the fHbp database on the internet at pubmlst(dot)org/neisseria/fHbp.

There remains a need for an fHbp polypeptide that can elicit effective bactericidal antibody responses.

SUMMARY

Variant factor H binding proteins that can elicit antibodies that are bactericidal for at least one strain of *Neisseria meningitidis*, compositions comprising such proteins, and methods of use of such proteins, are provided.

FEATURES

The present disclosure provides variants of factor H binding protein (fHbp) ID 1. The present disclosure provides a variant of fHbp wherein the variant comprises an amino acid substitution selected from at least one of: a) an amino acid substitution of the glutamine at amino acid 38 (Q38); b) an amino acid substitution of the glutamic acid at amino acid 92 (E92); c) a substitution of glycine for arginine at amino acid 130 (R130G); d) an amino acid substitution of the serine at amino acid 223 (S223); and e) a substitution of histidine for leucine at amino acid 248 (H248L), wherein the amino acid substitutions are relative to fHbp ID 1 (SEQ ID NO:1), wherein the variant comprises an amino acid sequence having at least 80% amino acid sequence identity to SEQ ID NO:1, wherein the variant fHbp binds human factor H (fH) with an affinity that is 50% or less of the affinity of fHbp ID 1 for human fH, and wherein the variant induces a bactericidal antibody response to at least one strain of *Neisseria meningitidis* in a mammalian host. In some cases, the amino acid substitution at Q38 is Q38R, Q38K, Q38H, Q38F, Q38Y, or Q38W. In some cases, the amino acid substitution at E92 is E92K, E92R, E92H, E92F, E92Y, or E92W. In some cases, the amino acid substitution at S223 is S223R, S223K, S223H, S223F, S223Y, or S223W. In some cases, the variant fHbp may further include a R41S or a R41A substitution relative to fHbp ID 1. For example the variant fHbp may include a R41S or a R41A substitution and a substitution at S223, e.g., R41S/S223R, relative to fHbp ID 1. In other cases, the variant fHbp may further include a R41S or a R41A substitution and a H248L substitution relative to fHbp ID 1. In certain cases, the variant fHbp may include two, three, or more of the substitutions disclosed herein. In a specific example, the variant fHbp may include the following substitutions: S223R and H248L relative to fHbp ID 1. In some cases, the variant fHbp binds human fH with an affinity that is 25% or less of the affinity of the fHbp ID 1 for human fH. In some cases, the variant fHbp binds human fH with an affinity that is 10% or less of the affinity of the fHbp ID 1 for human fH. In some cases, the variant fHbp binds human fH with an affinity that is 5% or less of the affinity of the fHbp ID 1 for human fH.

The present disclosure provides variants of fHbp ID 22. The present disclosure provides a variant of fHbp, wherein the variant comprises at least one amino acid substitution selected from: a) a substitution of isoleucine for asparagine at amino acid 115 (N115I); b) a substitution of glycine for aspartic acid at amino acid 121 (D121G); c) a substitution of threonine for serine at amino acid 128 (S128T); d) an amino acid substitution of the valine at position 131 (V131); e) an amino acid substitution of the lysine at position 219 (K219); f) an amino acid substitution of the glycine at position 220 (G220), wherein the amino acid substitutions are relative to fHbp ID 22 (SEQ ID NO:2), wherein the variant comprises an amino acid sequence having greater than 85% amino acid sequence identity to SEQ ID NO:2, wherein the variant fHbp binds human factor H (fH) with an affinity that is 50% or less of the affinity of fHbp ID 22 for human fH, and wherein the variant induces a bactericidal antibody response in a mammalian host. In some cases, the variant fHbp binds human fH with an affinity that is 25% or less of the affinity of the fHbp ID 22 for human fH. In some cases, the variant fHbp binds human fH with an affinity that is 10% or less of the affinity of the fHbp ID 22 for human fH. In some cases, the variant fHbp binds human fH with an affinity that is 5% or less of the affinity of the fHbp ID 22 for human fH. In some cases, the amino acid substitution at V131 is V131D, V131E, V131K, V131R, V131F, V131H, V131Y, or V131W. In some cases, the amino acid substitution at K219 is K219N, K219Q, K219D, K219E, K219F, K219Y, or K219W. In some cases, the amino acid substitution at G220 is G220S, G220N, G220Q, G220D, G220E, G220K, G220R, G220H, G220F, G220Y, or G220W.

In some cases, the variant fHbp includes a double mutation that increases thermal stability of the variant fHbp compared to thermal stability of wild type (WT) fHbp, e.g., WT fHbp ID 22. In some cases, the variant fHbp may include the substitutions L130R and G133D relative to fHbp ID 22 (SEQ ID NO:2), wherein the variant fHbp comprises an amino acid sequence having greater than 85% amino acid sequence identity to SEQ ID NO:2, wherein the variant fHbp binds human factor H (fH) with an affinity that is 50% or less of the affinity of fHbp ID 22 for human fH, wherein the variant induces a bactericidal antibody response in a mammalian host, and wherein the variant has a higher thermal stability compared to thermal stability of fHbp ID 22. In some cases, the variant fHbp may include a combination of substitutions, such as, L130R, G133D, and at least one amino acid substitution selected from: a) N115I; b) D121G; c) S128T; d) V131; e) K219 (e.g., K219N); and f) G220 (e.g., G220S), wherein the amino acid substitutions are relative to fHbp ID 22 (SEQ ID NO:2), wherein the variant fHbp comprises an amino acid sequence having greater than 85% amino acid sequence identity to SEQ ID NO:2, wherein the variant fHbp binds human factor H (fH) with an affinity that is 50% or less of the affinity of fHbp ID 22 for human fH, and wherein the variant induces a bactericidal antibody response in a mammalian host. The thermal stability of the variant fHbp may be higher than a WT fHbp (e.g., fHbp ID 22) by at least 5° C., 10° C., 15° C., 20° C., or more, e.g., higher by 5° C.-30° C., 5° C.-25° C., 5° C.-20° C., 10° C.-20° C., or 15° C.-20° C. As used herein, "thermal stability" refers to stability of a protein when exposed to higher temperature; a thermal stability variant protein maintains its conformation at a higher temperature than a wild type protein. For example, the variant fHbp, that include the double mutation that increases thermal stability compared to thermal stability of wild type (WT) fHbp, e.g., WT fHbp ID 22, may unfold at a higher temperature compared to WT fHbp. In certain cases, the N-terminal domain of the variant fHbp may unfold at a higher temperature than the N-terminal domain of the WT fHbp (e.g., fHbp ID 22).

Also disclosed herein are fHbp variants that include the mutations that enhance thermal stability as compared to a WT fHbp and further include additional mutations known to reduce binding of fH, such as, those disclosed in US2011/0256180. In certain embodiments, a variant of factor H binding protein (fHbp) is disclosed, wherein the variant comprises amino acid substitutions L130R and G133D and at least one of the substitutions: R80A, D211A, E218A, E248A, G236I, T221A, and H223A relative to fHbp ID 22 (SEQ ID NO:2), wherein the variant comprises an amino acid sequence having greater than 85% amino acid sequence identity to SEQ ID NO:2, wherein the variant fHbp binds human factor H (fH) with an affinity that is 50% or less of the affinity of fHbp ID 22 for human fH, and wherein the variant induces a bactericidal antibody response in a mammalian host.

The present disclosure provides variants of fHbp ID 55. The present disclosure provides a variant of fHbp, wherein the variant comprises at least one amino acid substitution selected from the group consisting of: a) an amino acid substitution of the glutamic acid at position 92 (E92); b) an amino acid substitution of the serine at position 223 (S223); and c) an amino acid substitution of the histidine at position 248 (H248), wherein the amino acid substitutions are relative to fHbp ID 55 (SEQ ID NO:3), wherein the variant comprises an amino acid sequence having at least 90% amino acid sequence identity to SEQ ID NO:3, wherein the variant fHbp binds human factor H (fH) with an affinity that is less than 50% of the affinity of fHbp ID 55 for human fH, and wherein the variant induces a bactericidal antibody response in a mammalian host. In some cases, the variant fHbp binds human fH with an affinity that is 25% or less of the affinity of the fHbp ID 55 for human fH. In some cases, the variant fHbp binds human fH with an affinity that is 10% or less of the affinity of the fHbp ID 55 for human fH. In some cases, the variant fHbp binds human fH with an affinity that is 5% or less of the affinity of the fHbp ID 55 for human fH. In some cases, the amino acid substitution at E92 is E92K, E92R, E92H, E92F, E92Y, or E92W. In some cases, the amino acid substitution at S223 is S223R, S223K, S223H, S223F, S223Y, or S223W. In some cases, the amino acid substitution at H248 is H248L, H248I, H248V, H248D, H248E, H248F, H248Y, or H248W.

The present disclosure provides immunogenic compositions comprising a variant fHbp of the present disclosure. The present disclosure provides an immunogenic composition comprising: a) the variant fHbp according to any one of paragraphs 0006-0010 above; and b) a pharmaceutically acceptable excipient. In some cases, the fHbp variant is in a vesicle preparation prepared from a Neisseria meningitidis strain. In some cases, the pharmaceutically acceptable excipient comprises an adjuvant; e.g., where the adjuvant is aluminum phosphate or aluminum hydroxide. In some cases, the pharmaceutical composition further includes Neisserial surface protein A.

The present disclosure provides a nucleic acid encoding a variant fHbp according to any one of paragraphs 0006-0010 above. The present disclosure provides a recombinant expression vector comprising a nucleic acid encoding a variant fHbp according to any one of paragraphs 0006-0010 above. The present disclosure provides an in vitro host cell comprising a nucleic acid encoding a variant fHbp according to any one of paragraphs 0006-0010 above. The present disclosure provides an in vitro host cell comprising a recombinant expression vector comprising a nucleic acid encoding a variant fHbp according to any one of paragraphs 0006-0010 above.

The present disclosure provides a method of eliciting an antibody response in a mammal, the method comprising administering to a mammal an immunogenic composition of paragraph 0011, above. In some cases, the mammal is a human. In some cases, the antibody response is a bactericidal antibody response to one or more strains of N. meningitidis.

BRIEF DESCRIPTION OF THE DRAWINGS

FIG. 5A depicts bactericidal activity of serum from wild-type mice immunized with fHbp ID 1 mutants. FIG. 5B depicts bactericidal activity of serum from human fH transgenic mice immunized with fHbp ID 1 mutants.

FIG. 6A depicts binding of human fH to fHbp ID 1 double mutants. FIG. 6B depicts binding of murine anti-fHbp monoclonal antibody (mAb) JAR 4 to mutants.

FIG. 8A shows binding of human fH to immobilized fHbp ID 55 mutants, measured by ELISA and FIG. 8B shows binding of murine anti-fHbp monoclonal antibody (mAb) JAR 41 to fHbp mutant ID 55 proteins, measured by ELISA. The mean and range for two to four replicates are shown.

FIG. 10A depicts the bactericidal activity of serum from human fH transgenic mice immunized with the licensed Trumenba vaccine or an investigational fHbp ID 55 mutant S223R. FIG. 10B depicts the relationship between serum human fH concentrations in individual transgenic mice and the serum bactericidal antibody titers (circular symbols). For comparison, the titers of wild-type (WT) mice are shown (squares).

FIGS. 11A-11C depict binding of fHbp ID 22 mutant to human fH, measured by ELISA. The mean and range of two to four replicates are shown. FIG. 11D depicts binding of murine anti-fHbp monoclonal antibody (mAb) JAR 4 to fHbp mutant ID 22 proteins, measured by ELISA. fHbp ID 22 wild-type (WT) and D211A mutant are shown as controls. The mean and range of duplicate measurements are shown.

FIG. 12A and FIG. 12B show bactericidal activity of serum from wild-type mice in two experiments to test different fHbp ID 22 mutants.

FIG. 15A depicts binding of human fH to fHbp ID 22 triple mutants. DM refers to L130R/G133D double mutant. FIG. 15B depicts binding of murine anti-fHbp monoclonal antibody (mAb) JAR 4 to fHbp ID 22 triple mutants.

FIG. 17 provides a table of exemplary fHbp mutants with decreased binding of human fH.

FIG. 18 provides the amino acid sequence of wild-type Human factor H.

FIG. 19 provides amino acid sequences of fHbp ID 1, ID 22, and ID 55 from *N. meningitidis* strains.

FIGS. 20-24 provide amino acid sequences of fHbp ID 1 variants.

FIGS. 25-30 provide amino acid sequences of fHbp ID 22 variants.

FIGS. 31-33 provide amino acid sequences of fHbp ID 55 variants.

FIGS. 34-36 provide amino acid sequences of fHbp ID 1 double mutant variants.

FIGS. 37-39 provide amino acid sequences of fHbp ID 22 double and triple mutant variants.

FIG. 40 provides an amino acid sequence of NspA.

DEFINITIONS

Figure 1:
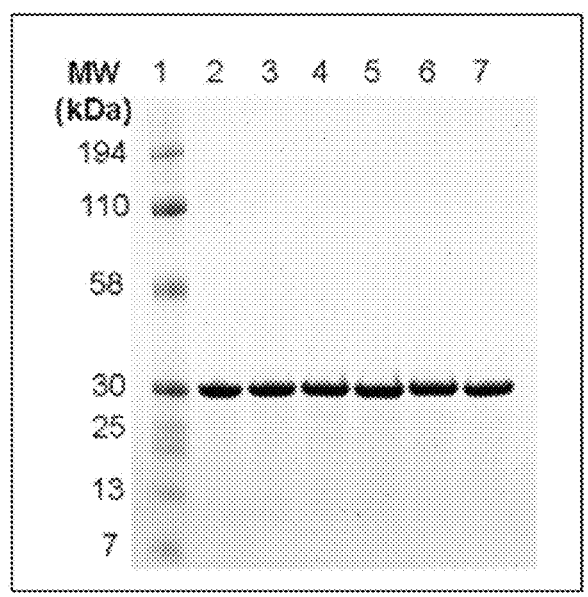
FIG. 1 depicts purified recombinant fHbp ID 1 mutants stained with COOMASSIE blue on a polyacrylamide gel. Lane 1, Kaleidoscope molecular weight marker (Bio-Rad Laboratories); 2, fHbp ID 1 wild-type; 3, Q38R; 4, E92K; 5, R130G; 6, S223R; 7, H248L.

"Factor H Binding Protein" (fHbp), which is also known in the literature as GNA1870, GNA 1870, ORF2086, LP2086 (lipoprotein 2086), and "741" refers to a class of *N. meningitidis* polypeptides. It is found in nature as a lipoprotein on the surface of the bacterium *N. meningitidis*. fHbps have been sub-divided into three fHbp variant groups (referred to as variant group 1 (v.1), variant group 2 (v.2), and variant group 3 (v.3) in some reports (Masignani et al. (2003) *J Exp Med* 197:789-99) and sub-family A and B in other reports (see, e.g., Fletcher et al. (2004) *Infect Immun* 72:2088-2100)) based on amino acid sequence variability and immunologic cross-reactivity (Masignani et al. (2003) *J Exp Med* 197:789-99). fHbp also can be classified into one of the six most common fHbp modular groups, designated Modular Group I to Modular Group VI, as shown in FIG. 2 of Vu et al. (2012) *Sci. Reports* 2:341. Each unique fHbp found in *N. meningitidis* is also assigned an fHbp peptide ID according to the pubmlst.org/neisseria/fHbp/website. Because the length of variant 2 (v.2) fHbp protein (from strain 8047, fHbp ID 77) and variant 3 (v.3) fHbp (from strain M1239, fHbp ID 28) differ by −1 and +7 amino acid residues, respectively, from that from strain MC58 (fHbp ID 1), the numbering used herein to refer to residues for v.2 and v.3 fHbp proteins differs from numbering based on the actual amino acid sequences of these proteins. Thus, for example, reference to a leucine residue (L) at position 166 of the v.2 or v.3 fHbp sequence refers to the residue at position 165 of the v.2 protein and at position 173 in the v.3 protein. Unless noted otherwise, the numbering of the amino acid substitutions present in the fHbp variants is with reference to the numbering of the amino acid residues in fHbp ID 1.

Human factor H ("human fH") as used herein, refers to a protein comprising an amino acid sequence as shown in FIG. 18 (SEQ ID NO:4), and naturally-occurring human allelic variants thereof.

"Derived from" in the context of an amino acid sequence or polynucleotide sequence (e.g., an amino acid sequence "derived from" fHbp ID 1) is meant to indicate that the polypeptide or nucleic acid has a sequence that is based on that of a reference polypeptide or nucleic acid (e.g., a naturally occurring fHbp protein or encoding nucleic acid), and is not meant to be limiting as to the source or method in which the protein or nucleic acid is made. Non-limiting examples of reference polypeptides and reference polynucleotides from which an amino acid sequence or polynucleotide sequence may be "derived from" include a naturally-occurring fHbp, fHbp ID 1, and a non-naturally-occurring fHbp. "Derived from" in the context of bacterial strains is meant to indicate that a strain was obtained through passage in vivo, or in in vitro culture, of a parental strain and/or is a recombinant cell obtained by modification of a parental strain.

"Conservative amino acid substitution" refers to a substitution of one amino acid residue for another sharing chemical and physical properties of the amino acid side chain (e.g., charge, size, hydrophobicity/hydrophilicity). "Conservative substitutions" are intended to include substitution within the following groups of amino acid residues: gly, ala; val, ile, leu; asp, glu; asn, gln; ser, thr; lys, arg; and phe, tyr. Guidance for such substitutions can be drawn from alignments of amino acid sequences of polypeptides presenting the epitope of interest.

The term "protective immunity" means that a vaccine or immunization schedule that is administered to a mammal induces an immune response that prevents, retards the development of, or reduces the severity of a disease that is caused by *Neisseria meningitidis*, or diminishes or altogether eliminates the symptoms of the disease. Protective immunity can be accompanied by production of bactericidal antibodies. It should be noted that production of bactericidal antibodies against *Neisseria meningitidis* is accepted in the field as predictive of a vaccine's protective effect in humans. (Goldschneider et al. (1969) *J. Exp. Med.* 129:1307; Borrow et al. (2001) *Infect Immun.* 69:1568).

The phrase "a disease caused by a strain of *Neisseria meningitidis*" encompasses any clinical symptom or combination of clinical symptoms that are present in an infection of a human with a *Neisseria meningitidis*. These symptoms include but are not limited to: colonization of the upper respiratory tract (e.g. mucosa of the nasopharynx and tonsils) by a pathogenic strain of *Neisseria meningitidis*, penetration of the bacteria into the mucosa and the submucosal vascular bed, septicemia, septic shock, inflammation, hemorrhagic skin lesions, activation of fibrinolysis and of blood coagulation, organ dysfunction such as kidney, lung, and cardiac failure, adrenal hemorrhaging and muscular infarction, capillary leakage, edema, peripheral limb ischemia, respiratory distress syndrome, pericarditis and meningitis.

The phrase "specifically binds to an antibody" or "specifically immunoreactive with", in the context of an antigen (e.g., a polypeptide antigen) refers to a binding reaction that is based on and/or is probative of the presence of the antigen in a sample which may also include a heterogeneous population of other molecules. Thus, under designated conditions, the specified antibody or antibodies bind(s) to a particular antigen or antigens in a sample and do not bind in a significant amount to other molecules present in the sample. "Specifically binds to an antibody" or "specifically immunoreactive with" in the context of an epitope of an antigen (e.g., an epitope of a polypeptide) refers to a binding reaction which is based on and/or is probative of the presence of the epitope in an antigen (e.g., polypeptide) which may also include a heterogeneous population of other epitopes, as well as a heterogeneous population of antigens. Thus, under designated conditions, the specified antibody or antibodies bind(s) to a particular epitope of an antigen and do not bind in a significant amount to other epitopes present in the antigen and/or in the sample.

The phrase "in a sufficient amount to elicit an immune response" means that there is a detectable difference between an immune response indicator measured before and after administration of a particular antigen preparation Immune response indicators include but are not limited to: antibody titer or specificity, as detected by an assay such as enzyme-linked immunosorbent assay (ELISA), bactericidal assay, flow cytometry, immunoprecipitation, Ouchterlony immunodiffusion; binding detection assays of, for example, spot, Western blot or antigen arrays; cytotoxicity assays, etc.

A "surface antigen" is an antigen that is present in a surface structure of *Neisseria meningitidis* (e.g. the outer membrane, capsule, pili, etc.).

"Isolated" refers to an entity of interest that is in an environment different from that in which the compound may naturally occur. "Isolated" is meant to include compounds that are within samples that are substantially enriched for the compound of interest and/or in which the compound of interest is partially or substantially purified. In some cases, an isolated component (e.g., a polypeptide, such as an fHbp variant of the present disclosure; a nucleic acid of the present disclosure; a recombinant vector of the present disclosure) is purified, e.g., the isolated component is at least 80%, at least 85%, at least 90%, at least 95%, at least 98%, at least 99%, or greater than 99%, pure.

"Enriched" means that a sample is non-naturally manipulated (e.g., by an experimentalist or a clinician) so that a compound of interest is present in a greater concentration (e.g., at least a three-fold greater, at least 4-fold greater, at least 8-fold greater, at least 64-fold greater, or more) than the concentration of the compound in the starting sample, such as a biological sample (e.g., a sample in which the compound naturally occurs or in which it is present after administration), or in which the compound was made (e.g., as in a bacterial polypeptide, antibody, nucleic acid, and the like).

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a factor H binding protein" includes a plurality of such factor H binding proteins and reference to "the immunogenic composition" includes reference to one or more immunogenic compositions and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides variant factor H binding proteins (fHbp) that can elicit antibodies that are bactericidal for at least one strain of *Neisseria meningitidis*. The present disclosure provides compositions, including immunogenic compositions, comprising a variant fHbp of the present disclosure. The present disclosure provides methods of use of variant fHbp of the present disclosure, or a composition comprising a variant fHbp of the present disclosure.

Variant fHbp

The present disclosure provides variant fHbp that differ in amino acid sequence from a wild-type *N. meningitidis* fHbp by from 1 to 10 amino acids (e.g., by from 1, 2, 3, 4, 5, 6, 7, 8, 9, or 10 amino acids) from 10 amino acids to 15 amino acids, from 15 amino acids to 20 amino acids, from 20 amino acids to 30 amino acids, from 30 amino acids to 40 amino acids, or from 40 amino acids to 50 amino acids, such that the variant fHbp exhibits reduced affinity to human factor H (fH), compared to a reference fHbp, and where the variant fHbp elicits a bactericidal immune response to one or more *N. meningitidis* strains when administered to a mammalian host. In some cases, the variant fHbp differs in amino acid sequence from a reference wild-type *N. meningitidis* fHbp by no more than from 1 to 10 acid substitutions. In some cases, the variant fHbp differs in amino acid sequence from a reference wild-type *N. meningitidis* fHbp by only one amino acid substitution.

In some cases, variant fHbp of the present disclosure comprises an amino acid sequence having at least 80%, at least 85%, at least 90%, at least 95%, at least 98%, or at least 99%, amino acid sequence identity to a reference fHbp sequence; where the variant fHbp comprises one or more amino acid substitutions relative to the reference fHbp sequence such that the variant fHbp exhibits an affinity for human fH that is 85% or less of the binding affinity of the reference fHbp for human fH, e.g., the variant fHbp exhibits an affinity for human fH that is from about 85% to about 75%, from about 75% to about 65%, from about 65% to about 55%, from about 55% to about 45%, from about 45% to about 35%, from about 35% to about 25%, from about 25% to about 15%, from about 15% to about 10%, from about 10% to about 5%, from about 5% to about 2%, from about 2% to about 1%, or from about 1% to about 0.1%, or less than 0.1%, of the binding affinity of the affinity of the reference fHbp for human fH; and the variant fHbp induces a bactericidal immune response to at least one strain of *N. meningitidis* when administered to a mammalian host (e.g., a human; or a non-human animal model).

A variant fHbp of the present disclosure maintains substantially the same conformation of a reference (e.g., wild-type) fHbp that binds human fH when the reference fHbp is in its native conformation. Whether a variant fHbp of the present disclosure maintains substantially the same conformation of a reference (e.g., wild-type) fHbp that binds human fH can be determined using antibodies that bind wild-type fHbp when the wild-type fHbp is in its native conformation. Such antibodies include, e.g., JAR 41; JAR 4; and JAR 31. See, e.g., Vu et al. (2012) *Sci. Reports* 2:341. A hybridoma producing JAR 4 monoclonal antibody has the American Type Culture Collection (ATCC) number PTA-8943; see also U.S. Pat. No. 8,470,340. For example, in some cases, a variant fHbp of the present disclosure retains binding to JAR 4; e.g., a variant fHbp of the present disclosure retains at least 75%, at least 80%, at least 85%, at least 90%, or at least 95%, binding to JAR 4 of a reference fHbp (e.g., fHbp ID 1, fHbp ID 22, or fHbp ID 55) in its native conformation.

Variants of fHbp ID 1

A "reference fHbp" from which a variant fHbp of the present disclosure is derived is in some cases fHbp ID 1. The amino acid sequence of fHbp ID 1 is set out below.

fHbp ID 1:

(SEQ ID NO: 1)
CSSGGGGVAADIGAGLADALTAPLDHKDKGLQSLTLDQSVRKNEKLKLAA

QGAEKTYGNGDSLNTGKLKNDKVSRFDFIRQIEVDGQLITLESGEFQVYK

QSHSALTAFQTEQIQDSEHSGKMVAKRQFRIGDIAGEHTSFDKLPEGGRA

TYRGTAFGSDDAGGKLTYTIDFAAKQGNGKIEHLKSPELNVDLAAADIKP

DGKRHAVISGSVLYNQAEKGSYSLGIFGGKAQEVAGSAEVKTVNGIRHIG

LAAKQ.

In some cases, a variant fHbp of the present disclosure is a variant group 1 fHbp. In some cases, a variant fHbp of the present disclosure is a variant group 1 fHbp, and is a modular group I fHbp. In some cases, variant fHbp of the present disclosure comprises an amino acid sequence having at least 80%, at least 85%, at least 90%, at least 95%, at least 98%, or at least 99%, amino acid sequence identity to SEQ ID NO:1; where the variant fHbp comprises one or more amino acid substitutions relative to fHbp ID 1 such that the variant fHbp exhibits an affinity for human fH that is 85% or less of the binding affinity of fHbp ID 1 for human fH, e.g., the variant fHbp exhibits an affinity for human fH that is from about 85% to about 75%, from about 75% to about 65%, from about 65% to about 55%, from about 55% to about 45%, from about 45% to about 35%, from about 35% to about 25%, from about 25% to about 15%, from about 15% to about 10%, from about 10% to about 5%, from about 5% to about 2%, from about 2% to about 1%, or from about 1% to about 0.1%, or less than 0.1%, of the binding affinity of the affinity of fHbp ID 1 for human fH; and the variant fHbp induces a bactericidal immune response to at least one strain of *N. meningitidis* when administered to a mammalian host (e.g., a human; or a non-human animal model).

In some cases, a variant fHbp of the present disclosure comprises an amino acid sequence having at least 80%, at least 85%, at least 90%, at least 95%, at least 98%, or at least 99%, amino acid sequence identity to SEQ ID NO:1, where the variant fHbp binds human fH with an affinity that 50% or less (e.g., from about 50% to about 45%, from about 45% to about 35%, from about 35% to about 25%, from about 25% to about 15%, from about 15% to about 10%, from about 10% to about 5%, from about 5% to about 2%, from about 2% to about 1%, or from about 1% to about 0.1%, or less than 0.1%) of the affinity of fHbp ID 1 for human fH, where the variant induces a bactericidal antibody response to at least one strain of *N. meningitidis* in a mammalian host, and where the variant fHbp comprises an amino acid substitution selected from at least one of: a) an amino acid substitution of the glutamine at amino acid 38 (Q38); b) an amino acid substitution of the glutamic acid at amino acid 92 (E92); c) a substitution of glycine for arginine at amino acid 130 (R130G); d) an amino acid substitution of the serine at amino acid 223 (S223); and e) a substitution of histidine for leucine at amino acid 248 (H248L), based on the numbering of fHbp ID 1.

In some cases, a variant fHbp of the present disclosure comprises an amino acid sequence having at least 80%, at least 85%, at least 90%, at least 95%, at least 98%, or at least 99%, amino acid sequence identity to SEQ ID NO:1, where the variant fHbp binds human fH with an affinity that 50% or less (e.g., from about 50% to about 45%, from about 45% to about 35%, from about 35% to about 25%, from about 25% to about 15%, from about 15% to about 10%, from about 10% to about 5%, from about 5% to about 2%, from about 2% to about 1%, or from about 1% to about 0.1%, or less than 0.1%) of the affinity of fHbp ID 1 for human fH, where the variant induces a bactericidal antibody response to at least one strain of *N. meningitidis* in a mammalian host, and where the variant fHbp comprises an amino acid substitution of the glutamine at amino acid 38 (Q38). In some cases, the variant fHbp comprises a Q38R substitution. Other amino acids with positively charged or aromatic side chains, such as lysine, histidine, phenylalanine, tyrosine or tryptophan, also may be substituted at this position. Thus, in some cases, the variant fHbp comprises a Q38K substitution, a Q38H substitution, a Q38F substitution, a Q38Y substitution, or a Q38W substitution. As one example, a variant fHbp of the present disclosure can comprise the amino acid sequence depicted in FIG. 20 and set forth in SEQ ID NO:5.

In some cases, a variant fHbp of the present disclosure comprises an amino acid sequence having at least 80%, at least 85%, at least 90%, at least 95%, at least 98%, or at least 99%, amino acid sequence identity to SEQ ID NO:1, where the variant fHbp binds human fH with an affinity that 50% or less (e.g., from about 50% to about 45%, from about 45% to about 35%, from about 35% to about 25%, from about 25% to about 15%, from about 15% to about 10%, from about 10% to about 5%, from about 5% to about 2%, from about 2% to about 1%, or from about 1% to about 0.1%, or less than 0.1%) of the affinity of fHbp ID 1 for human fH, where the variant induces a bactericidal antibody response to at least one strain of *N. meningitidis* in a mammalian host, and where the variant fHbp comprises an amino acid substitution of the glutamic acid at amino acid 92 (E92). In some cases the fHbp variant comprises an E92K substitution. Other amino acids with positively charged or aromatic side chains, such as arginine, histidine, phenylalanine, tyrosine or tryptophan, also may be substituted at this position. Thus, for example, in some cases the fHbp variant comprises an E92R substitution, an E92H substitution, an E92F substitution, an E92Y substitution, or an E92W substitution. As one example, a variant fHbp of the present disclosure can comprise the amino acid sequence depicted in FIG. 21 and set forth in SEQ ID NO:6.

In some cases, a variant fHbp of the present disclosure comprises an amino acid sequence having at least 80%, at least 85%, at least 90%, at least 95%, at least 98%, or at least 99%, amino acid sequence identity to SEQ ID NO:1, where the variant fHbp binds human fH with an affinity that 50% or less (e.g., from about 50% to about 45%, from about 45% to about 35%, from about 35% to about 25%, from about 25% to about 15%, from about 15% to about 10%, from about 10% to about 5%, from about 5% to about 2%, from about 2% to about 1%, or from about 1% to about 0.1%, or less than 0.1%) of the affinity of fHbp ID 1 for human fH, where the variant induces a bactericidal antibody response to at least one strain of *N. meningitidis* in a mammalian host, and where the variant fHbp comprises a substitution of glycine for arginine at amino acid 130 (R130G). For example, a variant fHbp of the present disclosure can comprise the amino acid sequence depicted in FIG. 22 and set forth in SEQ ID NO:7. Other amino acids with negatively charged or aromatic side chains, such as aspartate, glutamate, phenylalanine, tyrosine, or tryptophan, may also be substituted at R130. Thus, for example, in some cases, a variant fHbp of the present disclosure comprises an amino acid sequence having at least 80%, at least 85%, at least 90%, at least 95%, at least 98%, or at least 99%, amino acid sequence identity to SEQ ID NO:1, where the variant fHbp binds human fH with an affinity that 50% or less (e.g., from about 50% to about 45%, from about 45% to about 35%, from about 35% to about 25%, from about 25% to about 15%, from about 15% to about 10%, from about 10% to about 5%, from about 5% to about 2%, from about 2% to about 1%, or from about 1% to about 0.1%, or less than 0.1%) of the affinity of fHbp ID 1 for human fH, where the variant induces a bactericidal antibody response to at least one strain of *N. meningitidis* in a mammalian host, and where the variant fHbp comprises an R130D substitution, an R130E substitution, an R130F substitution, an R130Y substitution, or an R130W substitution.

In some cases, a variant fHbp of the present disclosure comprises an amino acid sequence having at least 80%, at least 85%, at least 90%, at least 95%, at least 98%, or at least 99%, amino acid sequence identity to SEQ ID NO:1, where the variant fHbp binds human fH with an affinity that 50% or less (e.g., from about 50% to about 45%, from about 45% to about 35%, from about 35% to about 25%, from about 25% to about 15%, from about 15% to about 10%, from about 10% to about 5%, from about 5% to about 2%, from about 2% to about 1%, or from about 1% to about 0.1%, or less than 0.1%) of the affinity of fHbp ID 1 for human fH, where the variant induces a bactericidal antibody response to at least one strain of *N. meningitidis* in a mammalian host, and where the variant fHbp comprises an amino acid substitution of the serine at amino acid 223 (S223). In some cases, the fHbp variant comprises an S223R substitution. Other amino acids with positively charged or aromatic side chains, such as lysine, histidine, phenylalanine, tyrosine or tryptophan, also may be substituted at this position. Thus, for example, in some cases, the fHbp variant comprises an S223K substitution, an S223H substitution, an S223F substitution, an S223Y substitution, or an S223W substitution. As one example, a variant fHbp of the present disclosure can comprise the amino acid sequence depicted in FIG. 23 and set forth in SEQ ID NO:8.

In some cases, a variant fHbp of the present disclosure comprises an amino acid sequence having at least 80%, at least 85%, at least 90%, at least 95%, at least 98%, or at least 99%, amino acid sequence identity to SEQ ID NO:1, where the variant fHbp binds human fH with an affinity that 50% or less (e.g., from about 50% to about 45%, from about 45% to about 35%, from about 35% to about 25%, from about 25% to about 15%, from about 15% to about 10%, from about 10% to about 5%, from about 5% to about 2%, from about 2% to about 1%, or from about 1% to about 0.1%, or less than 0.1%) of the affinity of fHbp ID 1 for human fH, where the variant induces a bactericidal antibody response to at least one strain of *N. meningitidis* in a mammalian host, and where the variant fHbp comprises a substitution of histidine for leucine at amino acid 248 (H248L). For example, a variant fHbp of the present disclosure can comprise the amino acid sequence depicted in FIG. 24 and set forth in SEQ ID NO:9. Other amino acids with non-polar, negatively charged or aromatic side chains, such as isoleucine, valine, aspartate, glutamate, phenylalanine, tyrosine or tryptophan, also may be substituted at H248. Thus, in some cases, a variant fHbp of the present disclosure comprises an amino acid sequence having at least 80%, at least 85%, at least 90%, at least 95%, at least 98%, or at least 99%, amino acid sequence identity to SEQ ID NO:1, where the variant fHbp binds human fH with an affinity that 50% or less (e.g., from about 50% to about 45%, from about 45% to about 35%, from about 35% to about 25%, from about 25% to about 15%, from about 15% to about 10%, from about 10% to about 5%, from about 5% to about 2%, from about 2% to about 1%, or from about 1% to about 0.1%, or less than 0.1%) of the affinity of fHbp ID 1 for human fH, where the variant induces a bactericidal antibody response to at least one strain of *N. meningitidis* in a mammalian host, and where the variant fHbp comprises an H248I substitution, an H248V substitution, an H248D substitution, an H248E substitution, an H248F substitution, an H248Y substitution, or an H248W substitution.

Combinations of Amino Acid Substitutions

In some cases, a variant fHbp of the present disclosure comprises an amino acid sequence having at least 80%, at least 85%, at least 90%, at least 95%, at least 98%, or at least 99%, amino acid sequence identity to SEQ ID NO:1, where the variant fHbp binds human fH with an affinity that 50% or less (e.g., from about 50% to about 45%, from about 45% to about 35%, from about 35% to about 25%, from about 25% to about 15%, from about 15% to about 10%, from about 10% to about 5%, from about 5% to about 2%, from about 2% to about 1%, or from about 1% to about 0.1%, or less than 0.1%) of the affinity of fHbp ID 1 for human fH, where the variant induces a bactericidal antibody response to at least one strain of *N. meningitidis* in a mammalian host, and where the variant fHbp comprises an amino acid substitution selected from two or more of: a) an amino acid substitution of the glutamine at amino acid 38 (Q38); b) an amino acid substitution of the glutamic acid at amino acid 92 (E92); c) a substitution of glycine for arginine at amino acid 130 (R130G); d) an amino acid substitution of the serine at amino acid 223 (S223); and e) a substitution of histidine for leucine at amino acid 248 (H248L), based on the numbering of fHbp ID 1.

Combinations of substitutions may be included wherein the two substitutions are in different structural domains, and each independently decreases binding of fH to fHbp (e.g., one substitution in the N-terminal domain, in combination with an amino acid substitution in the C-terminal domain. In some cases, a variant fHbp of the present disclosure comprises a first amino acid substitution within the N-terminal domain; and a second amino acid substitution within the C-terminal domain. In some cases, a variant fHbp of the present disclosure comprises a first amino acid substitution within the N-terminal domain; and a second amino acid substitution within the N-terminal domain. In some cases, a variant fHbp of the present disclosure comprises a first amino acid substitution within the C-terminal domain; and a second amino acid substitution within the C-terminal domain.

For example, in some cases, a variant fHbp of the present disclosure comprises an amino acid sequence having at least 80%, at least 85%, at least 90%, at least 95%, at least 98%, or at least 99%, amino acid sequence identity to SEQ ID NO:1, where the variant fHbp binds human fH with an affinity that 50% or less (e.g., from about 50% to about 45%, from about 45% to about 35%, from about 35% to about 25%, from about 25% to about 15%, from about 15% to about 10%, from about 10% to about 5%, from about 5% to about 2%, from about 2% to about 1%, or from about 1% to about 0.1%, or less than 0.1%) of the affinity of fHbp ID 1 for human fH, where the variant induces a bactericidal antibody response to at least one strain of *N. meningitidis* in a mammalian host, and where the variant fHbp comprises: a) an amino acid substitution of the glutamine at amino acid 38 (Q38) and b) an amino acid substitution of the glutamic acid at amino acid 92 (E92); or where the variant fHbp comprises: a) an amino acid substitution of the glutamine at amino acid 38 (Q38) and c) a substitution of glycine for arginine at amino acid 130 (R130G); or where the variant fHbp comprises a) an amino acid substitution of the glutamine at amino acid 38 (Q38) and d) an amino acid substitution of the serine at amino acid 223 (S223); or where the variant fHbp comprises a) an amino acid substitution of the glutamine at amino acid 38 (Q38) and e) a substitution of histidine for leucine at amino acid 248 (H248L), based on the numbering of fHbp ID 1.

As additional non-limiting examples, in some cases, a variant fHbp of the present disclosure comprises an amino acid sequence having at least 80%, at least 85%, at least 90%, at least 95%, at least 98%, or at least 99%, amino acid sequence identity to SEQ ID NO:1, where the variant fHbp binds human fH with an affinity that 50% or less (e.g., from about 50% to about 45%, from about 45% to about 35%, from about 35% to about 25%, from about 25% to about 15%, from about 15% to about 10%, from about 10% to about 5%, from about 5% to about 2%, from about 2% to about 1%, or from about 1% to about 0.1%, or less than 0.1%) of the affinity of fHbp ID 1 for human fH, where the variant induces a bactericidal antibody response to at least one strain of *N. meningitidis* in a mammalian host, and where the variant fHbp comprises: b) an amino acid substitution of the glutamic acid at amino acid 92 (E92) and c) a substitution of glycine for arginine at amino acid 130 (R130G); or where the variant fHbp comprises b) an amino acid substitution of the glutamic acid at amino acid 92 (E92) and d) an amino acid substitution of the serine at amino acid 223 (S223); or where the variant fHbp comprises b) an amino acid substitution of the glutamic acid at amino acid 92 (E92) and e) a substitution of histidine for leucine at amino acid 248 (H248L); or where the variant fHbp comprises c) a substitution of glycine for arginine at amino acid 130 (R130G) and d) an amino acid substitution of the serine at amino acid 223 (S223); or where the variant fHbp comprises c) a substitution of glycine for arginine at amino acid 130 (R130G) and e) a substitution of histidine for leucine at amino acid 248 (H248L); or where the variant fHbp comprises d) an amino acid substitution of the serine at amino acid 223 (S223) and e) a substitution of histidine for leucine at amino acid 248 (H248L), based on the numbering of fHbp ID 1.

As additional non-limiting examples, in some cases, a variant fHbp of the present disclosure comprises an amino acid sequence having at least 80%, at least 85%, at least 90%, at least 95%, at least 98%, or at least 99%, amino acid sequence identity to SEQ ID NO:1, where the variant fHbp binds human fH with an affinity that 50% or less (e.g., from about 50% to about 45%, from about 45% to about 35%, from about 35% to about 25%, from about 25% to about 15%, from about 15% to about 10%, from about 10% to about 5%, from about 5% to about 2%, from about 2% to about 1%, or from about 1% to about 0.1%, or less than 0.1%) of the affinity of fHbp ID 1 for human fH, where the variant induces a bactericidal antibody response to at least one strain of N. meningitidis in a mammalian host, and where the variant fHbp comprises: i) a Q38R substitution; and ii) an R130G substitution, based on the numbering of fHbp ID 1.

Also provided herein are variant fHbp proteins that include one or more substitutions relative to amino acid sequence of fHbp ID 1 as set forth above and further include the substitution R41S. Exemplary variant fHbp include a R41S substitution and a substitution at S223, e.g., R41S/S223R relative to fHbp ID 1 or a R41S substitution and a H248L substitution relative to fHbp ID 1. In some cases, a variant fHbp of the present disclosure comprises an amino acid sequence having at least 80%, at least 85%, at least 90%, at least 95%, at least 98%, or at least 99%, amino acid sequence identity to SEQ ID NO:1, where the variant fHbp binds human fH with an affinity that 50% or less (e.g., from about 50% to about 45%, from about 45% to about 35%, from about 35% to about 25%, from about 25% to about 15%, from about 15% to about 10%, from about 10% to about 5%, from about 5% to about 2%, from about 2% to about 1%, or from about 1% to about 0.1%, or less than 0.1%) of the affinity of fHbp ID 22 for human fH, where the variant induces a bactericidal antibody response to at least one strain of N. meningitidis in a mammalian host, and where the variant fHbp comprises two or more of the following amino acid substitutions: a) a substitution of serine for arginine at amino acid 41 (R41S); b) a substitution of arginine for serine at amino acid 223 (S223R); c) a substitution of leucine for histidine at amino acid 248 (H248L), based on the numbering of fHbp ID 1.

Also disclosed herein are variant fHbp proteins that include one or more substitutions relative to amino acid sequence of fHbp ID 1 as set forth above and further include the substitutions disclosed in US2011/0256180, which is herein incorporated by reference in its entirety.

Variants of fHbp ID 22

A "reference fHbp" from which a variant fHbp of the present disclosure is derived is in some cases fHbp ID 22. The amino acid sequence of fHbp ID 22 is set out below.

fHbp ID 22:
(SEQ ID NO: 2)
CSSGGGGVAADIGAGLADALTAPLDHKDKSLQSLTLDQSVRKNEKLKLAA

QGAEKTYGNGDSLNTGKLKNDKVSRFDFIRQIEVDGQLITLESGEFQIYK

QDHSAVVALQIEKINNPDKIDSLINQRSFLVSGLGGEHTAFNQLPSGKAE

YHGKAFSSDDPNGRLHYSIDFTKKQGYGRIEHLKTPEQNVELASAELKAD

EKSHAVILGDTRYGGEEKGTYHLALFGDRAQEIAGSATVKIREKVHEIGI

AGKQ.

In some cases, a variant fHbp of the present disclosure is a variant group 2 fHbp. In some cases, a variant fHbp of the present disclosure is a variant group 2 fHbp, and is a modular group III fHbp. In some cases, variant fHbp of the present disclosure comprises an amino acid sequence having at least 80%, at least 85%, at least 90%, at least 95%, at least 98%, or at least 99%, amino acid sequence identity to SEQ ID NO:2; where the variant fHbp comprises one or more amino acid substitutions relative to fHbp ID 22 such that the variant fHbp exhibits an affinity for human fH that is 85% or less of the binding affinity of fHbp ID 22 for human fH, e.g., the variant fHbp exhibits an affinity for human fH that is from about 85% to about 75%, from about 75% to about 65%, from about 65% to about 55%, from about 55% to about 45%, from about 45% to about 35%, from about 35% to about 25%, from about 25% to about 15%, from about 15% to about 10%, from about 10% to about 5%, from about 5% to about 2%, from about 2% to about 1%, or from about 1% to about 0.1%, or less than 0.1%, of the binding affinity of the affinity of fHbp ID 22 for human fH; and the variant fHbp induces a bactericidal immune response to at least one strain of N. meningitidis when administered to a mammalian host (e.g., a human; or a non-human animal model).

In some cases, a variant fHbp of the present disclosure comprises an amino acid sequence having at least 80%, at least 85%, at least 90%, at least 95%, at least 98%, or at least 99%, amino acid sequence identity to SEQ ID NO:2, where the variant fHbp binds human fH with an affinity that 50% or less (e.g., from about 50% to about 45%, from about 45% to about 35%, from about 35% to about 25%, from about 25% to about 15%, from about 15% to about 10%, from about 10% to about 5%, from about 5% to about 2%, from about 2% to about 1%, or from about 1% to about 0.1%, or less than 0.1%) of the affinity of fHbp ID 22 for human fH, where the variant induces a bactericidal antibody response to at least one strain of N. meningitidis in a mammalian host, and where the variant fHbp comprises an amino acid substitution selected from at least one of: a) a substitution of isoleucine for asparagine at amino acid 115 (N115I); b) a substitution of glycine for aspartic acid at amino acid 121 (D121G); c) a substitution of threonine for serine at amino acid 128 (S128T); d) an amino acid substitution of the valine at position 131 (V131); e) an amino acid substitution of the lysine at position 219 (K219); f) an amino acid substitution of the glycine at position 220 (G220), relative to the amino acid sequence of fHbp ID 22. As noted herein, the numbering of the amino acid residue is based on that of fHbp ID 1.

In some cases, a variant fHbp of the present disclosure comprises an amino acid sequence having at least 80%, at least 85%, at least 90%, at least 95%, at least 98%, or at least 99%, amino acid sequence identity to SEQ ID NO:2, where the variant fHbp binds human fH with an affinity that 50% or less (e.g., from about 50% to about 45%, from about 45% to about 35%, from about 35% to about 25%, from about 25% to about 15%, from about 15% to about 10%, from about 10% to about 5%, from about 5% to about 2%, from about 2% to about 1%, or from about 1% to about 0.1%, or less than 0.1%) of the affinity of fHbp ID 22 for human fH, where the variant induces a bactericidal antibody response to at least one strain of N. meningitidis in a mammalian host, and where the variant fHbp comprises a substitution of isoleucine for asparagine at amino acid 115 (N115I). For example, a variant fHbp of the present disclosure can comprise the amino acid sequence depicted in FIG. 25 and set forth in SEQ ID NO:10. Other amino acids with non-polar, positively charged or aromatic side chains, such as valine, leucine, lysine, arginine, histidine, phenylalanine, tyrosine or tryptophan, also may be substituted at N115. Thus, for example, in some cases, a variant fHbp of the present disclosure comprises an amino acid sequence having at least 80%, at least 85%, at least 90%, at least 95%, at least 98%, or at least 99%, amino acid sequence identity to SEQ ID NO:2, where the variant fHbp binds human fH with an affinity that 50% or less (e.g., from about 50% to about 45%, from about 45% to about 35%, from about 35% to about 25%, from about 25% to about 15%, from about 15% to about 10%, from about 10% to about 5%, from about 5% to about 2%, from about 2% to about 1%, or from about 1% to about 0.1%, or less than 0.1%) of the affinity of fHbp ID 22 for human fH, where the variant induces a bactericidal antibody response to at least one strain of N. meningitidis in a mammalian host, and where the variant fHbp comprises an N115V substitution, an N115L substitution, an N115K substitution, an N115R substitution, an N115H substitution, an N115F substitution, an N115Y substitution, or an N115W substitution relative to amino acid sequence of fHbp ID 22.

In some cases, a variant fHbp of the present disclosure comprises an amino acid sequence having at least 80%, at least 85%, at least 90%, at least 95%, at least 98%, or at least 99%, amino acid sequence identity to SEQ ID NO:2, where the variant fHbp binds human fH with an affinity that 50% or less (e.g., from about 50% to about 45%, from about 45% to about 35%, from about 35% to about 25%, from about 25% to about 15%, from about 15% to about 10%, from about 10% to about 5%, from about 5% to about 2%, from about 2% to about 1%, or from about 1% to about 0.1%, or less than 0.1%) of the affinity of fHbp ID 22 for human fH, where the variant induces a bactericidal antibody response to at least one strain of N. meningitidis in a mammalian host, and where the variant fHbp comprises a substitution of glycine for aspartic acid at amino acid 121 (D121G). For example, a variant fHbp of the present disclosure can comprise the amino acid sequence depicted in FIG. 26 and set forth in SEQ ID NO:11. Other amino acids with non-polar, positively charged or aromatic side chains, such as leucine, isoleucine, valine, lysine, arginine, histidine, phenylalanine, tyrosine or tryptophan, also may be substituted at D121. Thus, for example, in some cases, a variant fHbp of the present disclosure comprises an amino acid sequence having at least 80%, at least 85%, at least 90%, at least 95%, at least 98%, or at least 99%, amino acid sequence identity to SEQ ID NO:2, where the variant fHbp binds human fH with an affinity that 50% or less (e.g., from about 50% to about 45%, from about 45% to about 35%, from about 35% to about 25%, from about 25% to about 15%, from about 15% to about 10%, from about 10% to about 5%, from about 5% to about 2%, from about 2% to about 1%, or from about 1% to about 0.1%, or less than 0.1%) of the affinity of fHbp ID 22 for human fH, where the variant induces a bactericidal antibody response to at least one strain of N. meningitidis in a mammalian host, and where the variant fHbp comprises a D121L substitution, a D121I substitution, a D121V substitution, a D121K substitution, a D121R substitution, a D121H substitution, a D121F substitution, a D121Y substitution, or a D121W substitution relative to amino acid sequence of fHbp ID 22.

In some cases, a variant fHbp of the present disclosure comprises an amino acid sequence having at least 80%, at least 85%, at least 90%, at least 95%, at least 98%, or at least 99%, amino acid sequence identity to SEQ ID NO:2, where the variant fHbp binds human fH with an affinity that 50% or less (e.g., from about 50% to about 45%, from about 45% to about 35%, from about 35% to about 25%, from about 25% to about 15%, from about 15% to about 10%, from about 10% to about 5%, from about 5% to about 2%, from about 2% to about 1%, or from about 1% to about 0.1%, or less than 0.1%) of the affinity of fHbp ID 22 for human fH, where the variant induces a bactericidal antibody response to at least one strain of N. meningitidis in a mammalian host, and where the variant fHbp comprises a substitution of threonine for serine at amino acid 128 (S128T). For example, a variant fHbp of the present disclosure can comprise the amino acid sequence depicted in FIG. 27 and set forth in SEQ ID NO:12. Other amino acids with polar, charged or aromatic side chains, such as methionine, asparagine, glutamine, aspartate, glutamate, lysine, arginine, histidine, phenylalanine, tyrosine or tryptophan, also may be substituted at S128. Thus, for example, in some cases, a variant fHbp of the present disclosure comprises an amino acid sequence having at least 80%, at least 85%, at least 90%, at least 95%, at least 98%, or at least 99%, amino acid sequence identity to SEQ ID NO:2, where the variant fHbp binds human fH with an affinity that 50% or less (e.g., from about 50% to about 45%, from about 45% to about 35%, from about 35% to about 25%, from about 25% to about 15%, from about 15% to about 10%, from about 10% to about 5%, from about 5% to about 2%, from about 2% to about 1%, or from about 1% to about 0.1%, or less than 0.1%) of the affinity of fHbp ID 22 for human fH, where the variant induces a bactericidal antibody response to at least one strain of N. meningitidis in a mammalian host, and where the variant fHbp comprises an S128M substitution, an S128N substitution, an S128D substitution, an S128E substitution, an S128K substitution, an S128R substitution, an S128H substitution, an S128F substitution, an S128Y substitution, or an S128W substitution relative to amino acid sequence of fHbp ID 22.

In some cases, a variant fHbp of the present disclosure comprises an amino acid sequence having at least 80%, at least 85%, at least 90%, at least 95%, at least 98%, or at least 99%, amino acid sequence identity to SEQ ID NO:2, where the variant fHbp binds human fH with an affinity that 50% or less (e.g., from about 50% to about 45%, from about 45% to about 35%, from about 35% to about 25%, from about 25% to about 15%, from about 15% to about 10%, from about 10% to about 5%, from about 5% to about 2%, from about 2% to about 1%, or from about 1% to about 0.1%, or less than 0.1%) of the affinity of fHbp ID 22 for human fH, where the variant induces a bactericidal antibody response to at least one strain of N. meningitidis in a mammalian host, and where the variant fHbp comprises an amino acid substitution of the valine at position 131 (V131). In some cases, the fHbp variant comprises a V131D substitution. Other amino acids with charged or aromatic side chains, such as glutamate, lysine, arginine, histidine, phenylalanine, tyrosine or tryptophan, also may be substituted at this position. Thus, for example, in some cases, the fHbp variant comprises a V131E substitution, a V131K substitution, a V131R substitution, a V131H substitution, a V131F substitution, a V131Y substitution, or a V131W substitution. As one example, a variant fHbp of the present disclosure can comprise the amino acid sequence depicted in FIG. 28 and set forth in SEQ ID NO:13 relative to amino acid sequence of fHbp ID 22.

In some cases, a variant fHbp of the present disclosure comprises an amino acid sequence having at least 80%, at least 85%, at least 90%, at least 95%, at least 98%, or at least 99%, amino acid sequence identity to SEQ ID NO:2, where the variant fHbp binds human fH with an affinity that 50% or less (e.g., from about 50% to about 45%, from about 45% to about 35%, from about 35% to about 25%, from about 25% to about 15%, from about 15% to about 10%, from about 10% to about 5%, from about 5% to about 2%, from about 2% to about 1%, or from about 1% to about 0.1%, or less than 0.1%) of the affinity of fHbp ID 22 for human fH, where the variant induces a bactericidal antibody response to at least one strain of *N. meningitidis* in a mammalian host, and where the variant fHbp comprises an amino acid substitution of the lysine at position 219 (K219). In some cases, the fHbp variant comprises a K219N substitution. Other amino acids with polar, negatively charged or aromatic side chains, such as glutamine, aspartate, glutamate, phenylalanine, tyrosine or tryptophan, also may be substituted at this position. Thus, for example, in some cases, the fHbp variant comprises a K219Q substitution, a K219D substitution, a K219E substitution, a K219F substitution, a K219Y substitution, or a K219W substitution. As one example, a variant fHbp of the present disclosure can comprise the amino acid sequence depicted in FIG. 29 and set forth in SEQ ID NO:14.

In some cases, a variant fHbp of the present disclosure comprises an amino acid sequence having at least 80%, at least 85%, at least 90%, at least 95%, at least 98%, or at least 99%, amino acid sequence identity to SEQ ID NO:2, where the variant fHbp binds human fH with an affinity that 50% or less (e.g., from about 50% to about 45%, from about 45% to about 35%, from about 35% to about 25%, from about 25% to about 15%, from about 15% to about 10%, from about 10% to about 5%, from about 5% to about 2%, from about 2% to about 1%, or from about 1% to about 0.1%, or less than 0.1%) of the affinity of fHbp ID 22 for human fH, where the variant induces a bactericidal antibody response to at least one strain of *N. meningitidis* in a mammalian host, and where the variant fHbp comprises an amino acid substitution of the glycine at position 220 (G220). In some cases, the fHbp variant comprises a G220S substitution. Other amino acids with polar, charged or aromatic side chains, such as asparagine, glutamine, aspartate, glutamate, lysine, arginine, histidine, phenylalanine, tyrosine or tryptophan, also may be substituted at this position. Thus, for example, in some cases, the fHbp variant comprises a G220N substitution, a G220Q substitution, a G220D substitution, a G220E substitution, a G220K substitution, a G220R substitution, a G220H substitution, a G220F substitution, a G220Y substitution, or a G220W substitution. For example, a variant fHbp of the present disclosure can comprise the amino acid sequence depicted in FIG. 30 and set forth in SEQ ID NO:15.

Combinations of Amino Acid Substitutions

In some cases, a variant fHbp of the present disclosure comprises an amino acid sequence having at least 80%, at least 85%, at least 90%, at least 95%, at least 98%, or at least 99%, amino acid sequence identity to SEQ ID NO:2, where the variant fHbp binds human fH with an affinity that 50% or less (e.g., from about 50% to about 45%, from about 45% to about 35%, from about 35% to about 25%, from about 25% to about 15%, from about 15% to about 10%, from about 10% to about 5%, from about 5% to about 2%, from about 2% to about 1%, or from about 1% to about 0.1%, or less than 0.1%) of the affinity of fHbp ID 22 for human fH, where the variant induces a bactericidal antibody response to at least one strain of *N. meningitidis* in a mammalian host, and where the variant fHbp comprises an amino acid substitution selected from two or more of: a) a substitution of isoleucine for asparagine at amino acid 115 (N115I); b) a substitution of glycine for aspartic acid at amino acid 121 (D121G); c) a substitution of threonine for serine at amino acid 128 (S128T); d) an amino acid substitution of the valine at position 131 (V131); e) an amino acid substitution of the lysine at position 219 (K219); f) an amino acid substitution of the glycine at position 220 (G220), relative to amino acid sequence of fHbp ID 22. As noted herein, the numbering of the residues is based on the numbering of the amino acids in fHbp ID 1.

Combinations of substitutions may be included wherein the two substitutions are in different structural domains, and each independently decreases binding of fH to fHbp (e.g., one substitution in the N-terminal domain, in combination with an amino acid substitution in the C-terminal domain. In some cases, a variant fHbp of the present disclosure comprises a first amino acid substitution within the N-terminal domain; and a second amino acid substitution within the C-terminal domain. In some cases, a variant fHbp of the present disclosure comprises a first amino acid substitution within the N-terminal domain; and a second amino acid substitution within the N-terminal domain. In some cases, a variant fHbp of the present disclosure comprises a first amino acid substitution within the C-terminal domain; and a second amino acid substitution within the C-terminal domain.

For example, in some cases, a variant fHbp of the present disclosure comprises an amino acid sequence having at least 80%, at least 85%, at least 90%, at least 95%, at least 98%, or at least 99%, amino acid sequence identity to SEQ ID NO:2, where the variant fHbp binds human fH with an affinity that 50% or less (e.g., from about 50% to about 45%, from about 45% to about 35%, from about 35% to about 25%, from about 25% to about 15%, from about 15% to about 10%, from about 10% to about 5%, from about 5% to about 2%, from about 2% to about 1%, or from about 1% to about 0.1%, or less than 0.1%) of the affinity of fHbp ID 22 for human fH, where the variant induces a bactericidal antibody response to at least one strain of *N. meningitidis* in a mammalian host, and where the variant fHbp comprises: a) a substitution of isoleucine for asparagine at amino acid 115 (N115I) and b) a substitution of glycine for aspartic acid at amino acid 121 (D121G); or where the variant fHbp comprises: a) a substitution of isoleucine for asparagine at amino acid 115 (N115I) and c) a substitution of threonine for serine at amino acid 128 (S128T); or where the variant fHbp comprises: a) a substitution of isoleucine for asparagine at amino acid 115 (N115I) and d) an amino acid substitution of the valine at position 131 (V131); or where the variant fHbp comprises: a) a substitution of isoleucine for asparagine at amino acid 115 (N115I) and e) an amino acid substitution of the lysine at position 219 (K219); or where the variant fHbp comprises: a) a substitution of isoleucine for asparagine at amino acid 115 (N115I) and f) an amino acid substitution of the glycine at position 220 (G220), relative to amino acid sequence of fHbp ID 22, the numbering of the substituted residue based on the numbering of amino acid sequence of fHbp ID 1.

As additional non-limiting examples, in some cases, a variant fHbp of the present disclosure comprises an amino acid sequence having at least 80%, at least 85%, at least 90%, at least 95%, at least 98%, or at least 99%, amino acid sequence identity to SEQ ID NO:2, where the variant fHbp binds human fH with an affinity that 50% or less (e.g., from about 50% to about 45%, from about 45% to about 35%, from about 35% to about 25%, from about 25% to about 15%, from about 15% to about 10%, from about 10% to about 5%, from about 5% to about 2%, from about 2% to about 1%, or from about 1% to about 0.1%, or less than 0.1%) of the affinity of fHbp ID 22 for human fH, where the variant induces a bactericidal antibody response to at least one strain of N. meningitidis in a mammalian host, and where the variant fHbp comprises: b) a substitution of glycine for aspartic acid at amino acid 121 (D121G) and c) a substitution of threonine for serine at amino acid 128 (S128T); or where the variant fHbp comprises: b) a substitution of glycine for aspartic acid at amino acid 121 (D121G) and d) an amino acid substitution of the valine at position 131 (V131); or where the variant fHbp comprises: b) a substitution of glycine for aspartic acid at amino acid 121 (D121G) and e) an amino acid substitution of the lysine at position 219 (K219); or where the variant fHbp comprises: b) a substitution of glycine for aspartic acid at amino acid 121 (D121G) and f) an amino acid substitution of the glycine at position 220 (G220), relative to amino acid sequence of fHbp ID 22. The numbering of the substituted residue(s) is based on the numbering of amino acid sequence of fHbp ID 1.

As additional non-limiting examples, in some cases, a variant fHbp of the present disclosure comprises an amino acid sequence having at least 80%, at least 85%, at least 90%, at least 95%, at least 98%, or at least 99%, amino acid sequence identity to SEQ ID NO:2, where the variant fHbp binds human fH with an affinity that 50% or less (e.g., from about 50% to about 45%, from about 45% to about 35%, from about 35% to about 25%, from about 25% to about 15%, from about 15% to about 10%, from about 10% to about 5%, from about 5% to about 2%, from about 2% to about 1%, or from about 1% to about 0.1%, or less than 0.1%) of the affinity of fHbp ID 22 for human fH, where the variant induces a bactericidal antibody response to at least one strain of N. meningitidis in a mammalian host, and where the variant fHbp comprises: c) a substitution of threonine for serine at amino acid 128 (S128T) and d) an amino acid substitution of the valine at position 131 (V131); or where the variant fHbp comprises: c) a substitution of threonine for serine at amino acid 128 (S128T) and e) an amino acid substitution of the lysine at position 219 (K219); or where the variant fHbp comprises: c) a substitution of threonine for serine at amino acid 128 (S128T) and f) an amino acid substitution of the glycine at position 220 (G220); or where the variant fHbp comprises: d) an amino acid substitution of the valine at position 131 (V131) and e) an amino acid substitution of the lysine at position 219 (K219); or where the variant fHbp comprises: d) an amino acid substitution of the valine at position 131 (V131) and f) an amino acid substitution of the glycine at position 220 (G220); or where the variant fHbp comprises: e) an amino acid substitution of the lysine at position 219 (K219) and f) an amino acid substitution of the glycine at position 220 (G220)), relative to amino acid sequence of fHbp ID 22. The numbering of the substituted residue(s) is based on the numbering of amino acid sequence of fHbp ID 1.

Combinations of substitutions may be included wherein the two substitutions are in different structural domains, and each independently decreases binding of fH to fHbp (e.g. one from the N-terminal domain (e.g., N115I, D121G, S128T or V131D) in combination with one from the C-terminal domain (e.g., D211A, K219N, G220S).

For example, in some cases, a variant fHbp of the present disclosure comprises an amino acid sequence having at least 80%, at least 85%, at least 90%, at least 95%, at least 98%, or at least 99%, amino acid sequence identity to SEQ ID NO:2, where the variant fHbp binds human fH with an affinity that 50% or less (e.g., from about 50% to about 45%, from about 45% to about 35%, from about 35% to about 25%, from about 25% to about 15%, from about 15% to about 10%, from about 10% to about 5%, from about 5% to about 2%, from about 2% to about 1%, or from about 1% to about 0.1%, or less than 0.1%) of the affinity of fHbp ID 22 for human fH, where the variant induces a bactericidal antibody response to at least one strain of N. meningitidis in a mammalian host, and where the variant fHbp comprises: i) an N115I substitution; and ii) a D211A substitution.

As another example, in some cases, a variant fHbp of the present disclosure comprises an amino acid sequence having at least 80%, at least 85%, at least 90%, at least 95%, at least 98%, or at least 99%, amino acid sequence identity to SEQ ID NO:2, where the variant fHbp binds human fH with an affinity that 50% or less (e.g., from about 50% to about 45%, from about 45% to about 35%, from about 35% to about 25%, from about 25% to about 15%, from about 15% to about 10%, from about 10% to about 5%, from about 5% to about 2%, from about 2% to about 1%, or from about 1% to about 0.1%, or less than 0.1%) of the affinity of fHbp ID 22 for human fH, where the variant induces a bactericidal antibody response to at least one strain of N. meningitidis in a mammalian host, and where the variant fHbp comprises: i) an N115I substitution; and ii) a K219N substitution.

As another example, in some cases, a variant fHbp of the present disclosure comprises an amino acid sequence having at least 80%, at least 85%, at least 90%, at least 95%, at least 98%, or at least 99%, amino acid sequence identity to SEQ ID NO:2, where the variant fHbp binds human fH with an affinity that 50% or less (e.g., from about 50% to about 45%, from about 45% to about 35%, from about 35% to about 25%, from about 25% to about 15%, from about 15% to about 10%, from about 10% to about 5%, from about 5% to about 2%, from about 2% to about 1%, or from about 1% to about 0.1%, or less than 0.1%) of the affinity of fHbp ID 22 for human fH, where the variant induces a bactericidal antibody response to at least one strain of N. meningitidis in a mammalian host, and where the variant fHbp comprises: i) an N115I substitution; and ii) a G220S substitution.

Also disclosed herein are variant fHbp polypeptides that have increased thermal stability compared to wild type fHbp ID22. In some cases, the variant fHbp may include the substitutions L130R and G133D relative to fHbp ID 22 (SEQ ID NO:2), wherein the variant fHbp comprises an amino acid sequence having greater than 85% amino acid sequence identity to SEQ ID NO:2, wherein the variant fHbp binds human factor H (fH) with an affinity that is 50% or less of the affinity of fHbp ID 22 for human fH, wherein the variant induces a bactericidal antibody response in a mammalian host, and the variant has a higher thermal stability that WT fHbp ID 22. The thermal stability of the variant fHbp may be higher than a WT fHbp (e.g., fHbp ID 22) by at least 5° C., 10° C., 15° C., 20° C., or more, e.g., higher by 5° C.-30° C., 5° C.-25° C., 5° C.-20° C., 10° C.-20° C., or 15° C.-20° C. As used herein, "thermal stability" refers to stability of a protein when exposed to higher temperature; a thermal stability variant protein maintains its conformation at a higher temperature than a wild type protein. For example, the variant fHbp, that include the double mutation that increases thermal stability compared to thermal stability of wild type (WT) fHbp, e.g., WT fHbp ID 22, may unfold at a higher temperature compared to WT fHbp. In certain cases, the N-terminal domain of the variant fHbp may unfold at a higher temperature than the N-terminal domain of the WT fHbp (e.g., fHbp ID 22).

In certain embodiments, a variant of factor H binding protein (fHbp) is disclosed, wherein the variant comprises amino acid substitutions L130R and G133D and at least one of the substitutions: R80A, N115I, D121G, S128T, V131, D211A, E218A, K219 (e.g., K219N), G220 (e.g., G220S), E248A, G236I, T221A, and H223A relative to fHbp ID 22 (SEQ ID NO:2), wherein the variant comprises an amino acid sequence having greater than 85% amino acid sequence identity to SEQ ID NO:2, wherein the variant fHbp binds human factor H (fH) with an affinity that is 50% or less of the affinity of fHbp ID 22 for human fH, and wherein the variant induces a bactericidal antibody response in a mammalian host.

In some cases, the variant fHbp may include a combination of substitutions, such as, L130R, G133D, and at least one amino acid substitution selected from: a) N115I; b) D121G; c) S128T; d) V131D; e) K219 (e.g., K219N); and f) G220 (e.g., G220S), wherein the amino acid substitutions are relative to fHbp ID 22 (SEQ ID NO:2), wherein the variant fHbp comprises an amino acid sequence having greater than 85% amino acid sequence identity to SEQ ID NO:2, wherein the variant fHbp binds human factor H (fH) with an affinity that is 50% or less of the affinity of fHbp ID 22 for human fH, and wherein the variant induces a bactericidal antibody response in a mammalian host.

In certain embodiments, a variant of factor H binding protein (fHbp) is disclosed, wherein the variant comprises amino acid substitutions L130R and G133D and at least one of the substitutions: R80A, D211A, E218A, E248A, G236I, T221A, and H223A relative to fHbp ID 22 (SEQ ID NO:2), wherein the variant comprises an amino acid sequence having greater than 85% amino acid sequence identity to SEQ ID NO:2, wherein the variant fHbp binds human factor H (fH) with an affinity that is 50% or less of the affinity of fHbp ID 22 for human fH, and wherein the variant induces a bactericidal antibody response in a mammalian host.

Exemplary variant fHbp include a polypeptide having an amino acid sequence having greater than 85% amino acid sequence identity (e.g., at least 90% identity, at least 95%, at least 96% identity, at least 97% identity, at least 98% identity, at least 99% identity to SEQ ID NO:2, and including the following substitutions relative to the amino acid sequence of SEQ ID NO:2: L130R and G133D; L130R, G133D, and K219N; or L130R, G133D, and G220S.

Also disclosed herein are variant fHbp proteins that include one or more substitutions relative to amino acid sequence of fHbp ID 22 as set forth above and further include the substitutions disclosed in US2011/0256180, which is herein incorporated by reference in its entirety.

Variants of fHbp ID 55

A "reference fHbp" from which a variant fHbp of the present disclosure is derived is in some cases fHbp ID 55. The amino acid sequence of fHbp ID 55 is set out below.

fHbp ID 55:

(SEQ ID NO: 3)
CSSGGGGSGGGGVTADIGTGLADALTAPLDHKDKGLKSLTLEDSISQNGT

LTLSAQGAEKTYGNGDSLNTGKLKNDKVSRFDFIRQIEVDGQLITLESGE

FQVYKQSHSALTALQTEQEQDPEHSEKMVAKRRFRIGDIAGEHTSFDKLP

KDVMATYRGTAFGSDDAGGKLTYTIDFAAKQGHGKIEHLKSPELNVDLAV

AYIKPDEKHHAVISGSVLYNQDEKGSYSLGIFGEKAQEVAGSAEVETANG

IHHIGLAAKQ.

In some cases, a variant fHbp of the present disclosure is a variant group 1 fHbp. In some cases, a variant fHbp of the present disclosure is a variant group 1 fHbp, and is a modular group IV fHbp.

In some cases, a variant fHbp of the present disclosure comprises an amino acid sequence having at least 80%, at least 85%, at least 90%, at least 95%, at least 98%, or at least 99%, amino acid sequence identity to SEQ ID NO:3; where the variant fHbp comprises one or more amino acid substitutions relative to fHbp ID 55 such that the variant fHbp exhibits an affinity for human fH that is 85% or less of the binding affinity of fHbp ID 55 for human fH, e.g., the variant fHbp exhibits an affinity for human fH that is from about 85% to about 75%, from about 75% to about 65%, from about 65% to about 55%, from about 55% to about 45%, from about 45% to about 35%, from about 35% to about 25%, from about 25% to about 15%, from about 15% to about 10%, from about 10% to about 5%, from about 5% to about 2%, from about 2% to about 1%, or from about 1% to about 0.1%, or less than 0.1%, of the binding affinity of the affinity of fHbp ID 55 for human fH; and the variant fHbp induces a bactericidal immune response to at least one strain of N. meningitidis when administered to a mammalian host (e.g., a human; or a non-human animal model).

In some cases, a variant fHbp of the present disclosure comprises an amino acid sequence having at least 80%, at least 85%, at least 90%, at least 95%, at least 98%, or at least 99%, amino acid sequence identity to SEQ ID NO:3, where the variant fHbp binds human fH with an affinity that 50% or less (e.g., from about 50% to about 45%, from about 45% to about 35%, from about 35% to about 25%, from about 25% to about 15%, from about 15% to about 10%, from about 10% to about 5%, from about 5% to about 2%, from about 2% to about 1%, or from about 1% to about 0.1%, or less than 0.1%) of the affinity of fHbp ID 55 for human fH, where the variant induces a bactericidal antibody response to at least one strain of N. meningitidis in a mammalian host, and where the variant fHbp comprises an amino acid substitution selected from at least one of: a) an amino acid substitution of the glutamic acid at position 92 (E92); b) an amino acid substitution of the serine at position 223 (S223); and c) an amino acid substitution of the histidine at position 248 (H248), relative to the amino acid sequence of fHbp ID 55, where the numbering of the amino acid residues is based on the numbering of fHbp ID 1.

In some cases, a variant fHbp of the present disclosure comprises an amino acid sequence having at least 80%, at least 85%, at least 90%, at least 95%, at least 98%, or at least 99%, amino acid sequence identity to SEQ ID NO:3, where the variant fHbp binds human fH with an affinity that 50% or less (e.g., from about 50% to about 45%, from about 45% to about 35%, from about 35% to about 25%, from about 25% to about 15%, from about 15% to about 10%, from about 10% to about 5%, from about 5% to about 2%, from about 2% to about 1%, or from about 1% to about 0.1%, or less than 0.1%) of the affinity of fHbp ID 55 for human fH, where the variant induces a bactericidal antibody response to at least one strain of *N. meningitidis* in a mammalian host, and where the variant fHbp comprises an amino acid substitution of the glutamic acid at position 92 (E92). In some cases, the fHbp variant comprises an E92K substitution. Other amino acids with positively charged or aromatic side chains, such as arginine, histidine, phenylalanine, tyrosine or tryptophan, also may be substituted at this position. Thus, for example, in some cases, the fHbp variant comprises an E92R substitution, an E92H substitution, an E92F substitution, an E92Y substitution, or an E92W substitution. As one example, a variant fHbp of the present disclosure can comprise the amino acid sequence depicted in FIG. 31 and set forth in SEQ ID NO:16.

In some cases, a variant fHbp of the present disclosure comprises an amino acid sequence having at least 80%, at least 85%, at least 90%, at least 95%, at least 98%, or at least 99%, amino acid sequence identity to SEQ ID NO:3, where the variant fHbp binds human fH with an affinity that 50% or less (e.g., from about 50% to about 45%, from about 45% to about 35%, from about 35% to about 25%, from about 25% to about 15%, from about 15% to about 10%, from about 10% to about 5%, from about 5% to about 2%, from about 2% to about 1%, or from about 1% to about 0.1%, or less than 0.1%) of the affinity of fHbp ID 55 for human fH, where the variant induces a bactericidal antibody response to at least one strain of *N. meningitidis* in a mammalian host, and where the variant fHbp comprises an amino acid substitution of the serine at position 223 (S223). In some cases, the fHbp variant comprises an S223R substitution. Other amino acids with positively charged or aromatic side chains, such as lysine, histidine, phenylalanine, tyrosine or tryptophan, also may be substituted at this position. Thus, for example, in some cases, the fHbp variant comprises an S223K substitution, an S223H substitution, an S223F substitution, an S223Y substitution, or an S223W substitution. As one example, a variant fHbp of the present disclosure can comprise the amino acid sequence depicted in FIG. 32 and set forth in SEQ ID NO:17.

In some cases, a variant fHbp of the present disclosure comprises an amino acid sequence having at least 80%, at least 85%, at least 90%, at least 95%, at least 98%, or at least 99%, amino acid sequence identity to SEQ ID NO:3, where the variant fHbp binds human fH with an affinity that 50% or less (e.g., from about 50% to about 45%, from about 45% to about 35%, from about 35% to about 25%, from about 25% to about 15%, from about 15% to about 10%, from about 10% to about 5%, from about 5% to about 2%, from about 2% to about 1%, or from about 1% to about 0.1%, or less than 0.1%) of the affinity of fHbp ID 55 for human fH, where the variant induces a bactericidal antibody response to at least one strain of *N. meningitidis* in a mammalian host, and where the variant fHbp comprises an amino acid substitution of the histidine at position 248 (H248). In some cases, the fHbp variant comprises an H248L substitution. Other amino acids with non-polar, negatively charged or aromatic side chains, such as isoleucine, valine, aspartate, glutamate, phenylalanine, tyrosine or tryptophan, also may be substituted at this position. Thus, for example, in some cases, the fHbp variant comprises an H248I substitution, an H248V substitution, an H248D substitution, an H248E substitution, an H248F substitution, an H248Y substitution, or an H248W substitution. As one example, a variant fHbp of the present disclosure can comprise the amino acid sequence depicted in FIG. 33 and set forth in SEQ ID NO:18.

Combinations of Amino Acid Substitutions

In some cases, a variant fHbp of the present disclosure comprises an amino acid sequence having at least 80%, at least 85%, at least 90%, at least 95%, at least 98%, or at least 99%, amino acid sequence identity to SEQ ID NO:3, where the variant fHbp binds human fH with an affinity that 50% or less (e.g., from about 50% to about 45%, from about 45% to about 35%, from about 35% to about 25%, from about 25% to about 15%, from about 15% to about 10%, from about 10% to about 5%, from about 5% to about 2%, from about 2% to about 1%, or from about 1% to about 0.1%, or less than 0.1%) of the affinity of fHbp ID 55 for human fH, where the variant induces a bactericidal antibody response to at least one strain of *N. meningitidis* in a mammalian host, and where the variant fHbp comprises two or more amino acid substitutions selected from the group consisting of: a) an amino acid substitution of the glutamic acid at position 92 (E92); b) an amino acid substitution of the serine at position 223 (S223); and c) an amino acid substitution of the histidine at position 248 (H248), relative to fHbp ID 55, where the numbering of the residue is based on the numbering of amino acids in the sequence for fHbp ID 1.

Combinations of substitutions may be included wherein the two substitutions are in different structural domains, and each independently decreases binding of fH to fHbp (e.g., one substitution in the N-terminal domain, in combination with an amino acid substitution in the C-terminal domain. In some cases, a variant fHbp of the present disclosure comprises a first amino acid substitution within the N-terminal domain; and a second amino acid substitution within the C-terminal domain. In some cases, a variant fHbp of the present disclosure comprises a first amino acid substitution within the N-terminal domain; and a second amino acid substitution within the N-terminal domain. In some cases, a variant fHbp of the present disclosure comprises a first amino acid substitution within the C-terminal domain; and a second amino acid substitution within the C-terminal domain.

For example, in some cases, a variant fHbp of the present disclosure comprises an amino acid sequence having at least 80%, at least 85%, at least 90%, at least 95%, at least 98%, or at least 99%, amino acid sequence identity to SEQ ID NO:3, where the variant fHbp binds human fH with an affinity that 50% or less (e.g., from about 50% to about 45%, from about 45% to about 35%, from about 35% to about 25%, from about 25% to about 15%, from about 15% to about 10%, from about 10% to about 5%, from about 5% to about 2%, from about 2% to about 1%, or from about 1% to about 0.1%, or less than 0.1%) of the affinity of fHbp ID 55 for human fH, where the variant induces a bactericidal antibody response to at least one strain of *N. meningitidis* in a mammalian host, and where the variant fHbp comprises: a) an amino acid substitution of the glutamic acid at position 92 (E92) and b) an amino acid substitution of the serine at position 223 (S223); or where the variant fHbp comprises: a) an amino acid substitution of the glutamic acid at position 92 (E92) and c) an amino acid substitution of the histidine at position 248 (H248); or where the variant fHbp comprises: b) an amino acid substitution of the serine at position 223 (S223) and c) an amino acid substitution of the histidine at position 248 (H248); or where the variant fHbp comprises: a) an amino acid substitution of the glutamic acid at position 92 (E92) and b) an amino acid substitution of the serine at position 223 (S223) and c) an amino acid substitution of the histidine at position 248 (H248), relative to fHbp ID 55, where the numbering of the residue is based on the numbering of amino acids in the sequence for fHbp ID 1.

Also disclosed herein are variant fHbp proteins that include one or more substitutions relative to amino acid sequence of fHbp ID 55 as set forth above and further include the substitutions disclosed in US2011/0256180, which is herein incorporated by reference in its entirety.

Fusion Polypeptides

A variant fHbp of the present disclosure can be a fusion polypeptide, e.g., a polypeptide comprising a variant fHbp as described above, and a heterologous polypeptide (e.g., a fusion partner). The fusion partner can be at the N-terminus of the variant fHbp, at the C-terminus of the variant fHbp, or at an internal site within the fHbp.

Suitable fusion partners include peptides and polypeptides that confer enhanced stability in vivo (e.g., enhanced serum half-life); provide ease of purification, e.g., (His)$_n$, e.g., 6His, and the like; provide for secretion of the fusion protein from a cell; provide an epitope tag, e.g., GST, hemagglutinin (HA; e.g., YPYDVPDYA; SEQ ID NO:26), FLAG (e.g., DYKDDDDK; SEQ ID NO:27), c-myc (e.g., EQKLISEEDL; SEQ ID NO:28), and the like; provide a detectable signal, e.g., an enzyme that generates a detectable product (e.g., β-galactosidase, luciferase), or a protein that is itself detectable, e.g., a green fluorescent protein, a yellow fluorescent protein, etc.; provides for multimerization, e.g., a multimerization domain such as an Fc portion of an immunoglobulin; and the like.

Methods of Production

The fHbps of the present disclosure can be produced by any suitable method, including recombinant and non-recombinant methods (e.g., chemical synthesis). Where the subject fHbp is produced using recombinant techniques, the methods can involve any suitable construct and any suitable host cell, which can be a prokaryotic or eukaryotic cell, usually a bacterial or yeast host cell, more usually a bacterial cell. Methods for introduction of genetic material into host cells include, for example, transformation, electroporation, conjugation, calcium phosphate methods and the like. The method for transfer can be selected so as to provide for stable expression of the introduced fHbp-encoding nucleic acid. The fHbp-encoding nucleic acid can be provided as an inheritable episomal element (e.g., plasmid) or can be genomically integrated.

The present disclosure provides nucleic acids (including isolated nucleic acids) that comprise a nucleotide sequence encoding a fHbp variant of the present disclosure. In some embodiments, the nucleotide sequence encoding the fHbp variant is operably linked to a transcriptional control element, e.g., a promoter. The promoter is in some cases constitutive. The promoter is in some cases inducible. In some cases, the promoter is suitable for use (e.g., active in) a prokaryotic host cell. In some cases, the promoter is suitable for use (e.g., active in) a eukaryotic host cell.

In some instances, a nucleic acid comprising a nucleotide sequence encoding a fHbp variant of the present disclosure is present in an expression vector. The present disclosure provides a recombinant expression vector (e.g., an isolated recombinant expression vector) that comprises a nucleotide sequence encoding a fHbp variant of the present disclosure In some embodiments, the nucleotide sequence encoding the fHbp variant is operably linked to a transcriptional control element, e.g., a promoter. The promoter is in some cases constitutive. The promoter is in some cases inducible. In some cases, the promoter is suitable for use (e.g., active in) a prokaryotic host cell. In some cases, the promoter is suitable for use (e.g., active in) a eukaryotic host cell.

Suitable vectors for transferring fHbp-encoding nucleic acid can vary in composition. Integrative vectors can be conditionally replicative or suicide plasmids, bacteriophages, and the like. The constructs can include various elements, including for example, promoters, selectable genetic markers (e.g., genes conferring resistance to antibiotics (for instance kanamycin, erythromycin, chloramphenicol, or gentamycin)), origin of replication (to promote replication in a host cell, e.g., a bacterial host cell), and the like. The choice of vector will depend upon a variety of factors such as the type of cell in which propagation is desired and the purpose of propagation. Certain vectors are useful for amplifying and making large amounts of the desired DNA sequence. Other vectors are suitable for expression in cells in culture. Still other vectors are suitable for transfer and expression in cells in a whole animal. The choice of appropriate vector is well within the skill of the art. Many such vectors are available commercially.

In one example, the vector is an expression vector based on episomal plasmids containing selectable drug resistance markers and elements that provide for autonomous replication in different host cells (e.g., in both *E. coli* and *N. meningitidis*). One example of such a "shuttle vector" is the plasmid pFP10 (Pagotto et al. (2000) Gene 244:13-19).

Constructs (recombinant vectors) can be prepared by, for example, inserting a polynucleotide of interest into a construct backbone, typically by means of DNA ligase attachment to a cleaved restriction enzyme site in the vector. Alternatively, the desired nucleotide sequence can be inserted by homologous recombination or site-specific recombination. Typically homologous recombination is accomplished by attaching regions of homology to the vector on the flanks of the desired nucleotide sequence, while site-specific recombination can be accomplished through use of sequences that facilitate site-specific recombination (e.g., cre-lox, att sites, etc.). Nucleic acid containing such sequences can be added by, for example, ligation of oligonucleotides, or by polymerase chain reaction using primers comprising both the region of homology and a portion of the desired nucleotide sequence.

Vectors can provide for extrachromosomal maintenance in a host cell or can provide for integration into the host cell genome. Vectors are amply described in numerous publications well known to those in the art, including, e.g., Short Protocols in Molecular Biology, (1999) F. Ausubel, et al., eds., Wiley & Sons. Vectors may provide for expression of the nucleic acids encoding the subject fHbp, may provide for propagating the subject nucleic acids, or both.

Examples of vectors that may be used include but are not limited to those derived from recombinant bacteriophage DNA, plasmid DNA or cosmid DNA. For example, plasmid vectors such as pBR322, pUC 19/18, pUC 118, 119 and the M13 mp series of vectors may be used. pET21 is also an expression vector that may be used. Bacteriophage vectors may include λgt10, λgt11, λgt18-23, λZAP/R and the EMBL series of bacteriophage vectors. Further vectors that may be utilized include, but are not limited to, pJB8, pCV 103, pCV 107, pCV 108, pTM, pMCS, pNNL, pHSG274, COS202, COS203, pWE15, pWE16 and the charomid 9 series of vectors.

For expression of a subject fHbp, an expression cassette may be employed. Thus, the present disclosure provides a recombinant expression vector comprising a subject nucleic acid. The expression vector provides transcriptional and translational regulatory sequences, and may provide for inducible or constitutive expression, where the coding region is operably linked under the transcriptional control of the transcriptional initiation region, and a transcriptional and translational termination region. These control regions may be native to an fHbp from which the subject fHbp is derived, or may be derived from exogenous sources. In general, the transcriptional and translational regulatory sequences may include, but are not limited to, promoter sequences, ribosomal binding sites, transcriptional start and stop sequences, translational start and stop sequences, and enhancer or activator sequences. Promoters can be either constitutive or inducible, and can be a strong constitutive promoter (e.g., T7, and the like).

Expression vectors generally have convenient restriction sites located near the promoter sequence to provide for the insertion of nucleic acid sequences encoding proteins of interest. A selectable marker operative in the expression host may be present to facilitate selection of cells containing the vector. In addition, the expression construct may include additional elements. For example, the expression vector may have one or two replication systems, thus allowing it to be maintained in organisms, for example in mammalian or insect cells for expression and in a prokaryotic host for cloning and amplification. In addition the expression construct may contain a selectable marker gene to allow the selection of transformed host cells. Selection genes are well known in the art and will vary with the host cell used.

It should be noted that fHbps of the present disclosure may comprise additional elements, such as a detectable label, e.g., a radioactive label, a fluorescent label, a biotin label, an immunologically detectable label (e.g., a hemagglutinin tag, a poly-Histidine tag) and the like. Additional elements of fHbp can be provided to facilitate isolation (e.g., biotin tag, immunologically detectable tag) through various methods (e.g., affinity capture, etc.). The subject fHbp can optionally be immobilized on a support through covalent or non-covalent attachment.

Isolation and purification of fHbp can be accomplished according to methods known in the art. For example, fHbp can be isolated from a lysate of cells genetically modified to express a fHbp, or from a synthetic reaction mix, by immunoaffinity purification, which generally involves contacting the sample with an anti-fHbp antibody (e.g., an anti-fHbp monoclonal antibody (mAb), such as a JAR 4 MAb or other appropriate JAR MAb known in the art), washing to remove non-specifically bound material, and eluting specifically bound fHbp. Isolated fHbp can be further purified by dialysis and other methods normally employed in protein purification methods. In one example, the fHbp can be isolated using metal chelate chromatography methods.

Host Cells

Any of a number of suitable host cells can be used in the production of fHbp. In general, the fHbp described herein may be expressed in prokaryotes or eukaryotes, e.g., bacteria such as *Escherichia coli* or *Neisseria* (e.g., *N. meningitidis*) in accordance with conventional techniques. Thus, the present disclosure further provides a genetically modified in vitro host cell, which contains a nucleic acid encoding a subject fHbp. Host cells for production (including large scale production) of a subject fHbp can be selected from any of a variety of available host cells. Examples of host cells for expression include those of a prokaryotic or eukaryotic unicellular organism, such as bacteria (e.g., *Escherichia coli* strains), yeast (e.g., *Saccharomyces cerevisiae, Pichia* spp., and the like), and may include host cells originally derived from a higher organism such as insects, vertebrates, e.g., mammals. Suitable mammalian cell lines include, but are not limited to, HeLa cells (e.g., American Type Culture Collection (ATCC) No. CCL-2), CHO cells (e.g., ATCC Nos. CRL9618, CCL61, CRL9096), 293 cells (e.g., ATCC No. CRL-1573), Vero cells, NIH 3T3 cells (e.g., ATCC No. CRL-1658), Huh-7 cells, BHK cells (e.g., ATCC No. CCL10), PC12 cells (ATCC No. CRL1721), COS cells, COS-7 cells (ATCC No. CRL1651), RAT1 cells, mouse L cells (ATCC No. CCLI.3), human embryonic kidney (HEK) cells (ATCC No. CRL1573), HLHepG2 cells, and the like). In some cases, bacterial host cells and yeast host cells are of particular interest for subject fHbp production.

Subject fHbps can be prepared in substantially pure or substantially isolated form (i.e., substantially free from other Neisserial or host cell polypeptides) or substantially isolated form. The subject fHbp can be present in a composition that is enriched for the polypeptide relative to other components that may be present (e.g., other polypeptides or other host cell components). Purified subject fHbp can be provided such that the polypeptide is present in a composition that is substantially free of other expressed polypeptides, e.g., less than 90%, usually less than 60% and more usually less than 50% of the composition is made up of other expressed polypeptides.

Host Cells for Vesicle Production

Where a subject fHbp is to be provided in a membrane vesicle (as discussed in more detail below), a Neisserial host cell is genetically modified to express a subject fHbp. Any of a variety of *Neisseria* spp. strains can be modified to produce a subject fHbp, and, optionally, which produce or can be modified to produce other antigens of interest, such as PorA, can be used in the methods disclosed herein.

Methods and vectors to provide for genetic modification of Neisserial strains and expression of a desired polypeptide are known in the art. Examples of vectors and methods can be found in WO 02/09746 and O'Dwyer et al. (2004) Infect Immun 72:6511-80. Strong promoters, particularly constitutive strong promoters are of particular interest. Examples of promoters include the promoters of porA, porB, lbpB, tbpB, p110, hpuAB, lgtF, opa, p110, lst, hpuAB, and rmp.

Pathogenic *Neisseria* spp. or strains derived from pathogenic *Neisseria* spp., particularly strains pathogenic for humans or derived from strains pathogenic or commensal for humans, are of particular interest for use in membrane vesicle production. Examples of Neisserial spp. include *N. meningitidis, N. flavescens, N. gonorrhoeae, N. lactamica, N. polysaccharea, N. cinerea, N. mucosa, N. subflava, N. sicca, N. elongata*, and the like.

*N. meningitidis* strains are of particular interest for genetic modification to express the subject fHbps and for use in vesicle production. The strain used for vesicle production can be selected according to a number of different characteristics that may be desired. For example, the strain may be selected according to: a desired PorA type (a "serosubtype"), capsular group, serotype, and the like; decreased capsular polysaccharide production; and the like. For example, the production strain can produce any desired PorA polypeptide, and may express one or more PorA polypeptides (either naturally or due to genetic engineering). Examples of strains include those that produce a PorA polypeptide which confers a serosubtype of P1.7,16; P1.19,15; P1.7,1; P1.5,2; P1.22a, 14; P1.14; P1.5,10; P1.7,4; P1.12,13; as well as variants of such PorA polypeptides which may or may not retain reactivity with conventional serologic reagents used in serosubtyping. Also of interest are PorA polypeptides characterized according to PorA variable region (VR) typing (see, e.g., Russell et al. (2004) Emerging Infect Dis 10:674-678; Sacchi C T et al. (1998) Clin Diagn Lab Immunol 5:845-55;

Sacchi et al (2000) J. Infect Dis 182:1169-1176). A substantial number of distinct VR types have been identified, which can be classified into VR1 and VR2 family "prototypes". A web-accessible database describing this nomenclature and its relationship to previous typing schemes is found at neisseria.org/nm/typing/pora. Alignments of certain PorA VR1 and VR2 types are provided in Russell et al. (2004) Emerging Infect Dis 10:674-678.

Alternatively or in addition, the production strain can be a capsule deficient strain. Capsule deficient strains can provide vesicle-based vaccines that provide for a reduced risk of eliciting a significant autoantibody response in a subject to whom the vaccine is administered (e.g., due to production of antibodies that cross-react with sialic acid on host cell surfaces). "Capsule deficient" or "deficient in capsular polysaccharide" as used herein refers to a level of capsular polysaccharide on the bacterial surface that is lower than that of a naturally-occurring strain or, where the strain is genetically modified, is lower than that of a parental strain from which the capsule deficient strain is derived. A capsule deficient strain includes strains that are decreased in surface capsular polysaccharide production by at least 10%, 20%, 25%, 30%, 40%, 50%, 60%, 75%, 80%, 85%, 90% or more, and includes strains in which capsular polysaccharide is not detectable on the bacterial surface (e.g., by whole cell enzyme-linked immunosorbent assay (ELISA) using an anti-capsular polysaccharide antibody).

Capsule deficient strains include those that are capsule deficient due to a naturally-occurring or recombinantly-generated genetic modification. Naturally-occurring capsule deficient strains (see, e.g., Dolan-Livengood et al. (2003) J. Infect. Dis. 187:1616-28), as well as methods of identifying and/or generating capsule-deficient strains (see, e.g., Fisseha et al. (2005) Infect. Immun. 73:4070-4080; Stephens et al. (1991) Infect Immun 59:4097-102; Frosch et al. (1990) Mol Microbiol. 4:1215-1218) are known in the art.

Modification of a Neisserial host cell to provide for decreased production of capsular polysaccharide may include modification of one or more genes involved in capsule synthesis, where the modification provides for, for example, decreased levels of capsular polysaccharide relative to a parent cell prior to modification. Such genetic modifications can include changes in nucleotide and/or amino acid sequences in one or more capsule biosynthesis genes rendering the strain capsule deficient (e.g., due to one or more insertions, deletions, substitutions, and the like in one or more capsule biosynthesis genes). Capsule deficient strains can lack or be non-functional for one or more capsule genes.

Of particular interest are strains that are deficient in sialic acid biosynthesis. Such strains can provide for production of vesicles that have reduced risk of eliciting anti-sialic acid antibodies that cross-react with human sialic acid antigens, and can further provide for improved manufacturing safety. Strains having a defect in sialic acid biosynthesis (due to either a naturally occurring modification or an engineered modification) can be defective in any of a number of different genes in the sialic acid biosynthetic pathway. Of particular interest are strains that are defective in a gene product encoded by the N-acetylglucosamine-6-phosphate 2-epimerase gene (known as synX AAF40537.1 or siaA AAA20475), with strains having this gene inactivated being of especial interest. For example, in one embodiment, a capsule deficient strain is generated by disrupting production of a functional synX gene product (see, e.g., Swartley et al. (1994) J Bacteriol. 176:1530-4).

Capsule-deficient strains can also be generated from naturally-occurring strains using non-recombinant techniques, e.g., by use of bactericidal anti-capsular antibodies to select for strains with reduced levels of capsular polysaccharide.

Where the disclosure involves use of two or more strains (e.g., to produce antigenic compositions containing a subject fHbp-presenting vesicles from different strains), the strains can be selected so as to differ in one or more strain characteristics, e.g., to provide for vesicles that differ in the subject fHbp used, PorA, and the like.

Preparation of Vesicles

The antigenic compositions contemplated by the present disclosure generally include vesicles prepared from Neisserial cells that express a subject fHbp. As referred to herein "vesicles" is meant to encompass outer membrane vesicles as well as microvesicles (which are also referred to as blebs).

The antigenic composition can contain outer membrane vesicles (OMV) prepared from the outer membrane of a cultured strain of Neisseria meningitidis spp. genetically modified to express a subject fHbp. OMVs may be obtained from Neisseria meningitidis grown in broth or solid medium culture, preferably by separating the bacterial cells from the culture medium (e.g. by filtration or by a low-speed centrifugation that pellets the cells, or the like), lysing the cells (e.g. by addition of detergent, osmotic shock, sonication, cavitation, homogenization, or the like) and separating an outer membrane fraction from cytoplasmic molecules (e.g. by filtration; or by differential precipitation or aggregation of outer membranes and/or outer membrane vesicles, or by affinity separation methods using ligands that specifically recognize outer membrane molecules; or by a high-speed centrifugation that pellets outer membranes and/or outer membrane vesicles, or the like); outer membrane fractions may be used to produce OMVs.

The antigenic composition can contain microvesicles (MV) (or "blebs") containing subject fHbps, where the MV or blebs are released during culture of a Neisseria meningitidis strain genetically modified to express a subject fHbp. For example, MVs may be obtained by culturing a strain of Neisseria meningitidis in broth culture medium, separating whole cells from the broth culture medium (e.g. by filtration, or by a low-speed centrifugation that pellets only the cells and not the smaller blebs, or the like), and then collecting the MVs that are present in the cell-free culture medium (e.g. by filtration, differential precipitation or aggregation of MVs, or by a high-speed centrifugation that pellets the blebs, or the like). Strains for use in production of MVs can generally be selected on the basis of the amount of blebs produced in culture (e.g., bacteria can be cultured in a reasonable number to provide for production of blebs suitable for isolation and administration in the methods described herein). An exemplary strain that produces high levels of blebs is described in PCT Publication No. WO 01/34642. In addition to bleb production, strains for use in MV production may also be selected on the basis of NspA production, where strains that produce higher levels of NspA may be of particular interest (for examples of N. meningitidis strains having different NspA production levels, see, e.g., Moe et al. (1999 Infect. Immun 67: 5664). Other strains of interest for use in production of blebs include strains having an inactivated GNA33 gene, which encodes a lipoprotein required for cell separation, membrane architecture and virulence (see, e.g., Adu-Bobie et al. (2004) Infect Immun 72:1914-1919).

The antigenic compositions of the present disclosure can contain vesicles from one strain, or from 2, 3, 4, 5 or more strains, which strains may be homologous or heterologous, usually heterologous, to one another. For example, the strains may be homologous or heterologous with respect to PorA and/or the fHbp from which the subject fHbp is derived. The vesicles can be prepared from strains that express more than one subject fHbp (e.g., 1, 2, 3, or more subject fHbp) which may be composed of fHbp amino acid sequences from different variants (v.1, v.2, or v.3) or subvariants (e.g., a subvariant of v.1, v.2, or v.3).

The antigenic compositions can comprise a mixture of OMVs and MVs presenting the same or different subject fHbps, where the subject fHbps may optionally present epitopes from different combinations of fHbp variants and/or subvariants and where the OMVs and/or MVs may be from the same or different strains. Vesicles from different strains can be administered as a mixture, or can be administered serially.

Where desired (e.g., where the strains used to produce vesicles are associated with endotoxin or particular high levels of endotoxin), the vesicles are optionally treated to reduce endotoxin, e.g., to reduce toxicity following administration. Although less desirable as discussed below, reduction of endotoxin can be accomplished by extraction with a suitable detergent (for example, BRIJ-96, sodium deoxycholate, sodium lauroylsarcosinate, EMPIGEN BB, TRITON X-100, non-ionic detergent TWEEN 20 (sorbitan monolaurate polyoxyethylene), non-ionic detergent TWEEN 80, at a concentration of 0.1-10%, e.g., 0.5-2%, and sodium dodecyl sulfate (SDS)). Where detergent extraction is used, it is preferable to use a detergent other than deoxycholate.

The vesicles of the antigenic compositions can be prepared without detergent, e.g., without use of deoxycholate. Although detergent treatment is useful to remove endotoxin activity, it may deplete the native fHbp lipoprotein and/or subject fHbp (including lipidated fHbp) by extraction during vesicle production. Thus it may be particularly desirable to decrease endotoxin activity using technology that does not require a detergent. In one approach, strains that are relatively low producers of endotoxin (lipopolysaccharide, LPS) are used so as to avoid the need to remove endotoxin from the final preparation prior to use in humans. For example, the vesicles can be prepared from Neisseria mutants in which lipooligosaccharide or other antigens that may be undesirable in a vaccine (e.g. Rmp) is reduced or eliminated.

Vesicles can be prepared from N. meningitidis strains that contain genetic modifications that result in decreased or no detectable toxic activity of lipid A. For example, such strain can be genetically modified in lipid A biosynthesis (Steeghs et al. (1999) Infect Immun 67:4988-93; van der Ley et al. (2001) Infect Immun 69:5981-90; Steeghs et al. (2004) J Endotoxin Res 10:113-9; Fissha et al, (2005) Infect Immun 73:4070). The immunogenic compositions may be detoxified by modification of LPS, such as downregulation and/or inactivation of the enzymes encoded by 1pxL1 or 1pxL2, respectively. Production of a penta-acylated lipid A made in 1pxL1 mutants indicates that the enzyme encoded by 1pxL1 adds the C12 to the N-linked 3-OH C14 at the 2' position of GlcN II. The major lipid A species found in 1pxL2 mutants is tetra-acylated, indicating the enzyme encoded by 1pxL2 adds the other C12, i.e., to the N-linked 3-OH C14 at the 2 position of GlcN I. Mutations resulting in a decreased (or no) expression of these genes (or decreased or no activity of the products of these genes) result in altered toxic activity of lipid A (van der Ley et al. (2001) Infect Immun 69:5981-90). Tetra-acylated (lpxL2 mutant) and penta acylated (lpxL1 mutant) lipid A are less toxic than the wild-type lipid A. Mutations in the lipid A 4'-kinase encoding gene (lpxK) also decrease the toxic activity of lipid A. Of particular interest for use in production of vesicles (e.g., MV or OMV) are *N. meningitidis* strains genetically modified so as to provide for decreased or no detectable functional LpxL1-encoded protein, e.g., where the *Neisseria bacterium* (e.g., *N. meningitidis* strain) is genetically modified to provide for decreased or no activity of a gene product of the 1pxL1 gene. For example, the *Neisseria bacterium* can be genetically modified to have an 1pxL1 gene knockout, e.g., where the 1pxL1 gene is disrupted. See, e.g., US Patent Publication No. 2009/0035328. The *Neisseria bacterium* can be genetically modified to provide for decreased or no activity of a gene product of the 1pxL2 gene. The *Neisseria bacterium* can be genetically modified to provide for decreased or no activity of a gene product of the 1pxL1 gene and the 1pxL2 gene. Such vesicles provide for reduced toxicity as compared to *N. meningitidis* strains that are wild-type for LPS production, while retaining immunogenicity of subject fHbp.

LPS toxic activity can also be altered by introducing mutations in genes/loci involved in polymyxin B resistance (such resistance has been correlated with addition of aminoarabinose on the 4' phosphate of lipid A). These genes/loci could be pmrE that encodes a UDP-glucose dehydrogenase, or a region of antimicrobial peptide-resistance genes common to many enterobacteriaciae which could be involved in aminoarabinose synthesis and transfer. The gene pmrF that is present in this region encodes a dolicol-phosphate manosyl transferase (Gunn J. S., Kheng, B. L., Krueger J., Kim K., Guo L., Hackett M., Miller S. I. 1998. Mol. Microbiol. 27: 1171-1182).

Mutations in the PhoP-PhoQ regulatory system, which is a phospho-relay two component regulatory system (e.g., PhoP constitutive phenotype, PhoPc), or low $Mg^{++}$ environmental or culture conditions (that activate the PhoP-PhoQ regulatory system) lead to the addition of aminoarabinose on the 4'-phosphate and 2-hydroxymyristate replacing myristate (hydroxylation of myristate). This modified lipid A displays reduced ability to stimulate E-selectin expression by human endothelial cells and TNF secretion from human monocytes.

Polymyxin B resistant strains are also suitable for use, as such strains have been shown to have reduced LPS toxicity (see, e.g., van der Ley et al. (1994) In: Proceedings of the ninth international pathogenic *Neisseria* conference. The Guildhall, Winchester, England). Alternatively, synthetic peptides that mimic the binding activity of polymyxin B may be added to the antigenic compositions to reduce LPS toxic activity (see, e.g., Rustici et al. (1993) Science 259: 361-365; Porro et al. (1998) Prog Clin Biol Res. 397:315-25).

Endotoxin can also be reduced through selection of culture conditions. For example, culturing the strain in a growth medium containing 0.1 mg-100 mg of aminoarabinose per liter medium provides for reduced lipid toxicity (see, e.g., WO 02/097646).

Compositions and Formulations

"Compositions", "antigen composition", "antigenic composition" or "immunogenic composition" is used herein as a matter of convenience to refer generically to compositions comprising a subject fHbp as disclosed herein, which subject fHbp may be optionally conjugated to further enhance immunogenicity. Compositions useful for eliciting antibodies, e.g., antibodies against *Neisseria meningitidis*, e.g., bactericidal antibodies to *Neisseria meningitidis*, in a human are specifically contemplated by the present disclosure. Antigenic compositions can contain 1, 2, or more different subject fHbps. Where there is more than one type of fHbp, each subject fHbps may present epitopes from different combinations of fHbp variants and/or subvariants.

Antigenic compositions contain an immunologically effective amount of a subject fHbp, and may further include other compatible components, as needed. Compositions of the present disclosure can contain fHbp that are low fH binders. The composition contain one or more fHbp, in which at least one fHbp is a low fH binder. Where there is more than one fHbp in a composition, each fHbp may be different (e.g. in amino acid sequences and/or conjugation).

In some cases, an antigenic composition of the present disclosure comprises only one fHbp variant of the present disclosure. In some cases, an antigenic composition of the present disclosure comprises two or more different fHbp variants of the present disclosure. As non-limiting examples, in some cases, an antigenic composition of the present disclosure comprises:

1) a first variant of fHbp ID 1, where the first fHbp ID 1 variant comprises an amino acid substitution at Q38 (e.g., Q38R); and a second variant of fHbp ID 1, where the second fHbp ID 1 variant comprises an amino acid substitution at E92 (e.g., E92K);

2) a first variant of fHbp ID 1, where the first fHbp ID 1 variant comprises an amino acid substitution at Q38 (e.g., Q38R); and a second variant of fHbp ID 1, where the second fHbp ID 1 variant comprises an amino acid substitution at R130 (e.g., R130G);

3) a first variant of fHbp ID 1, where the first fHbp ID 1 variant comprises an amino acid substitution at Q38 (e.g., Q38R); and a second variant of fHbp ID 1, where the second fHbp ID 1 variant comprises an amino acid substitution at 5223 (e.g., S223R);

4) a first variant of fHbp ID 1, where the first fHbp ID 1 variant comprises an amino acid substitution at Q38 (e.g., Q38R); and a second variant of fHbp ID 1, where the second fHbp ID 1 variant comprises an amino acid substitution at H248 (e.g., H248L);

5) a variant of fHbp ID 22, where the fHbp ID 22 variant comprises an amino acid substitution at N115 (e.g., N115I); and a variant of fHbp ID 1, where the fHbp ID 1 variant comprises an amino acid substitution at Q38 (e.g., Q38R);

6) a variant of fHbp ID 22, where the fHbp ID 22 variant comprises an amino acid substitution at D121 (e.g., D121G); and a variant of fHbp ID 1, where the fHbp ID 1 variant comprises an amino acid substitution at E92 (e.g., E92K);

7) a variant of fHbp ID 22, where the fHbp ID 22 variant comprises an amino acid substitution at 5128 (e.g., S128T); and a variant of fHbp ID 1, where the fHbp ID 1 variant comprises an amino acid substitution at H248 (e.g., H248L);

8) a variant of fHbp ID 22, where the fHbp ID 22 variant comprises an amino acid substitution at V131 (e.g., V131D); and a variant of fHbp ID 1, where the fHbp ID 1 variant comprises an amino acid substitution at Q38 (e.g., Q38R);

9) a variant of fHbp ID 22, where the fHbp ID 22 variant comprises an amino acid substitution at K219 (e.g., K219N); and a variant of fHbp ID 1, where the fHbp ID 1 variant comprises an amino acid substitution at Q38 (e.g., Q38R);

10) a variant of fHbp ID 22, where the fHbp ID 22 variant comprises an amino acid substitution at G220 (e.g., G220S); and a variant of fHbp ID 1, where the fHbp ID 1 variant comprises an amino acid substitution at Q38 (e.g., Q38R);

11) a variant of fHbp ID 22, where the fHbp ID 22 variant comprises an amino acid substitution at N115 (e.g., N115I); and a variant of fHbp ID 55, where the fHbp ID 55 variant comprises an amino acid substitution at E92 (e.g., E92K);

12) a variant of fHbp ID 22, where the fHbp ID 22 variant comprises an amino acid substitution at D121 (e.g., D121G); and a variant of fHbp ID 55, where the fHbp ID 55 variant comprises an amino acid substitution at 5223 (e.g., S223R);

13) a variant of fHbp ID 22, where the fHbp ID 22 variant comprises an amino acid substitution at 5128 (e.g., S128T); and a variant of fHbp ID 55, where the fHbp ID 55 variant comprises an amino acid substitution at H248 (e.g., H248L);

14) a variant of fHbp ID 22, where the fHbp ID 22 variant comprises an amino acid substitution at V131 (e.g., V131D); and a variant of fHbp ID 55, where the fHbp ID 55 variant comprises an amino acid substitution at E92 (e.g., E92K);

15) a variant of fHbp ID 22, where the fHbp ID 22 variant comprises an amino acid substitution at K219 (e.g., K219N); and a variant of fHbp ID 55, where the fHbp ID 55 variant comprises an amino acid substitution at E92 (e.g., E92K);

16) a variant of fHbp ID 22, where the fHbp ID 22 variant comprises an amino acid substitution at G220 (e.g., G220S); and a variant of fHbp ID 55, where the fHbp ID 55 variant comprises an amino acid substitution at E92 (e.g., E92K);

17) a first variant of fHbp ID 1, where the first fHbp ID 1 variant comprises an amino acid substitution at E92 (e.g., E92K); and a second variant of fHbp ID 1, where the second fHbp ID 1 variant comprises an amino acid substitution at H248 (e.g., H248L);

18) a first variant of fHbp ID 1, where the first fHbp ID 1 variant comprises an amino acid substitution at E92 (e.g., E92K); and a second variant of fHbp ID 1, where the second fHbp ID 1 variant comprises an amino acid substitution at 5223 (e.g., S223R);

19) a first variant of fHbp ID 22, where the first fHbp ID 22 variant comprises an amino acid substitution at N115 (e.g., N115I); and a second variant of fHbp ID 22, where the second fHbp ID 22 variant comprises an amino acid substitution at D211 (e.g., D211A);

20) a first variant of fHbp ID 22, where the first fHbp ID 22 variant comprises an amino acid substitution at N115 (e.g., N115I); and a second variant of fHbp ID 22, where the second fHbp ID 22 variant comprises an amino acid substitution at K219 (e.g., K219N);

21) a first variant of fHbp ID 22, where the first fHbp ID 22 variant comprises an amino acid substitution at N115 (e.g., N115I); and a second variant of fHbp ID 22, where the second fHbp ID 22 variant comprises an amino acid substitution at G220 (e.g., G220S);

22) a first variant of fHbp ID 22, where the first fHbp ID 22 variant comprises an amino acid substitution at D121 (e.g., D121G); and a second variant of fHbp ID 22, where the second fHbp ID 22 variant comprises an amino acid substitution at G220 (e.g., G220S);

23) a first variant of fHbp ID 22, where the first fHbp ID 22 variant comprises an amino acid substitution at 5128 (e.g., S128T); and a second variant of fHbp ID 22, where the second fHbp ID 22 variant comprises an amino acid substitution at G220 (e.g., G220S);

24) a first variant of fHbp ID 22, where the first fHbp ID 22 variant comprises an amino acid substitution at V131 (e.g., V131D); and a second variant of fHbp ID 22, where the second fHbp ID 22 variant comprises an amino acid substitution at G220 (e.g., G220S);

25) a first variant of fHbp ID 55, where the first fHbp ID 55 variant comprises an amino acid substitution at E92 (e.g., E92K); and a second variant of fHbp ID 55, where the second fHbp ID 55 variant comprises an amino acid substitution at 5223 (e.g., S223R);

26) a first variant of fHbp ID 55, where the first fHbp ID 55 variant comprises an amino acid substitution at E92 (e.g., E92K); and a second variant of fHbp ID 55, where the second fHbp ID 55 variant comprises an amino acid substitution at H248 (e.g., H248L);

27) a variant of fHbp ID22 comprising amino acid substitutions: L130R and G133D and a variant of fHbp ID 1, where the fHbp ID 1 variant comprises an amino acid substitution at S223 (e.g., S223R);

28) a variant of fHbp ID22 comprising amino acid substitutions: L130R and G133D and a variant of fHbp ID 1, where the fHbp ID 1 variant comprises an amino acid substitution at H248 (e.g., H248L);

29) a variant of fHbp ID22 comprising amino acid substitutions: L130R, G133D, and K219N and a variant of fHbp ID 1, where the fHbp ID 1 variant comprises an amino acid substitution at 5223 (e.g., S223R) or H248 (e.g., H248L); or 30) a variant of fHbp ID22 comprising amino acid substitutions: L130R, G133D, and G220S and a variant of fHbp ID 1, where the fHbp ID 1 variant comprises an amino acid substitution at 5223 (e.g., S223R) or H248 (e.g., H248L).

Immunogenic compositions contemplated by the present disclosure include, but are not limited to, compositions comprising:

1) at least one variant fHbp of the present disclosure; and
2) NspA;

where the fHbp and/or NspA can be provided as recombinant proteins and/or in a vesicle-based composition (e.g., OMV or MV). It should be noted that where the composition includes both NspA and a fHbp, the bactericidal activity of antibodies elicited by administration of the composition can result from cooperation of antibodies to one or both antigens. Examples of immunogenic compositions provided by the present disclosure include:

a) an immunogenic composition that comprises a fHbp variant as described above (e.g., where the variant fHbp elicits a bactericidal antibody response to at least one *Neisseria meningitidis* strain);

b) an immunogenic composition that comprises a fHbp variant as described above (e.g., where the variant fHbp elicits a bactericidal antibody response to at least one *Neisseria meningitidis* strain); and a recombinant NspA protein;

c) an immunogenic composition that comprises a native OMV obtained from a genetically modified *Neisseria* host cell that is genetically modified with a nucleic acid encoding a variant fHbp of the present disclosure, such that the encoded variant fHbp is produced by the genetically modified host cell, where the OMV comprises the encoded variant fHbp; and d) an immunogenic composition that comprises a native OMV obtained from a genetically modified *Neisseria* host cell that is genetically modified with a nucleic acid encoding a variant fHbp of the present disclosure, such that the encoded non-naturally occurring fHbp is produced by the genetically modified host cell, where the OMV comprises the encoded variant fHbp; and where the *Neisseria* host cell also produces higher levels of NspA, such that the OMV also comprises NspA. For example, the *Neisseria* host cell can be one that is genetically modified for increased expression of NspA.

By "immunologically effective amount" is meant that the administration of that amount to an individual, either in a single dose, as part of a series of the same or different antigenic compositions, is effective to elicit an antibody response effective for treatment or prevention of a symptom of, or disease caused by, for example, infection by *Neisseria*, particularly *N. meningitidis*, more particularly Group B *N. meningitidis*. This amount varies depending upon the health and physical condition of the individual to be treated, age, the capacity of the individual's immune system to produce antibodies, the degree of protection desired, the formulation of the vaccine, the treating clinician's assessment of the medical situation, and other relevant factors. It is expected that the amount will fall in a relatively broad range that can be determined through routine trials.

Amino acid sequences of NspA polypeptides are known in the art. See, e.g., WO 96/29412; and Martin et al. (1997) J. Exp. Med. 185:1173; GenBank Accession No. U52066; and GenBank Accession No. AAD53286. An "NspA polypeptide" can comprise an amino acid sequence having at least about 80%, at least about 85%, at least about 90%, at least about 95%, at least about 98%, at least about 99%, or 100%, amino acid sequence identity to a contiguous stretch of from about 75 amino acids to about 100 amino acids, from about 100 amino acids to about 150 amino acids or from about 150 amino acids to about 174 amino acids, of the amino acid sequence depicted in FIG. 40 and set forth in SEQ ID NO:25. An "NspA polypeptide" can comprise an amino acid sequence having at least about 80%, at least about 85%, at least about 90%, at least about 95%, at least about 98%, at least about 99%, or 100%, amino acid sequence identity to a contiguous stretch of from about 75 amino acids to about 100 amino acids, or from about 100 amino acids to about 155 amino acids, of amino acids 20 to 174 of the amino acid sequence depicted in FIG. 40 and set forth in SEQ ID NO:25. In some cases, the NspA polypeptide lacks a signal sequence; in other cases (e.g., for expression in a host cell), the NspA polypeptide includes a signal sequence.

Dosage regimen may be a single dose schedule or a multiple dose schedule (e.g., including booster doses) with a unit dosage form of the antigenic composition administered at different times. The term "unit dosage form," as used herein, refers to physically discrete units suitable as unitary dosages for human and animal subjects, each unit containing a predetermined quantity of the antigenic compositions of the present disclosure in an amount sufficient to produce the desired effect, which compositions are provided in association with a pharmaceutically acceptable excipient (e.g., pharmaceutically acceptable diluent, carrier or vehicle). The antigenic composition may be administered in conjunction with other immunoregulatory agents.

Antigenic compositions can be provided in a pharmaceutically acceptable excipient, which can be a solution such as a sterile aqueous solution, often a saline solution, or they can be provided in powder form. Such excipients can be substantially inert, if desired.

In some embodiments, a subject immunogenic composition comprises a subject fHbp present in a vesicle. In some embodiments, a subject immunogenic composition comprises a subject fHbp present in an MV. In some embodiments, a subject immunogenic composition comprises a subject fHbp present in an OMV. In some embodiments, a subject immunogenic composition comprises a mixture of MV and OMV comprising a subject fHbp. Vesicles, such as MV and OMV, are described above.

The antigenic compositions can further contain an adjuvant. Examples of known suitable adjuvants that can be used in humans include, but are not necessarily limited to, an aluminum adjuvant (e.g., aluminum phosphate, or aluminum hydroxide), MF59 (4.3% w/v squalene, 0.5% w/v TWEEN 80™, 0.5% w/v SPAN 85), a CpG-containing nucleic acid (where the cytosine is unmethylated), QS21, MPL, 3DMPL, extracts from Aquilla, ISCOMS, LT/CT mutants, poly(D,L-lactide-co-glycolide) (PLG) microparticles, Quil A, interleukins, and the like. For experimental animals, one can use Freund's adjuvant (incomplete Freund's adjuvant; complete Freund's adjuvant), N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dip-almitoyl-sn-glycero-3-hydroxyphosphoryloxy)-ethylamine (CGP 19835A, referred to as MTP-PE), and RIBI, which contains three components extracted from bacteria, monophosphoryl lipid A, trehalose dimycolate and cell wall skeleton (MPL+TDM+CWS) in a 2% squalene/TWEEN 80 emulsion. The effectiveness of an adjuvant may be determined by measuring the amount of antibodies directed against the immunogenic antigen or antigenic epitope thereof.

Further exemplary adjuvants to enhance effectiveness of the composition include, but are not limited to: (1) oil-in-water emulsion formulations (with or without other specific immunostimulating agents such as muramyl peptides (see below) or bacterial cell wall components), such as for example (a) MF59 (WO 90/14837; Chapter 10 in Vaccine design: the subunit and adjuvant approach, eds. Powell & Newman, Plenum Press 1995), containing 5% Squalene, 0.5% TWEEN 80, and 0.5% SPAN 85 (optionally containing MTP-PE) formulated into submicron particles using a microfluidizer, (b) SAF, containing 10% Squalane, 0.4% TWEEN 80, 5% PLURONIC-blocked polymer L121, and thr-MDP either microfluidized into a submicron emulsion or vortexed to generate a larger particle size emulsion, and (c) RIBI adjuvant system (RAS), (Ribi Immunochem, Hamilton, Mont.) containing 2% Squalene, 0.2% TWEEN 80, and one or more bacterial cell wall components such as monophosphorylipid A (MPL), trehalose dimycolate (TDM), and cell wall skeleton (CWS), e.g., MPL+CWS (Detox TM); (2) saponin adjuvants, such as QS21 or Stimulon™ (Cambridge Bioscience, Worcester, Mass.) may be used or particles generated therefrom such as ISCOMs (immunostimulating complexes), which ISCOMS may be devoid of additional detergent e.g. WO 00/07621; (3) Complete Freund's Adjuvant (CFA) or Incomplete Freund's Adjuvant (IFA); (4) cytokines, such as interleukins (e.g. IL-1, IL-2, IL-4, IL-5, IL-6, IL-7, IL-12 (WO99/44636), etc.), interferons (e.g. gamma interferon), macrophage colony stimulating factor (M-CSF), tumor necrosis factor (TNF), etc.; (5) monophosphoryl lipid A (MPL) or 3-O-deacylated MPL (3dMPL) e.g. GB-2220221, EP-A-0689454, optionally in the substantial absence of alum when used with pneumococcal saccharides e.g. WO 00/56358; (6) combinations of 3dMPL with, for example, QS21 and/or oil-in-water emulsions e.g. EP-A-0835318, EP-A-0735898, EP-A-0761231; (7) oligonucleotides comprising CpG motifs (see, e.g., WO 98/52581), e.g., an oligonucleotide containing at least one CG dinucleotide, where the cytosine is unmethylated; (8) a polyoxyethylene ether or a polyoxyethylene ester (see, e.g. WO 99/52549); (9) a polyoxyethylene sorbitan ester surfactant in combination with an octoxynol (WO 01/21207) or a polyoxyethylene alkyl ether or ester surfactant in combination with at least one additional non-ionic surfactant such as an octoxynol (WO 01/21152); (10) a saponin and an immunostimulatory oligonucleotide (e.g. a CpG oligonucleotide) (WO 00/62800); (11) an immunostimulant and a particle of metal salt e.g. WO 00/23105; (12) a saponin and an oil-in-water emulsion e.g. WO 99/11241; (13) a saponin (e.g. QS21)+3dMPL+IM2 (optionally+a sterol) e.g. WO 98/57659; (14) other substances that act as immunostimulating agents to enhance the efficacy of the composition. Muramyl peptides include N-acetyl-muramyl-L-threonyl-D-isoglutamine (thr-MDP), N-25 acetyl-normuramyl-L-alanyl-D-isoglutamine (nor-MDP), N-acetylmuramyl-L-alanyl-D-isoglutarninyl-L-alanine-2-(1'-2'-dipalmitoyl-sn-glycero-3-hydroxyphosphoryloxy)-ethylamine MTP-PE), etc. Adjuvants suitable for administration to a human are of particular interest. In some cases, the adjuvant is an aluminum salt adjuvant (e.g., aluminum phosphate or aluminum hydroxide).

The antigen compositions may contain other components, such as pharmaceutical grades of mannitol, lactose, starch, magnesium stearate, sodium saccharin, talcum, cellulose, glucose, sucrose, magnesium, carbonate, and the like. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like.

The concentration of the subject fHbp in a formulation can vary widely (e.g., from less than about 0.1%, e.g., at or at least about 2% to as much as 20% to 50% or more by weight) and will usually be selected primarily based on fluid volumes, viscosities, and patient-based factors in accordance with the particular mode of administration selected and the patient's needs.

The fHbp-containing formulations can be provided in the form of a solution, suspension, tablet, pill, capsule, powder, gel, cream, lotion, ointment, aerosol or the like. It is recognized that oral administration can require protection of the compositions from digestion. This is typically accomplished either by association of the composition with an agent that renders it resistant to acidic and enzymatic hydrolysis or by packaging the composition in an appropriately resistant carrier. Means of protecting from digestion are well known in the art.

The fHbp-containing formulations can also be provided so as to enhance serum half-life of fHbp following administration. For example, where isolated fHbps are formulated for injection, the fHbp may be provided in a liposome formulation, prepared as a colloid, or other conventional techniques for extending serum half-life. A variety of methods are available for preparing liposomes, as described in, e.g., Szoka et al., Ann. Rev. Biophys. Bioeng. 9:467 (1980), U.S. Pat. Nos. 4,235,871, 4,501,728 and 4,837,028. The preparations may also be provided in controlled release or slow-release forms.

Methods of Inducing an Immune Response

The present disclosure provides a method of inducing an immune response to at least one Neisserial strain in a mammalian host. The methods generally involve administering to an individual in need thereof an effective amount of a subject immunogenic composition.

The fHbp-containing antigenic compositions are generally administered to a human subject that is at risk of acquiring a Neisserial disease so as to prevent or at least partially arrest the development of disease and its complications. An amount adequate to accomplish this is defined as a "therapeutically effective dose." Amounts effective for therapeutic use will depend on, e.g., the antigenic composition, the manner of administration, the weight and general state of health of the patient, and the judgment of the prescribing physician. Single or multiple doses of the antigenic compositions may be administered depending on the dosage and frequency required and tolerated by the patient, and route of administration.

The fHbp-containing antigenic compositions are generally administered in an amount effective to elicit an immune response, particularly a humoral immune response, e.g., a bactericidal antibody response, in the host. As noted above, amounts for immunization will vary, and can generally range from about 1 µg to 100 µg per 70 kg patient, usually 5 µg to 50 µg/70 kg. Substantially higher dosages (e.g. 10 mg to 100 mg or more) may be suitable in oral, nasal, or topical administration routes. The initial administration can be followed by booster immunization of the same of different fHbp-containing antigenic composition. Vaccination in some cases involves at least one booster, and in some cases two boosters.

In general immunization can be accomplished by administration by any suitable route, including administration of the composition orally, nasally, nasopharyngeally, parenterally, enterically, gastrically, topically, transdermally, subcutaneously, intramuscularly, in tablet, solid, powdered, liquid, aerosol form, locally or systemically, with or without added excipients. Actual methods for preparing parenterally administrable compositions will be known or apparent to those skilled in the art and are described in more detail in such publications as Remington's Pharmaceutical Science, 15th ed., Mack Publishing Company, Easton, Pa. (1980).

An anti-fHbp immune response can be assessed by known methods (e.g. by obtaining serum from the individual before and after the initial immunization, and demonstrating a change in the individual's immune status, for example an immunoprecipitation assay, an ELISA, or a bactericidal assay, a Western blot assay, or flow cytometric assay, or the like).

Whether a variant fHbp of the present disclosure elicits a bactericidal response to one or more strains of *N. meningitidis* in a mammalian host can be determined using any well-known assay. For example, a human fH transgenic mouse can be used, where the mouse expresses human fH (e.g., human fH is present in serum of the mouse at a concentration of about 100 μg/ml or greater than 100 μg/ml). A variant fHbp of the present disclosure is administered to the human fH transgenic mouse. After a period of time, serum from the mouse is tested for bactericidal activity against one or more strains of *N. meningitidis*. Suitable controls include, e.g., fHbp ID 1. An example of a suitable assay is described in Vu et al. (2012) *Sci. Reports* 2:341.

The antigenic compositions can be administered to a mammalian host (e.g., a human subject) that is immunologically naive with respect to *Neisseria meningitidis*. In a particular embodiment, the subject is a human child about five years or younger, and preferably about two years old or younger, and the antigenic compositions are administered at any one or more of the following times: two weeks, one month, 2, 3, 4, 5, 6, 7, 8, 9, 10, or 11 months, or one year or 15, 18, or 21 months after birth, or at 2, 3, 4, or 5 years of age.

It may be generally desirable to initiate immunization prior to the first sign of disease symptoms, or at the first sign of possible or actual exposure to infection or disease (e.g., due to exposure or infection by *Neisseria*).

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Example 1: Identification and Characterization of fHbp ID 1 Mutants

Materials and Methods

Library Screening

A random mutant fHbp library was generated by error-prone polymerase chain reaction (PCR), which was followed by cloning of the PCR products into a pET28 expression plasmid that included a signal sequence to allow surface display on *E. coli*. Fluorescence-activated cell sorting was used to isolate mutant clones with low binding of human fH and high binding of a control anti-fHbp monoclonal antibody, which ensured sufficient expression and proper folding of the fHbp mutants. The collected cells were plated on agar plates (LB agar containing 50 μg/ml kanamycin sulfate), which were incubated overnight at 37° C. Single *E. coli* colonies were used as templates for PCR amplification and the DNA amplicons were purified (PCR Purification Kit; Qiagen) and subjected to DNA sequencing of the fHbp gene using primers that annealed to the T7 promotor and T7 terminator. The approach of screening a random mutant fHbp library has the potential to identify: 1) positions that affect fH binding that are not predictable from the crystal structure alone; and 2) substitutions other than alanine that affect binding of fH in cases where an alanine substitution would not result in a sufficient decrease in fH binding.

Selection of Mutants for Further Study

The positions of amino acid substitutions that were identified from the FACS experiment were examined in the crystal structure of fHbp in a complex with a fragment of human fH. Mutants that were in proximity (<5 Å) to the fH binding interface were chosen for site-specific mutagenesis. Recapitulation of the library mutants by site-specific mutagenesis was necessary to create soluble, recombinant fHbp proteins for further characterization. This approach also removed non-desired secondary mutations, which were present in many of the sorted clones and which were distant from the fH binding site. The site-specific mutants were constructed with the Phusion Site-Directed Mutagenesis Kit (Thermo Scientific, Inc.).

Expression and Purification of Soluble, Mutant fHbps

Soluble, recombinant fHbps were expressed in *E. coli* and lysates were prepared as previously described. fHbps were purified by nickel-affinity chromatography using HiTrap Chelating HP columns (5 ml; GE Life Sciences, Inc.) and an Akta Purifier chromatography system (GE Life Sciences). Buffers for binding and elution using an imidazole gradient were prepared according to the column manufacturer's protocols. Fractions containing purified fHbp were combined, dialyzed against PBS containing 3% sucrose and stored at −80° C. prior to use.

For mouse immunogenicity studies, a second purification step was performed using ion exchange chromatography with HiTrap SP HP columns (5 ml; GE Life Sciences). The binding and elution buffers were 25 mM MES, pH 5.5, containing 150 mM and 750 mM NaCl, respectively. Bound fHbp was eluted from the SP column with a linear gradient formed by the binding and elution buffers. Fractions containing purified fHbp were combined, dialyzed against PBS containing 3% sucrose and stored at −80° C. prior to use.

Purification of Human Factor H (fH)

Human fH was purified on a fHbp affinity column. The column was prepared by coupling 5 mg of fHbp ID 1 to an NHS-activated HP column (5 ml; GE Life Sciences) using the manufacturer's protocols. Human serum from a healthy individual donor was diluted 1:1 in phosphate-buffered saline (PBS). The serum was applied to the column and the column was washed with 10 volumes of PBS (i.e. 50 ml). The bound fH was eluted with 5 column volumes of 0.1 M glycine-HCl, pH 2.7. The elution fractions were collected in tubes containing 50 µl of 1 M TRIS-HCl, pH 9.0. Fractions containing fH were identified by sodium dodecyl sulfate-polyacrylamide gel electrophoresis (SDS-PAGE) (4-12% NuPAGE; Invitrogen). Electrophoresis was performed at 200 V for 45 min using 1× MES Running Buffer (Invitrogen). The proteins were visualized by staining with COOMASSIE G-250 (SimplyBlue SafeStain; Invitrogen). Fractions containing fH were pooled and dialyzed against PBS and aliquots of fH were stored at −30° C. prior to use.

Characterization of fHbp Mutants

SDS-PAGE. The size and purity of the purified fHbp mutant proteins was assessed by SDS-PAGE using 4-12% polyacrylamide gradient gels (NuPAGE; Invitrogen, Inc.). Two µg of each protein was loaded on the gel. SDS-PAGE was performed as described above for fH.

Binding of fH to fHbp by enzyme-linked immunosorbent assay (ELISA). The wells of a 96-well microtiter plate (Immulon 2HB; Thermo Scientific) were coated with 2 µg/ml of purified, recombinant wild-type fHbp (positive control) or mutant fHbp (experimental). Nonspecific binding to the wells was blocked with PBS containing 1% BSA (Lifeblood Medical, Inc.) or 5% non-fat dry milk (Carnation; Nestle, Inc.). Five-fold serial dilutions of purified human fH ranging from 25 to 0.0016 µg/ml in Dilution Buffer (PBS containing 0.1% TWEEN-20, 0.01% sodium azide and 1% BSA), were added to the wells and the plate was incubated at room temperature for 2 h. After washing three times with PBS containing 0.1% Tween-20 (Sigma) and 0.01% sodium azide (Sigma), bound fH was detected with sheep anti-human fH (1:7,000; Abcam, Inc.) in Dilution Buffer. The plate was incubated at room temperature for 1 h. After washing the wells again, bound primary antibody was detected with donkey anti-sheep IgG conjugated to alkaline phosphatase (1:5,000; Sigma-Aldrich, Inc.) in Dilution Buffer. The plate was incubated at room temperature for 1 h and the wells were washed again. The ELISA was developed with phosphatase substrate (1 mg/ml para-nitrophenyl phosphate; Sigma) in Substrate Buffer (50 mM sodium carbonate, 1 mM $MgCl_2$, pH 9.8). After incubation at room temperature for 30 min, the absorbance at 405 nm was measured in a UV-VIS plate reader (Spectromax 190; Molecular Devices, Inc.).

Binding of anti-fHbp monoclonal antibodies to fHbp by ELISA. The wells of a microtiter plate were coated with fHbp, blocked and washed as described above for the fH ELISA. Five-fold serial dilutions of murine anti-fHbp monoclonal antibodies (mAbs) from 25 to 0.0016 µg/ml in Dilution Buffer were added and the plate was incubated at room temperature for 1 h. After washing the wells, primary antibody was detected with goat anti-mouse IgG conjugated to alkaline phosphatase (1; 5,000; Sigma-Aldrich). The ELISA was developed and read as described above.

Binding of fH to fHbp by surface plasmon resonance (SPR). SPR experiments were performed on a Biacore X100 Plus instrument (GE Life Sciences). Three thousand response units of purified human fH were coupled to a CM5 chip (GE Life Sciences) using the Amine Coupling Kit (GE Life Sciences). fH was immobilized in flow cell 2 and a blank immobilization (no fH) was performed in flow cell 1 as a reference. Three startup cycles consisting of HEPES-buffered saline containing 3 mM EDTA and 0.05% Surfactant P-20 (GE Life Sciences) and regeneration with 100 mM Glycine, 3 M NaCl, pH 2.0, were performed to condition the chip surface. Dilutions of purified, recombinant fHbp ranging from 100 to 1 nM (wild-type) or 316 to 3.16 nM were injected for 150 seconds. Dissociation was monitored for 300 sec. and the data were analyzed with Biacore X100 Evaluation software.

Mouse immunogenicity. Groups of wild-type CD-1 mice (N=14 to 21) were immunized with fHbp vaccines adsorbed with aluminum hydroxide. Each dose of vaccine contained 10 µg of fHbp and 600 µg of ALHYDROGEL (Brenntag Biosector) in 10 mM Histidine, 150 mM NaCl, pH 6.5. Two doses were given three-weeks apart and blood was collected by cardiac puncture three weeks after the second dose. Blood was processed to obtain serum, which was kept at −80° C. for long-term storage (>2 weeks) or 4° C. for short-term storage (<2 weeks).

Human fH transgenic BALB/c mice first were screened to identify animals with serum human fH concentrations>240 µg/ml using a fHbp ELISA and a standard curve of purified human fH. The ELISA was performed using purified fHbp ID 1 immobilized on the plate, and the primary and secondary antibodies to detect fH were the same as described above (see "Binding of fH to fHbp by ELISA").

Groups of transgenic mice (N=11 to 21) were immunized with fHbp vaccines adsorbed with aluminum hydroxide (same amount of antigen and adjuvant as for wild-type CD-1 mice described above). Three doses were administered at three-week intervals and blood was collected three weeks after the third dose of vaccine. Serum was processed and stored as described above.

Serum bactericidal antibody (SBA) responses. Human complement-mediated SBA responses were measured against meningococcal strains with an identical or closely matched fHbp sequence compared with the respective vaccine antigen. The bacteria were grown in regular Frantz medium (Frasch et al. "Outer membrane protein vesicle vaccines for meningococcal disease." In Methods in Molecular Medicine, v. 66. Meningococcal Vaccines: Methods and Protocols. Edited by Pollard, A. J. and Maiden, M. C. Humana Press Inc. Totowa, N.J.) containing 4 mM lactate and 0.02 mM CMP-NANA to mid-exponential phase (OD620 nm=0.6). The bacteria were diluted 1:25,000 in Dulbecco's PBS containing 1% BSA (Equitech Bio.). Human complement was from a donor with no intrinsic bactericidal antibodies and was depleted of IgG antibodies using a HiTrap Protein G column (5 ml; GE Life Sciences). Each reaction contained 25% human complement, ~400 cfu of bacteria and dilutions of test antisera or control antibodies. The SBA titer was calculated as the serum dilution that resulted in a 50% decrease in cfu relative to negative control wells after 60 min incubation at 37° C. Protein purification: Recombinant fHbps were expressed in *E. coli* with a C-terminal hexa-histidine tag and purified by metal chelate chromatography (HiTrap Chelating HP; GE Life Sciences) followed by ion exchange chromatography (HiTrap SP; GE Life Sciences). The proteins (2 µg each) were separated on a 4-12% NuPAGE gel (Invitrogen) using MES running buffer (Invitrogen), and visualized with COOMASSIE blue staining (Simply Blue Safe Stain; Invitrogen).

Results

A random mutant library-based approach was developed to identify fHbp mutants with decreased binding of human fH. This approach was able to identify mutations leading to decreased binding of fH that might not be predictable based on structural information alone, and was able to generate multiple amino acid substitutions at any given position. This approach contrasts with the common approach of substitution of alanine at selected positions, which sometimes results in small decreases in binding of fH.

Using the random mutant library approach, we identified five promising new fHbp ID 1 mutants. The purified, recombinant mutant fHbp ID 1 antigens Q38R, E92K, R130G, S223R and H248L are shown in FIG. 1.

FIG. 1. Purity of fHbp ID 1 mutants. Recombinant fHbps were expressed in E. coli with a C-terminal hexa-histidine tag and purified by metal chelate chromatography (HiTrap Chelating HP; GE Life Sciences) followed by ion exchange chromatography (HiTrap SP; GE Life Sciences). The proteins (2 µg each) were separated on a 4-12% NuPAGE gel (Invitrogen) using MES running buffer (Invitrogen), and visualized with COOMASSIE blue staining (Simply Blue Safe Stain; Invitrogen). Lane 1, Kaleidoscope molecular weight marker (Bio-Rad Laboratories); 2, fHbp ID 1 wild-type; 3, Q38R; 4, E92K; 5, R130G; 6, S223R; 7, H248L.

These mutants exhibit decreased binding of fH ranging from ~10-fold (R130G) to ~20-fold (Q38R) to ~100-fold (E92K, S223R and H248L) (FIG. 2).

Figures 2A, 2B:
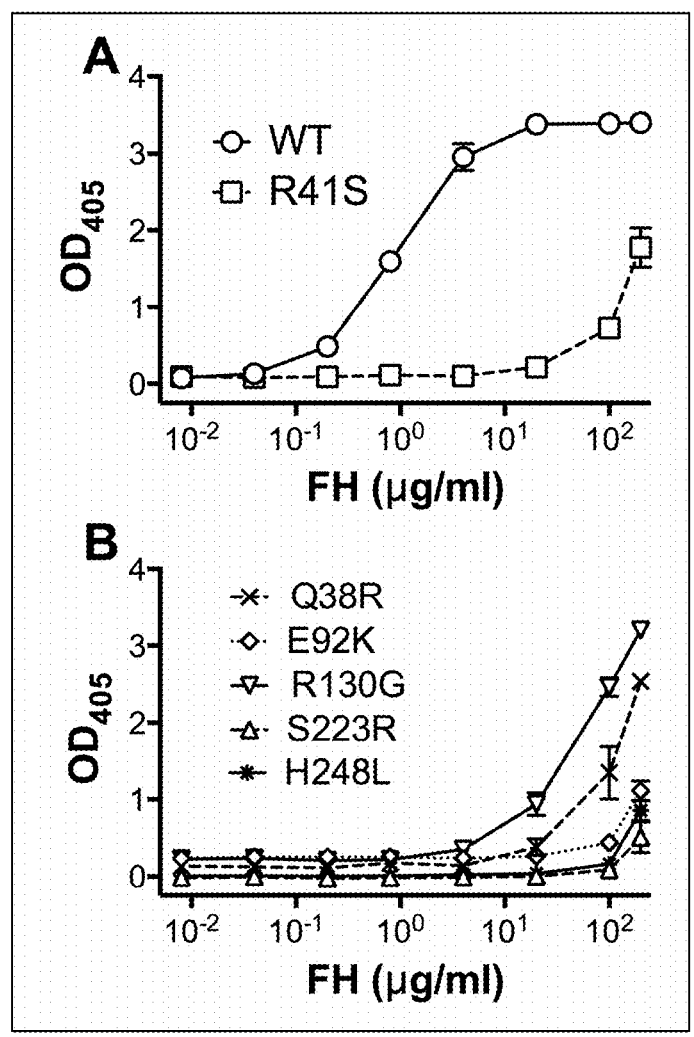
FIGS. 2A and 2B depict binding of fHbp ID 1 mutants to human fH, measured by ELISA. The mean and range for replicate measurements are shown.

FIGS. 2A and 2B. fH binding of fHbp ID 1 mutants by ELISA. The wells of a microtiter plate were coated with purified recombinant ID 1 wild-type (WT) or one of six different mutant proteins. Different concentrations of purified human fH were added to the wells. Bound fH was detected with sheep anti-human fH (Abcam) and donkey anti-sheep IgG conjugated to alkaline phosphatase (Sigma). A, Positive control fHbp ID 1 wild-type (WT) protein with high binding of human fH. Negative control fHbp ID 1 R41S mutant with low binding of fH. B, New fHbp ID 1 mutants with decreased binding of fH. The R130G mutant showed moderate binding of fH, Q38R showed low binding and E92K, S223R and H248L showed significantly lower binding than that of R41S. The mean and standard deviation for replicate measurements are shown.

Figures 3A, 3B, 3C, 3D, 3E:
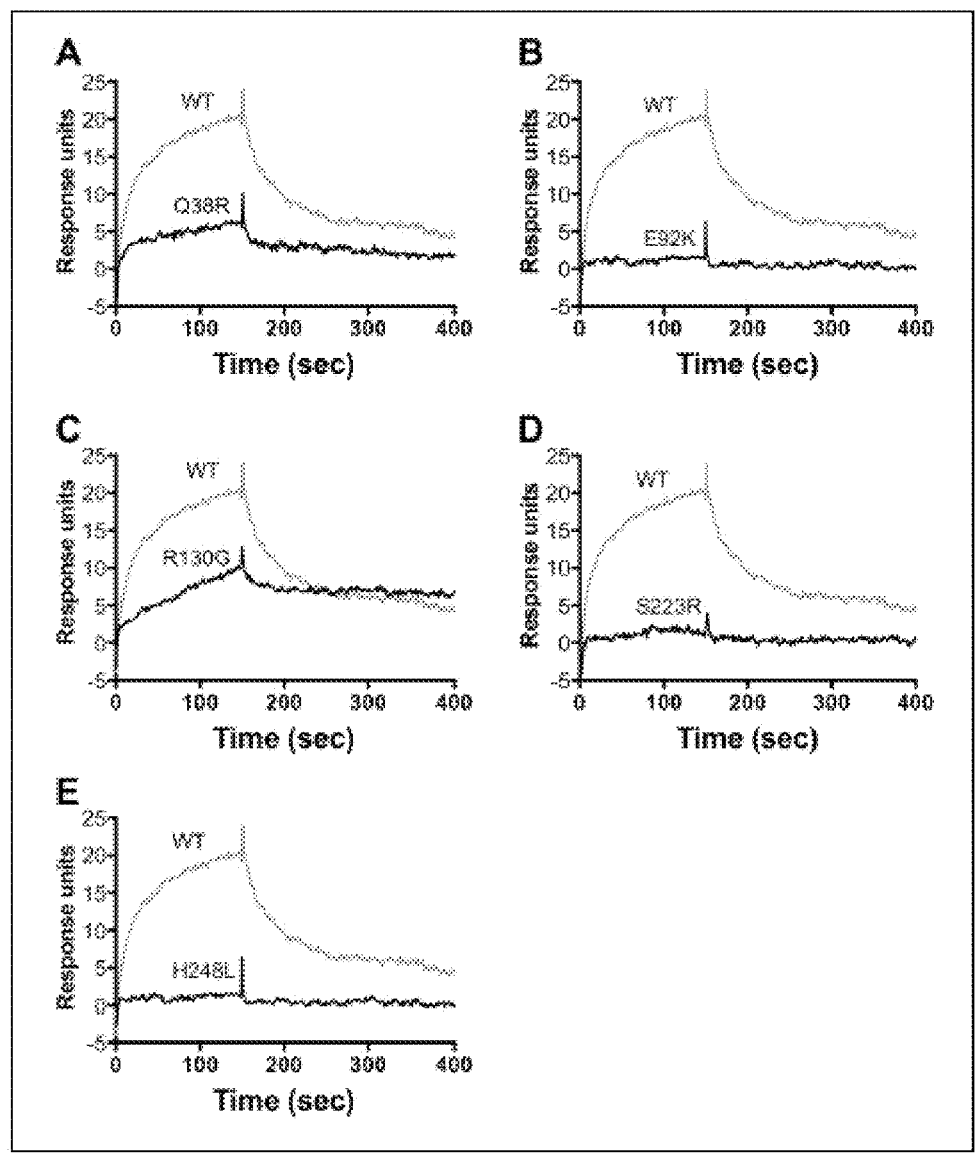
FIGS. 3A-3E depict binding of fHbp ID 1 mutants to human fH, measured by surface plasmon resonance. For reference, the same data for the ID 1 wild-type (WT) protein are shown in each of FIGS. 3A-3E.

A similar pattern of decreased binding of fH to the mutant proteins was obtained from surface plasmon experiments, in which the R130G and Q38R mutants show some binding, whereas the other three mutants show no detectable binding (FIGS. 3A and 3B).

FIGS. 3A-3E. fH binding of fHbp ID 1 mutants by surface plasmon resonance. 3000 response units of purified human fH were coupled to a CM5 chip (GE Life Sciences) and 316 nM of purified, recombinant fHbp was injected for 150 seconds. For reference, the same data for the ID 1 wild-type (WT) protein are shown in each panel. The same pattern of binding was observed as in the ELISA (FIG. 2, above); moderate binding to fH for R130G mutant, low binding for Q38R and very low binding for E92K, S223R and H248L. All experiments employed HBS-EP running buffer and a Biacore X100 Plus surface plasmon resonance instrument. Data were analyzed with Biacore X100 Evaluation software.

Figures 4A, 4B, 4C, 4D, 4E:
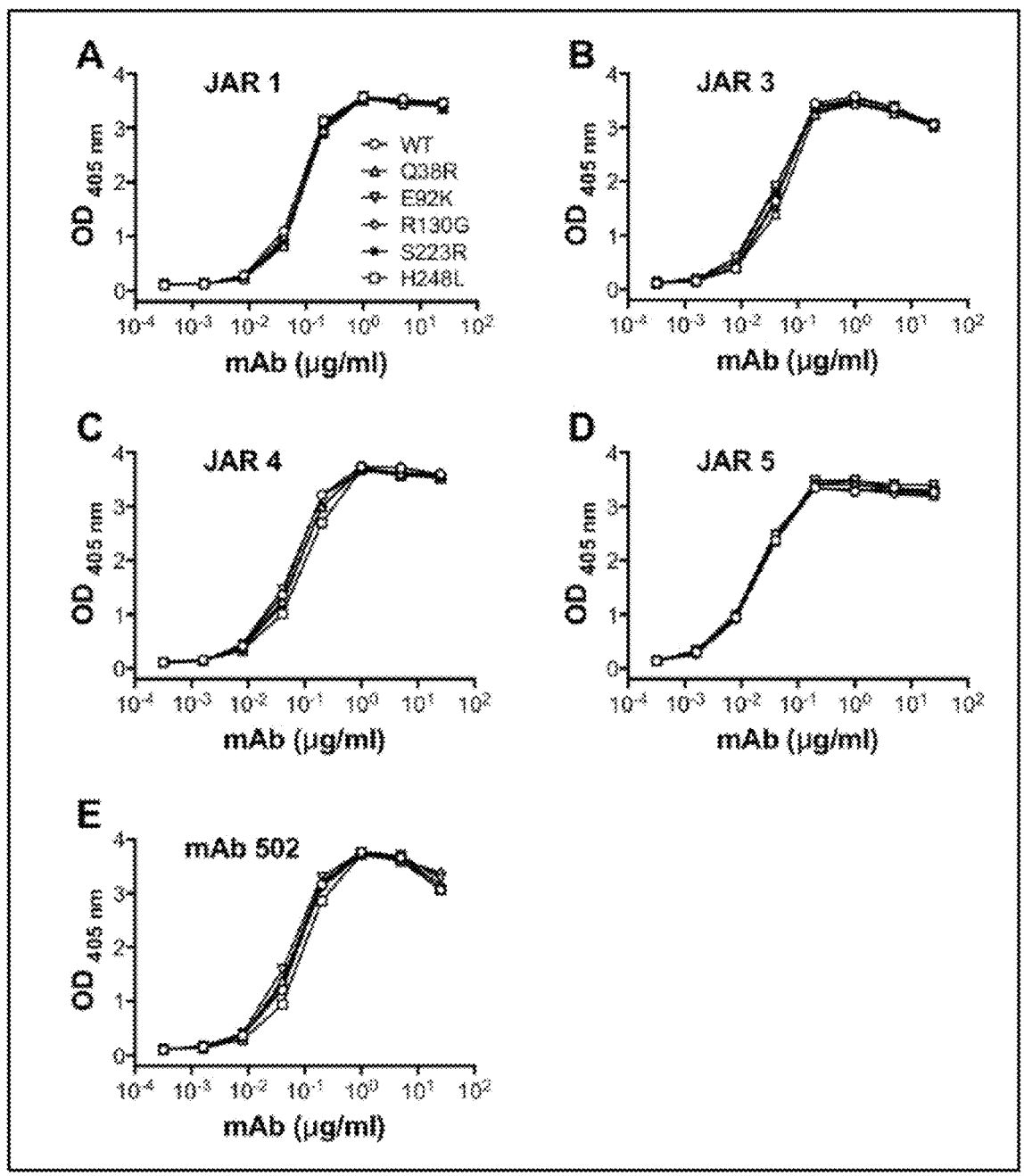
FIG. 4A-4E depict binding of murine anti-fHbp monoclonal antibodies (mAb) to fHbp ID 1 mutant proteins, measured by ELISA. The mean and range for duplicate measurements are shown.

All five of the mutant fHbp ID 1 proteins retained conformational epitopes recognized by anti-fHbp monoclonal antibodies. Concentration-dependent binding of five anti-fHbp monoclonal antibodies to wild-type or mutant fHbps is shown in FIG. 4.

FIGS. 4A-4E. Binding of murine anti-fHbp monoclonal antibodies to fHbp mutant proteins as measured by ELISA. Similar concentration-dependent binding of anti-fHbp monoclonal antibodies indicated that the wild-type and mutant fHbps were present in similar amounts in the wells of the microtiter plate and that the mutant fHbps retained conformational epitopes recognized by five distinct monoclonal antibodies. The secondary antibody was goat anti-mouse IgG conjugated to alkaline phosphatase (Sigma). The mean and standard deviation for duplicate measurements are shown.

The mutant proteins also retain thermal stability similar to the wild-type fHbp ID 1, except the E92K mutant, which has somewhat decreased stability. Finally, the mutants elicited similar bactericidal antibody responses in wild-type CD-1 mice when tested against serogroup B strain H44/76 (FIGS. 5A-5B).

Figures 5A, 5B:
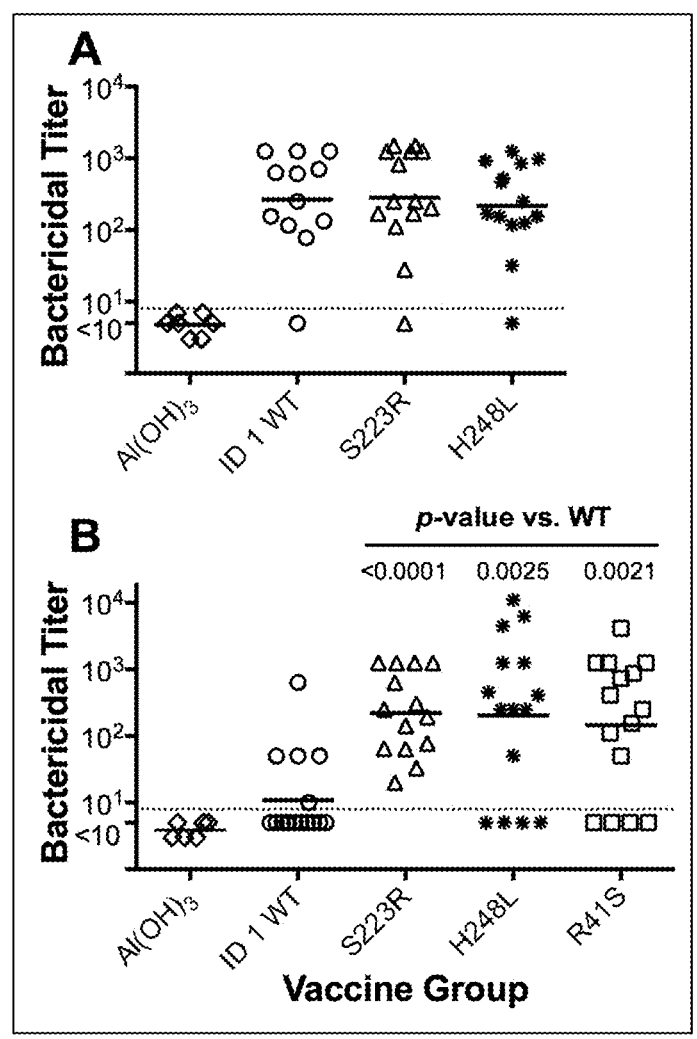
FIGS. 5A and 5B depict bactericidal activity of serum from mice immunized with fHbp ID 1 mutants. Each symbol represents the titer of an individual mouse, and the horizontal bars represent the geometric mean titers.

FIGS. 5A and 5B. Bactericidal antibody responses to fHbp ID 1 mutants in mice. FIG. 5A, Groups of 12 to 14 wild-type mice were immunized intraperitoneally with two doses of purified recombinant fHbp (10 µg per dose) given at three-week intervals. Serum was obtained three weeks after the second dose. Serum bactericidal activity was measured using IgG-depleted human serum as the complement source and serogroup B strain H44/76 as the test strain. H44/76 expresses fHbp ID 1, which matches the control fHbp ID 1 WT vaccine. Each symbol represents the titer of an individual mouse, and the horizontal bars represent the geometric mean titers. The differences between the WT group and each of the mutant groups were not statistically significantly different (p>0.4 by t-test). FIG. 5B, Groups of 14 to 15 human fH transgenic mice were immunized intraperitoneally with three doses of purified recombinant fHbp (10 µg per dose) given at three-week intervals. Serum was obtained three weeks after the third dose. Serum bactericidal activity was measured as described above for wild-type mice.

Figures 6A, 6B:
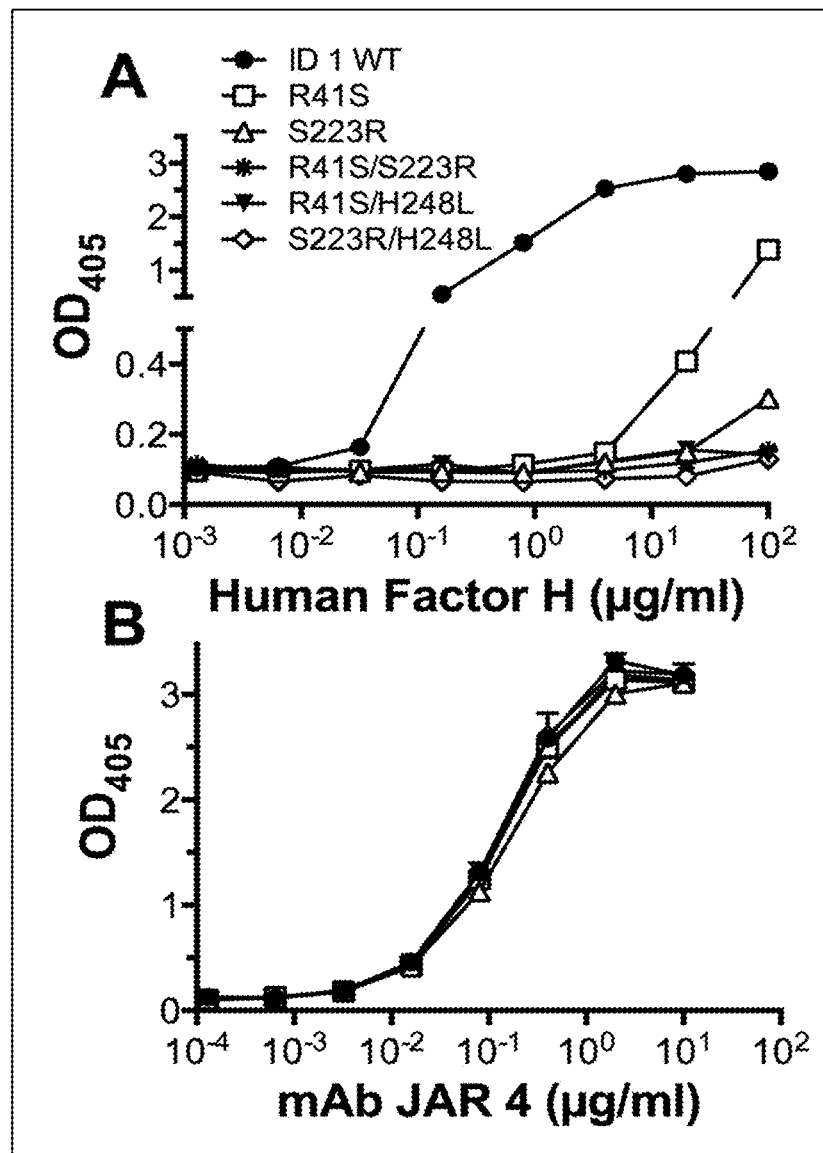
FIGS. 6A and 6B depict characterization of fHbp ID 1 single or double mutants.
Figure 7:
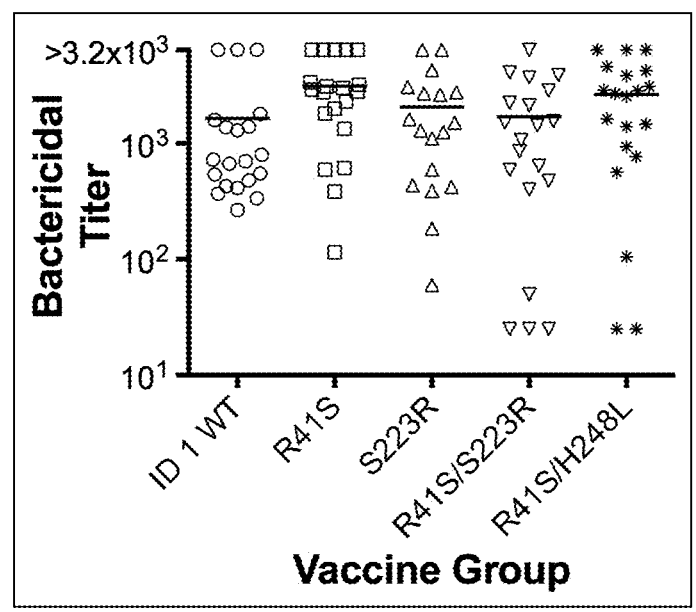
FIG. 7 depicts bactericidal activity of serum from wild-type mice immunized with fHbp ID 1 single or double mutants. Each symbol represents the titer of an individual mouse, and the horizontal bars represent the geometric mean titers.

FIGS. 6A and 6B. Binding of human fH to fHbp ID 1 single and double mutants by ELISA. The experiments were performed as described above for FIGS. 2A-2B. FIG. 7. Bactericidal antibody responses to fHbp ID 1 single and double mutants in mice. Groups of 20 wild-type mice were immunized and the serum bactericidal antibody responses were determined as described above for FIG. 5A.

Example 2: Characterization of fHbp ID 55 Mutants

Materials and Methods

The experiments were performed as described in Example 1.

Results

Figures 8A, 8B:
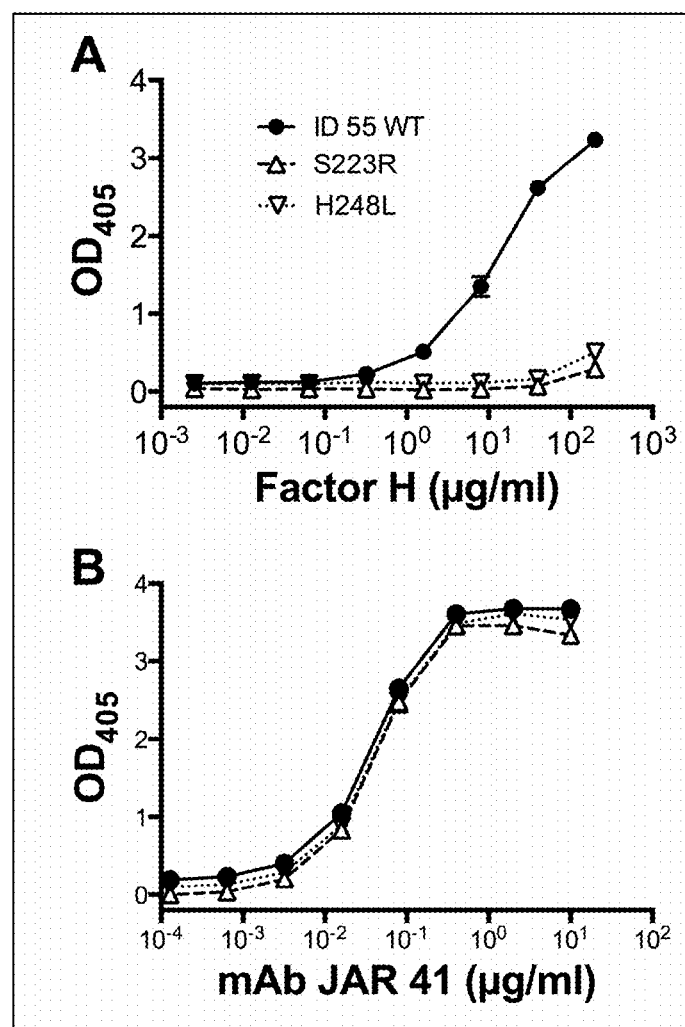
FIGS. 8A and 8B depict characterization of fHbp ID 55 mutants.

Three promising mutants that were identified in fHbp ID 1 also were constructed in fHbp ID 55; these included E92K, S223R and H248L. All three of the fHbp ID 55 mutants had significantly decreased binding of fH (FIG. 8A). The mutants had preserved conformational integrity as judged by binding of murine anti-fHbp monoclonal antibody JAR 41 (FIG. 8B).

FIGS. 8A and 8B. fH binding of fHbp ID 55 mutants. A. Binding of fH to immobilized fHbp ID 55 mutants by ELISA. The experiment was performed as described in the legend to FIG. 2. The mean and range for two to four replicates are shown. B. Concentration dependent binding of anti-fHbp monoclonal antibody (mAb) JAR 41 indicated that the recombinant fHbps were present in similar amounts in the wells of the microtiter plate and had preserved conformation in the region of the epitope recognized by JAR 41 (N-terminal domain; Vu et al. (2012) Sci. Reports, supra).

The secondary antibody was goat anti-mouse IgG conjugated to alkaline phosphatase (Sigma).

Figure 9:
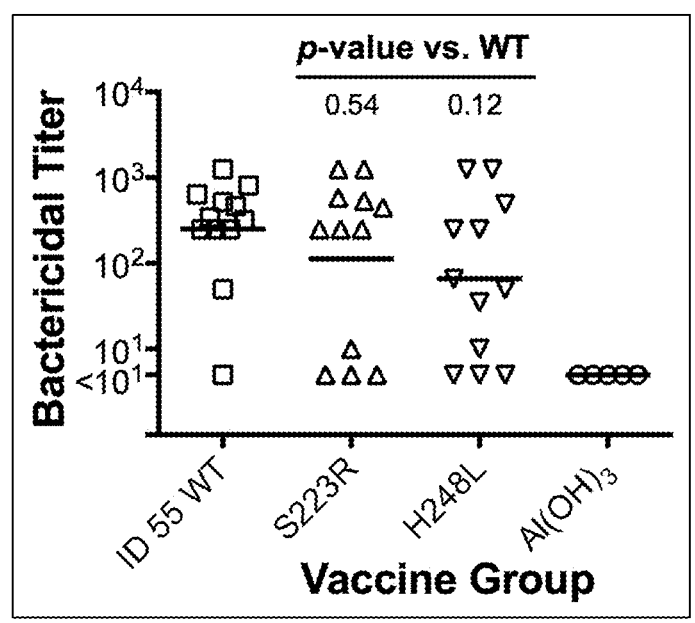
FIG. 9 depicts bactericidal activity of serum from wild-type mice immunized with fHbp ID 55 mutants. Each symbol represents the titer of an individual mouse, and the horizontal bars represent the geometric mean titers.

FIG. 9. Bactericidal antibody responses to fHbp ID 55 mutants in wild-type mice. Groups of 12 mice were immunized and the serum bactericidal antibody responses were determined as described above for FIG. 5A. Bactericidal activity was measured against a mutant of strain H44/76 that expresses fHbp ID 55.

Figures 10A, 10B:
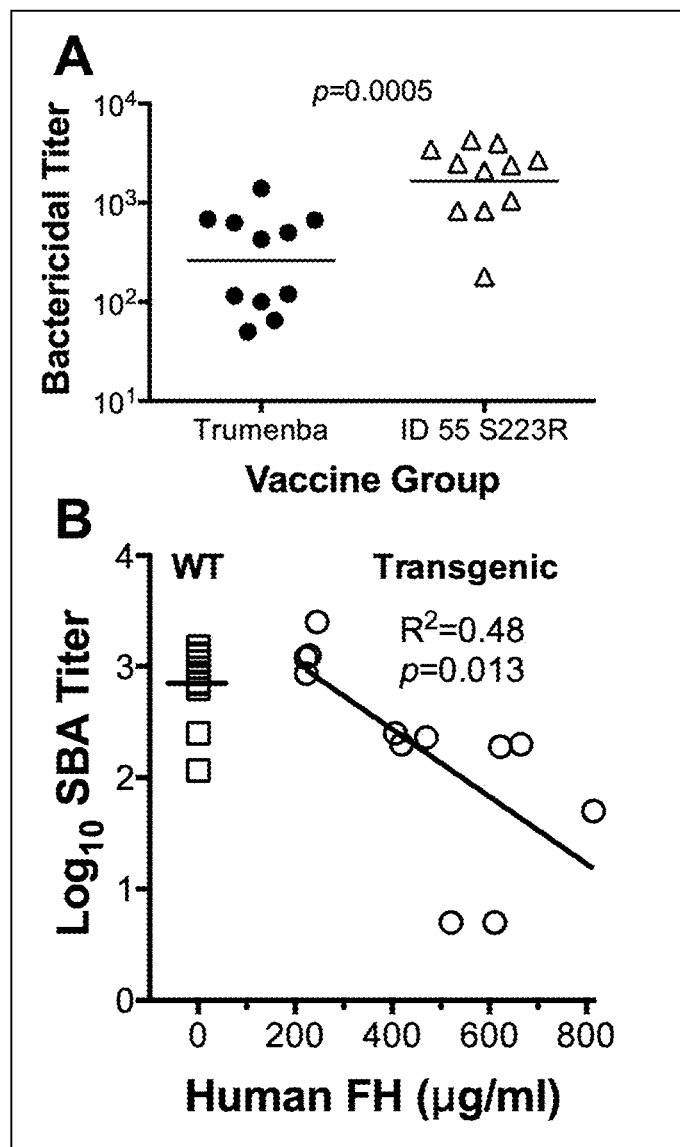
FIGS. 10A and 10B depict bactericidal activity of serum from mice immunized with fHbp ID 55.

FIG. 10A, Bactericidal antibody responses of human fH transgenic mice to fHbp ID 55 S223R mutant. Groups of 11 to 12 transgenic mice were immunized with three doses of purified recombinant fHbp (12 μg per dose) or one-tenth of a human dose of the licensed Trumenba (Pfizer) vaccine containing a total of 12 μg fHbp. The transgenic mice were immunized and the serum bactericidal antibody responses were determined as described above for FIG. 5B. FIG. 10B, Bactericidal antibody responses to Trumenba in wild-type and human fH transgenic mice in relation to serum human fH concentrations. Serum human fH concentrations were measured by ELISA as described previously (Beernink et al. (2011) Journal of Immunology 186(6):3606-14).

Example 3: Identification and Characterization of fHbp ID 22 Mutants

Materials and Methods

The experiments were performed as described in Example 1.

Results

An independent search for random fHbp mutants with decreased binding of fH was performed using fHbp ID 22, which is in variant group 2 (sub-family A). This screen resulted in six promising new mutants (FIG. 17). fH binding to the ID 22 wild-type and previously described D211A mutant by ELISA is shown in FIG. 11A. fH binding to the six new mutant ID 22 proteins is shown in FIG. 11B.

Figures 11A, 11B, 11C, 11D:
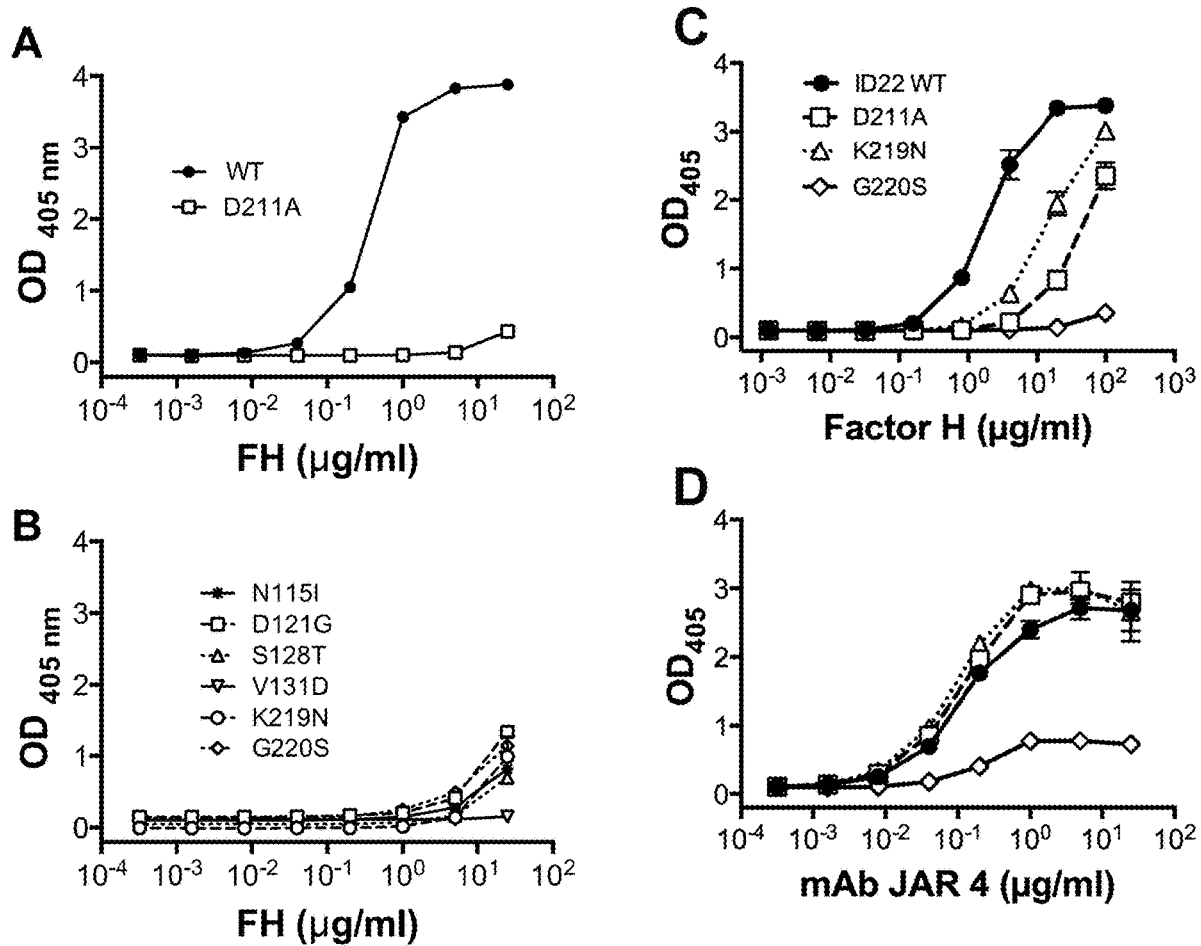
FIGS. 11A-11D depict characterization of fHbp ID 22 mutants.

FIGS. 11A-11D. fH binding of fHbp ID 22 library mutants. FIG. 11A, Positive control fHbp ID 22 wild-type (WT) protein with high binding of human fH. Negative control fHbp ID 22 D211A mutant with low binding of fH. FIG. 11B, New fHbp ID 22 mutants with decreased binding of fH. All of the mutants showed low binding and V131D showed very low binding similar to D211A. The experiment was performed as described in the legend to FIG. 2. The mean and range of two to four replicates are shown. FIG. 11C, fH binding of a subset of fHbp ID 22 mutants at fH concentrations up to 100 μg/ml. FIG. 11D, Binding of anti-fHbp monoclonal antibody JAR 4 to a subset of the mutants (same symbols used as in FIG. 11C). New mutant K219N retains JAR 4 binding, whereas G220S mutant has decreased binding of JAR 4. All of the mutants had normal binding of another anti-fHbp monoclonal antibody JAR 31 (data not shown). The mean and standard deviation of duplicate measurements are shown.

Bactericidal antibody responses of wild-type CD-1 mice to the new mutants V131D and K219N, along with the control wild-type ID 22 protein and the previously characterized mutant D211A are shown in FIG. 12.

Figures 12A, 12B:
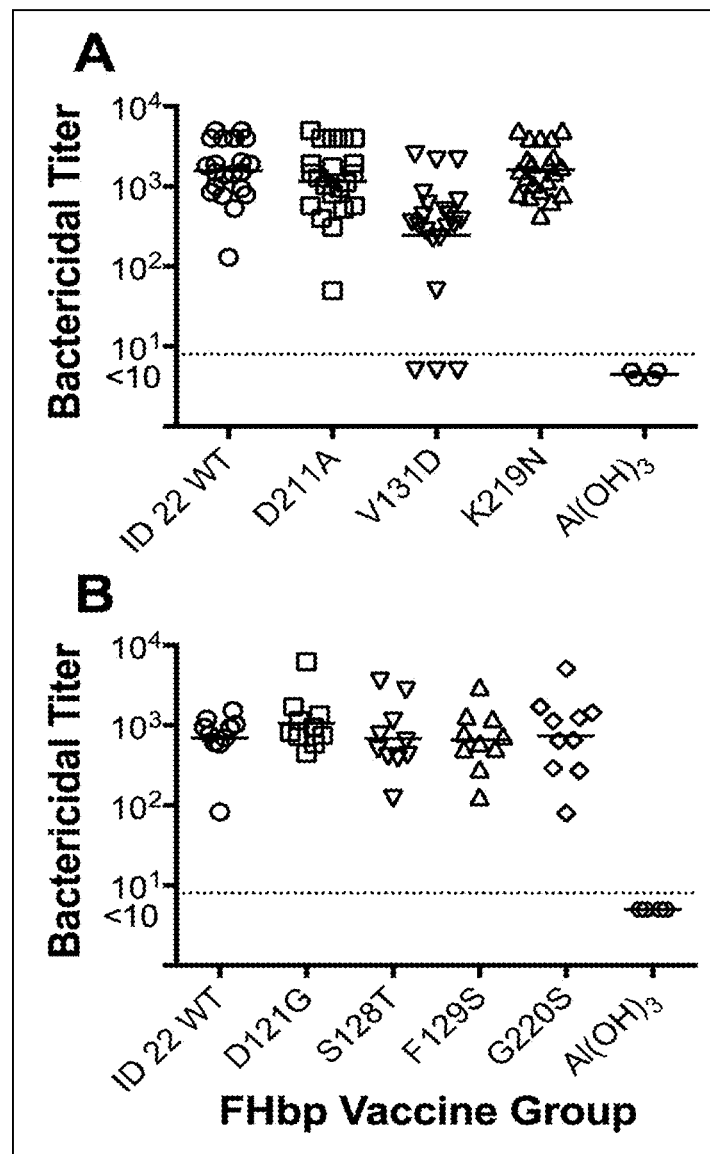
FIGS. 12A and 12B show bactericidal activity of serum from mice immunized with fHbp ID 22 mutants. Each symbol represents the titer of an individual mouse, and the horizontal bars represent the geometric mean titers.

FIGS. 12A-12B. Bactericidal antibody responses to fHbp ID 22 library mutants in wild-type mice. Library mutants with low binding of human fH were selected for immunization. Groups of 10 to 21 mice were immunized with two doses of purified recombinant fHbp (10 μg per dose) given at three-week intervals. Serum was obtained three weeks after the second dose. Serum bactericidal activity was measured using IgG depleted human serum as the complement source and serogroup B strain CH597 as the test strain. This strain expresses fHbp ID 23, which closely matches the control fHbp ID 22 WT vaccine. FIG. 12A, Experiment testing new mutants V131D and K219N. The D211A mutant was used as a control mutant fHbp vaccine that did not decrease immunogenicity. Each symbol represents the titer of an individual mouse, and the horizontal bars represent the geometric mean titers. FIG. 12B, Second experiment testing new mutants D121G, S128T, F129S, and G220S. No significant loss of immunogenicity was observed for the new mutant fHbps, except for a modest loss for V131D.

Figure 13:
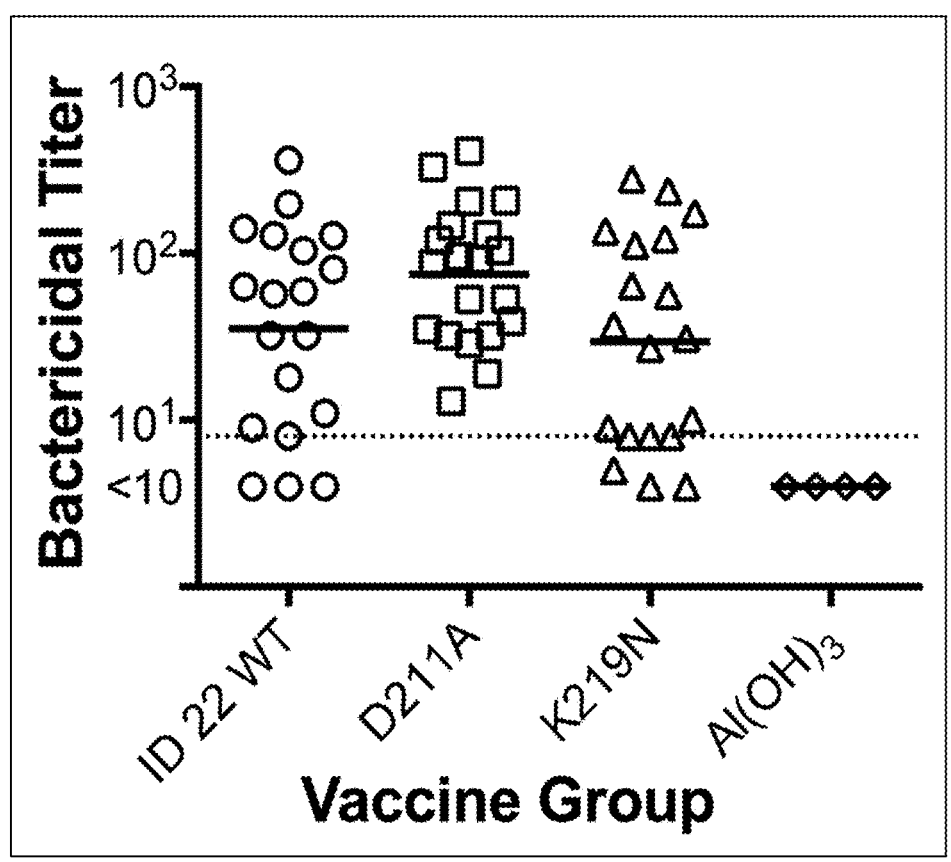
FIG. 13 depicts bactericidal activity of serum from human fH transgenic mice immunized with fHbp ID 22 mutants.

FIG. 13. Bactericidal antibody responses to fHbp ID 22 library mutant K219N in human fH transgenic mice. The control mutant D211A gave higher responses and the K219N mutant gave responses similar to the fHbp ID 22 wild-type (WT) antigen.

Figure 14:
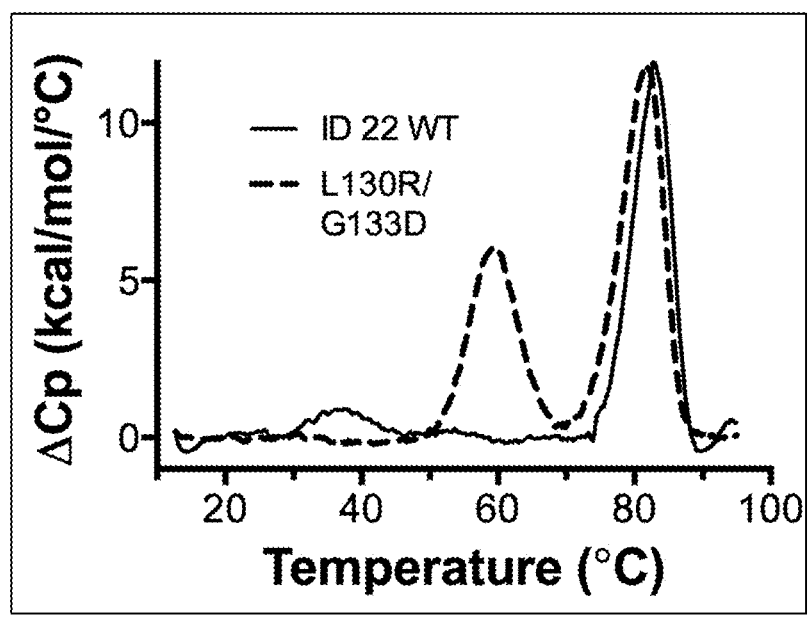
FIG. 14 depicts thermal unfolding of fHbp ID 22 wild-type (WT) and L130R/G133D double mutant measured by differential scanning microcalorimetry.

FIG. 14. Thermal stability of fHbp ID 22 measured by differential scanning microcalorimetry. The fHbp ID 22 wild-type (WT, solid line) undergoes unfolding transitions at 38 (N-terminal) and 81° C. (C-terminal domain). An fHbp ID 22 L130R/G133D double mutant exhibits 19° C. higher thermal stability for the N-terminal domain compared with that of the ID 22 WT.

Figures 15A, 15B:
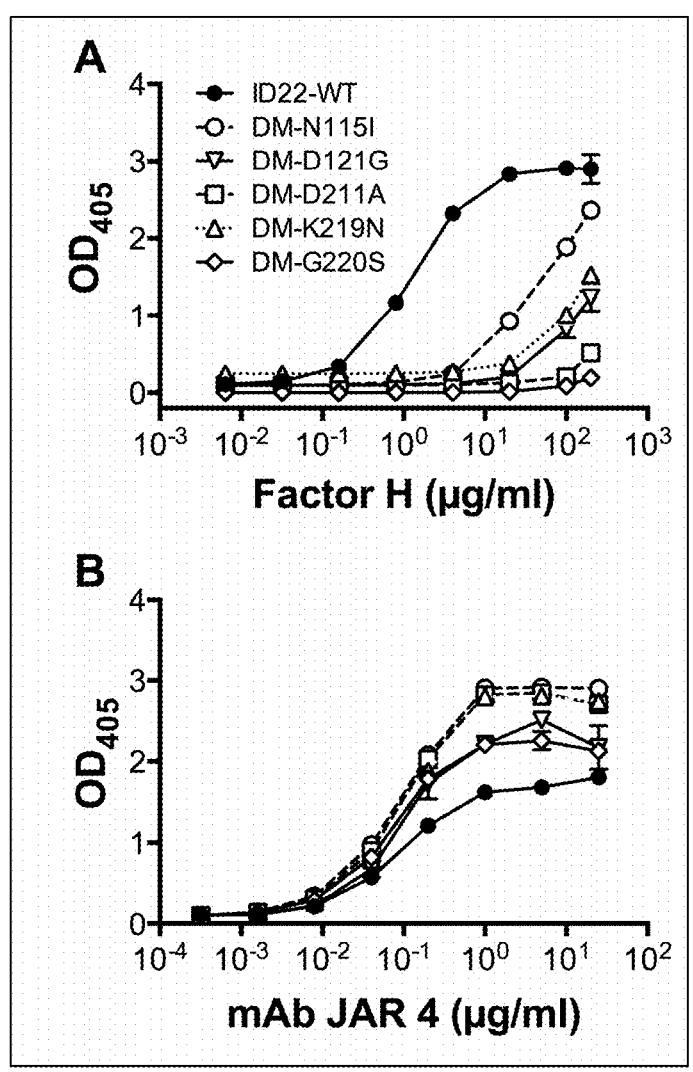
FIG. 15A and FIG. 15B depict characterization of fHbp ID 22 triple mutants.

FIGS. 15A-15B. fHbp ID 22 triple mutants combining stabilizing substitutions L130R and G133D (double mutant, DM) with library derived mutants to decrease fH binding. A, fH binding to fHbp ID 22 triple mutants. B, Control murine anti-fHbp monoclonal antibody (mAb) JAR 4 binding (same symbols as in panel A. All of the stabilized mutants bind JAR 4 better than the fHbp ID 22 WT.

Figure 16:
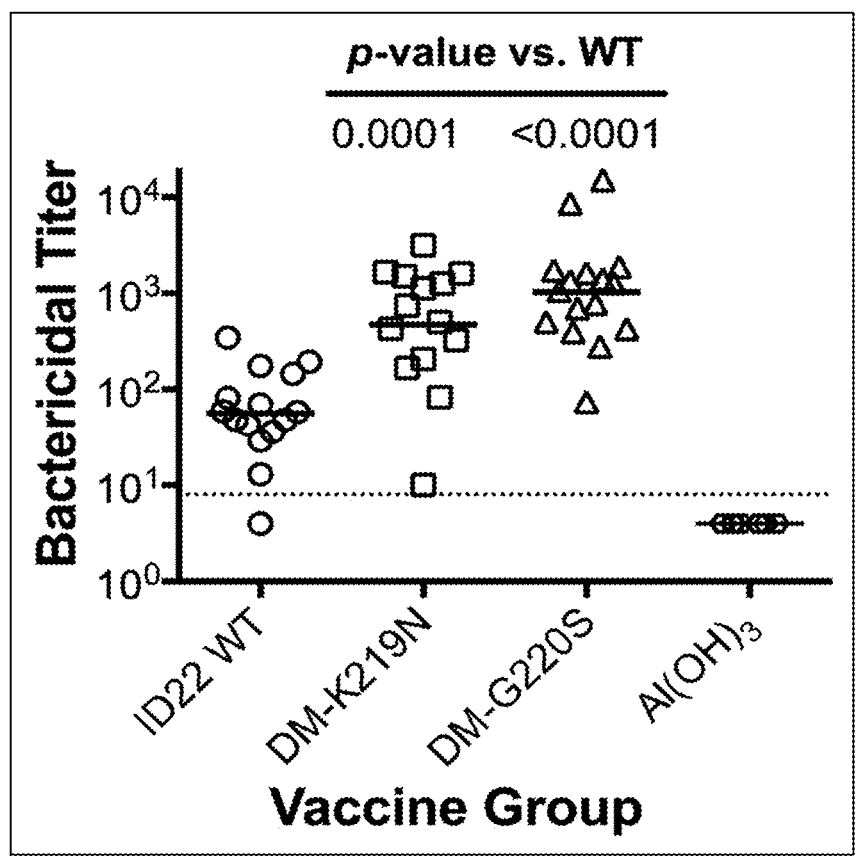
FIG. 16 depicts bactericidal activity of serum from human fH transgenic mice immunized with fHbp ID 22 triple mutants. DM refers to L130R/G133D double mutant.

FIG. 16. Bactericidal antibody responses to fHbp ID 22 triple mutants in human fH transgenic mice. The two mutants tested combine stability double mutant (DM) with K219N and G220S, respectively. The triple mutants elicited eight- and 18-fold higher responses than the control ID 22 WT antigen.

A summary of exemplary fHbp ID 1 and ID 22 mutants described above is presented in the table in FIG. 17.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A variant factor H binding protein (fHbp), wherein the variant fHbp comprises:
   an amino acid sequence at least 85% identical to the entire length of the amino acid sequence of fHbp ID 22 set forth in SEQ ID NO:2; and
   an amino acid substitution of glycine at position with serine 220 (G220S), relative to the amino acid sequence set forth in SEQ ID NO:2, wherein the numbering of G220 is based on the numbering of amino acid residues in SEQ ID NO:1.

2. The variant fHbp of claim 1, comprising the amino acid substitutions G220S, L130R and G133D.

3. The variant fHbp of claim 1, wherein the variant fHbp differs from the sequence of SEQ ID NO: 2 by 1, 2, 3, 4, 5, 6, 7, 8, 9, or 10 amino acids.

4. The variant fHbp of claim 1, wherein the amino acid sequence of the variant fHbp is at least 95% identical to the entire length of the amino acid sequence set forth in SEQ ID NO:2.

5. The variant fHbp of claim 1, wherein the amino acid sequence of the variant fHbp is at least 98% identical to the entire length of the amino acid sequence set forth in SEQ ID NO:2.

6. An immunogenic composition comprising:
   a) the variant fHbp according to claim 1; and
   b) a pharmaceutically acceptable excipient.

7. The immunogenic composition of claim 6, wherein the variant fHbp is in a vesicle preparation prepared from a *Neisseria meningitidis* strain.

8. The immunogenic composition of claim 6, wherein the pharmaceutically acceptable excipient comprises an adjuvant.

9. The immunogenic composition of claim 8, wherein the adjuvant is aluminum phosphate.

10. The immunogenic composition of claim 8, wherein the adjuvant is aluminum hydroxide.

11. The immunogenic composition of claim 7, wherein the pharmaceutically acceptable excipient comprises an adjuvant.

12. The immunogenic composition of claim 11, wherein the adjuvant is aluminum phosphate.

13. The immunogenic composition of claim 11, wherein the adjuvant is aluminum hydroxide.

14. The immunogenic composition of claim 6, further comprising Neisserial surface protein A.

15. A method of eliciting an antibody response to *Neisseria meningitidis* in a mammal, the method comprising administering to the mammal an immunologically effective amount of the immunogenic composition of claim 6.

16. The method of claim 15, wherein the mammal is a human.

17. A method of eliciting an antibody response to *Neisseria meningitidis* in a mammal, the method comprising administering to the mammal an immunologically effective amount of the immunogenic composition of claim 7.

18. The method of claim 17, wherein the mammal is a human.

* * * * *

SEQUENCE LISTING

<160> NUMBER OF SEQ ID NOS: 28

<210> SEQ ID NO 1
<211> LENGTH: 255
<212> TYPE: PRT

<213> ORGANISM: Neisseria meningitidis

<400> SEQUENCE: 1

| | | | | | | | | | | | | | | | |
|---|---|---|---|---|---|---|---|---|---|---|

```
            100                 105                 110
Lys Ile Asn Asn Pro Asp Lys Ile Asp Ser Leu Ile Asn Gln Arg Ser
            115                 120                 125

Phe Leu Val Ser Gly Leu Gly Gly Glu His Thr Ala Phe Asn Gln Leu
            130                 135             140

Pro Ser Gly Lys Ala Glu Tyr His Gly Lys Ala Phe Ser Ser Asp Asp
145                 150                 155                 160

Pro Asn Gly Arg Leu His Tyr Ser Ile Asp Phe Thr Lys Lys Gln Gly
                165                 170                 175

Tyr Gly Arg Ile Glu His Leu Lys Thr Pro Glu Gln Asn Val Glu Leu
            180                 185                 190

Ala Ser Ala Glu Leu Lys Ala Asp Glu Lys Ser His Ala Val Ile Leu
            195                 200                 205

Gly Asp Thr Arg Tyr Gly Glu Glu Lys Gly Thr Tyr His Leu Ala
            210                 215                 220

Leu Phe Gly Asp Arg Ala Gln Glu Ile Ala Gly Ser Ala Thr Val Lys
225                 230                 235                 240

Ile Arg Glu Lys Val His Glu Ile Gly Ile Ala Gly Lys Gln
                245                 250

<210> SEQ ID NO 3
<211> LENGTH: 260
<212> TYPE: PRT
<213> ORGANISM: Neisseria meningitidis

<400> SEQUENCE: 3

Cys Ser Ser Gly Gly Gly Ser Gly Gly Gly Val Thr Ala Asp
1               5                   10                  15

Ile Gly Thr Gly Leu Ala Asp Ala Leu Thr Ala Pro Leu Asp His Lys
                20                  25                  30

Asp Lys Gly Leu Lys Ser Leu Thr Leu Glu Asp Ser Ile Ser Gln Asn
            35                  40                  45

Gly Thr Leu Thr Leu Ser Ala Gln Gly Ala Glu Lys Thr Tyr Gly Asn
        50                  55                  60

Gly Asp Ser Leu Asn Thr Gly Lys Leu Lys Asn Asp Lys Val Ser Arg
65                  70                  75                  80

Phe Asp Phe Ile Arg Gln Ile Glu Val Asp Gly Gln Leu Ile Thr Leu
                85                  90                  95

Glu Ser Gly Glu Phe Gln Val Tyr Lys Gln Ser His Ser Ala Leu Thr
            100                 105                 110

Ala Leu Gln Thr Glu Gln Glu Gln Asp Pro Glu His Ser Glu Lys Met
            115                 120                 125

Val Ala Lys Arg Arg Phe Arg Ile Gly Asp Ile Ala Gly Glu His Thr
            130                 135                 140

Ser Phe Asp Lys Leu Pro Lys Asp Val Met Ala Thr Tyr Arg Gly Thr
145                 150                 155                 160

Ala Phe Gly Ser Asp Asp Ala Gly Gly Lys Leu Thr Tyr Thr Ile Asp
                165                 170                 175

Phe Ala Ala Lys Gln Gly His Gly Lys Ile Glu His Leu Lys Ser Pro
            180                 185                 190

Glu Leu Asn Val Asp Leu Ala Val Ala Tyr Ile Lys Pro Asp Glu Lys
            195                 200                 205

His His Ala Val Ile Ser Gly Ser Val Leu Tyr Asn Gln Asp Glu Lys
        210                 215                 220
```

```
Gly Ser Tyr Ser Leu Gly Ile Phe Gly Glu Lys Ala Gln Glu Val Ala
225                 230                 235                 240

Gly Ser Ala Glu Val Glu Thr Ala Asn Gly Ile His His Ile Gly Leu
            245                 250                 255

Ala Ala Lys Gln
        260

<210> SEQ ID NO 4
<211> LENGTH: 1231
<212> TYPE: PRT
<213> ORGANISM: Homo sapiens

<400> SEQUENCE: 4

Met Arg Leu Leu Ala Lys Ile Ile Cys Leu Met Leu Trp Ala Ile Cys
1               5                   10                  15

Val Ala Glu Asp Cys Asn Glu Leu Pro Pro Arg Arg Asn Thr Glu Ile
                20                  25                  30

Leu Thr Gly Ser Trp Ser Asp Gln Thr Tyr Pro Glu Gly Thr Gln Ala
            35                  40                  45

Ile Tyr Lys Cys Arg Pro Gly Tyr Arg Ser Leu Gly Asn Val Ile Met
        50                  55                  60

Val Cys Arg Lys Gly Glu Trp Val Ala Leu Asn Pro Leu Arg Lys Cys
65                  70                  75                  80

Gln Lys Arg Pro Cys Gly His Pro Gly Asp Thr Pro Phe Gly Thr Phe
                85                  90                  95

Thr Leu Thr Gly Gly Asn Val Phe Glu Tyr Gly Val Lys Ala Val Tyr
            100                 105                 110

Thr Cys Asn Glu Gly Tyr Gln Leu Leu Gly Glu Ile Asn Tyr Arg Glu
        115                 120                 125

Cys Asp Thr Asp Gly Trp Thr Asn Asp Ile Pro Ile Cys Glu Val Val
    130                 135                 140

Lys Cys Leu Pro Val Thr Ala Pro Glu Asn Gly Lys Ile Val Ser Ser
145                 150                 155                 160

Ala Met Glu Pro Asp Arg Glu Tyr His Phe Gly Gln Ala Val Arg Phe
                165                 170                 175

Val Cys Asn Ser Gly Tyr Lys Ile Glu Gly Asp Glu Glu Met His Cys
            180                 185                 190

Ser Asp Asp Gly Phe Trp Ser Lys Glu Lys Pro Lys Cys Val Glu Ile
        195                 200                 205

Ser Cys Lys Ser Pro Asp Val Ile Asn Gly Ser Pro Ile Ser Gln Lys
    210                 215                 220

Ile Ile Tyr Lys Glu Asn Glu Arg Phe Gln Tyr Lys Cys Asn Met Gly
225                 230                 235                 240

Tyr Glu Tyr Ser Glu Arg Gly Asp Ala Val Cys Thr Glu Ser Gly Trp
                245                 250                 255

Arg Pro Leu Pro Ser Cys Glu Glu Lys Ser Cys Asp Asn Pro Tyr Ile
            260                 265                 270

Pro Asn Gly Asp Tyr Ser Pro Leu Arg Ile Lys His Arg Thr Gly Asp
        275                 280                 285

Glu Ile Thr Tyr Gln Cys Arg Asn Gly Phe Tyr Pro Ala Thr Arg Gly
    290                 295                 300

Asn Thr Ala Lys Cys Thr Ser Thr Gly Trp Ile Pro Ala Pro Arg Cys
305                 310                 315                 320

Thr Leu Lys Pro Cys Asp Tyr Pro Asp Ile Lys His Gly Gly Leu Tyr
                325                 330                 335
```

```
His Glu Asn Met Arg Arg Pro Tyr Phe Pro Val Ala Val Gly Lys Tyr
                340                 345                 350

Tyr Ser Tyr Tyr Cys Asp Glu His Phe Glu Thr Pro Ser Gly Ser Tyr
        355                 360                 365

Trp Asp His Ile His Cys Thr Gln Asp Gly Trp Ser Pro Ala Val Pro
370                 375                 380

Cys Leu Arg Lys Cys Tyr Phe Pro Tyr Leu Glu Asn Gly Tyr Asn Gln
385                 390                 395                 400

Asn Tyr Gly Arg Lys Phe Val Gln Gly Lys Ser Ile Asp Val Ala Cys
            405                 410                 415

His Pro Gly Tyr Ala Leu Pro Lys Ala Gln Thr Thr Val Thr Cys Met
                420                 425                 430

Glu Asn Gly Trp Ser Pro Thr Pro Arg Cys Ile Arg Val Lys Thr Cys
            435                 440                 445

Ser Lys Ser Ser Ile Asp Ile Glu Asn Gly Phe Ile Ser Glu Ser Gln
        450                 455                 460

Tyr Thr Tyr Ala Leu Lys Glu Lys Ala Lys Tyr Gln Cys Lys Leu Gly
465                 470                 475                 480

Tyr Val Thr Ala Asp Gly Glu Thr Ser Gly Ser Ile Thr Cys Gly Lys
                485                 490                 495

Asp Gly Trp Ser Ala Gln Pro Thr Cys Ile Lys Ser Cys Asp Ile Pro
            500                 505                 510

Val Phe Met Asn Ala Arg Thr Lys Asn Asp Phe Thr Trp Phe Lys Leu
        515                 520                 525

Asn Asp Thr Leu Asp Tyr Glu Cys His Asp Gly Tyr Glu Ser Asn Thr
        530                 535                 540

Gly Ser Thr Thr Gly Ser Ile Val Cys Gly Tyr Asn Gly Trp Ser Asp
545                 550                 555                 560

Leu Pro Ile Cys Tyr Glu Arg Glu Cys Glu Leu Pro Lys Ile Asp Val
            565                 570                 575

His Leu Val Pro Asp Arg Lys Lys Asp Gln Tyr Lys Val Gly Glu Val
            580                 585                 590

Leu Lys Phe Ser Cys Lys Pro Gly Phe Thr Ile Val Gly Pro Asn Ser
        595                 600                 605

Val Gln Cys Tyr His Phe Gly Leu Ser Pro Asp Leu Pro Ile Cys Lys
        610                 615                 620

Glu Gln Val Gln Ser Cys Gly Pro Pro Glu Leu Leu Asn Gly Asn
625                 630                 635                 640

Val Lys Glu Lys Thr Lys Glu Glu Tyr Gly His Ser Glu Val Val Glu
                645                 650                 655

Tyr Tyr Cys Asn Pro Arg Phe Leu Met Lys Gly Pro Asn Lys Ile Gln
            660                 665                 670

Cys Val Asp Gly Glu Trp Thr Thr Leu Pro Val Cys Ile Val Glu Glu
            675                 680                 685

Ser Thr Cys Gly Asp Ile Pro Glu Leu Glu His Gly Trp Ala Gln Leu
        690                 695                 700

Ser Ser Pro Pro Tyr Tyr Tyr Gly Asp Ser Val Glu Phe Asn Cys Ser
705                 710                 715                 720

Glu Ser Phe Thr Met Ile Gly His Arg Ser Ile Thr Cys Ile His Gly
                725                 730                 735

Val Trp Thr Gln Leu Pro Gln Cys Val Ala Ile Asp Lys Leu Lys Lys
            740                 745                 750
```

-continued

```
Cys Lys Ser Ser Asn Leu Ile Ile Leu Glu Glu His Leu Lys Asn Lys
        755                 760                 765

Lys Glu Phe Asp His Asn Ser Asn Ile Arg Tyr Arg Cys Arg Gly Lys
770                 775                 780

Glu Gly Trp Ile His Thr Val Cys Ile Asn Gly Arg Trp Asp Pro Glu
785                 790                 795                 800

Val Asn Cys Ser Met Ala Gln Ile Gln Leu Cys Pro Pro Pro Gln
                    805                 810                 815

Ile Pro Asn Ser His Asn Met Thr Thr Thr Leu Asn Tyr Arg Asp Gly
                    820                 825                 830

Glu Lys Val Ser Val Leu Cys Gln Glu Asn Tyr Leu Ile Gln Glu Gly
                    835                 840                 845

Glu Glu Ile Thr Cys Lys Asp Gly Arg Trp Gln Ser Ile Pro Leu Cys
850                 855                 860

Val Glu Lys Ile Pro Cys Ser Gln Pro Pro Gln Ile Glu His Gly Thr
865                 870                 875                 880

Ile Asn Ser Ser Arg Ser Ser Gln Glu Ser Tyr Ala His Gly Thr Lys
                    885                 890                 895

Leu Ser Tyr Thr Cys Glu Gly Gly Phe Arg Ile Ser Glu Glu Asn Glu
                    900                 905                 910

Thr Thr Cys Tyr Met Gly Lys Trp Ser Ser Pro Pro Gln Cys Glu Gly
            915                 920                 925

Leu Pro Cys Lys Ser Pro Pro Glu Ile Ser His Gly Val Val Ala His
930                 935                 940

Met Ser Asp Ser Tyr Gln Tyr Gly Glu Glu Val Thr Tyr Lys Cys Phe
945                 950                 955                 960

Glu Gly Phe Gly Ile Asp Gly Pro Ala Ile Ala Lys Cys Leu Gly Glu
                    965                 970                 975

Lys Trp Ser His Pro Pro Ser Cys Ile Lys Thr Asp Cys Leu Ser Leu
                    980                 985                 990

Pro Ser Phe Glu Asn Ala Ile Pro Met Gly Glu Lys Lys Asp Val Tyr
            995                 1000                1005

Lys Ala Gly Glu Gln Val Thr Tyr Thr Cys Ala Thr Tyr Tyr Lys
    1010                1015                1020

Met Asp Gly Ala Ser Asn Val Thr Cys Ile Asn Ser Arg Trp Thr
    1025                1030                1035

Gly Arg Pro Thr Cys Arg Asp Thr Ser Cys Val Asn Pro Pro Thr
    1040                1045                1050

Val Gln Asn Ala Tyr Ile Val Ser Arg Gln Met Ser Lys Tyr Pro
    1055                1060                1065

Ser Gly Glu Arg Val Arg Tyr Gln Cys Arg Ser Pro Tyr Glu Met
    1070                1075                1080

Phe Gly Asp Glu Glu Val Met Cys Leu Asn Gly Asn Trp Thr Glu
    1085                1090                1095

Pro Pro Gln Cys Lys Asp Ser Thr Gly Lys Cys Gly Pro Pro Pro
    1100                1105                1110

Pro Ile Asp Asn Gly Asp Ile Thr Ser Phe Pro Leu Ser Val Tyr
    1115                1120                1125

Ala Pro Ala Ser Ser Val Glu Tyr Gln Cys Gln Asn Leu Tyr Gln
    1130                1135                1140

Leu Glu Gly Asn Lys Arg Ile Thr Cys Arg Asn Gly Gln Trp Ser
    1145                1150                1155

Glu Pro Pro Lys Cys Leu His Pro Cys Val Ile Ser Arg Glu Ile
```

```
            1160                1165                1170

Met Glu Asn Tyr Asn Ile Ala Leu Arg Trp Thr Ala Lys Gln Lys
    1175                1180                1185

Leu Tyr Ser Arg Thr Gly Glu Ser Val Glu Phe Val Cys Lys Arg
    1190                1195                1200

Gly Tyr Arg Leu Ser Ser Arg Ser His Thr Leu Arg Thr Thr Cys
    1205                1210                1215

Trp Asp Gly Lys Leu Glu Tyr Pro Thr Cys Ala Lys Arg
    1220                1225                1230

<210> SEQ ID NO 5
<211> LENGTH: 255
<212> TYPE: PRT
<213> ORGANISM: Artificial sequence
<220> FEATURE:
<223> OTHER INFORMATION: Synthetic polypeptide

<400> SEQUENCE: 5

Cys Ser Ser Gly Gly Gly Val Ala Ala Asp Ile Gly Ala Gly Leu
1               5                   10                  15

Ala Asp Ala Leu Thr Ala Pro Leu Asp His Lys Asp Lys Gly Leu Gln
            20                  25                  30

Ser Leu Thr Leu Asp Arg Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Val Tyr Lys Gln Ser His Ser Ala Leu Thr Ala Phe Gln Thr Glu
            100                 105                 110

Gln Ile Gln Asp Ser Glu His Ser Gly Lys Met Val Ala Lys Arg Gln
        115                 120                 125

Phe Arg Ile Gly Asp Ile Ala Gly Glu His Thr Ser Phe Asp Lys Leu
    130                 135                 140

Pro Glu Gly Gly Arg Ala Thr Tyr Arg Gly Thr Ala Phe Gly Ser Asp
145                 150                 155                 160

Asp Ala Gly Gly Lys Leu Thr Tyr Thr Ile Asp Phe Ala Ala Lys Gln
                165                 170                 175

Gly Asn Gly Lys Ile Glu His Leu Lys Ser Pro Glu Leu Asn Val Asp
            180                 185                 190

Leu Ala Ala Ala Asp Ile Lys Pro Asp Gly Lys Arg His Ala Val Ile
        195                 200                 205

Ser Gly Ser Val Leu Tyr Asn Gln Ala Glu Lys Gly Ser Tyr Ser Leu
    210                 215                 220

Gly Ile Phe Gly Gly Lys Ala Gln Glu Val Ala Gly Ser Ala Glu Val
225                 230                 235                 240

Lys Thr Val Asn Gly Ile Arg His Ile Gly Leu Ala Ala Lys Gln
                245                 250                 255

<210> SEQ ID NO 6
<211> LENGTH: 255
<212> TYPE: PRT
<213> ORGANISM: Artificial sequence
<220> FEATURE:
<223> OTHER INFORMATION: Synthetic polypeptide
```

```
<400> SEQUENCE: 6

Cys Ser Ser Gly Gly Gly Val Ala Ala Asp Ile Gly Ala Gly Leu
1               5                   10                  15

Ala Asp Ala Leu Thr Ala Pro Leu Asp His Lys Asp Lys Gly Leu Gln
            20                  25                  30

Ser Leu Thr Leu Asp Gln Ser Val Arg Lys Asn Glu Lys Leu Lys Leu
            35                  40                      45

Ala Ala Gln Gly Ala Glu Lys Thr Tyr Gly Asn Gly Asp Ser Leu Asn
    50                  55                      60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Lys Ser Gly Glu Phe
                85                  90                  95

Gln Val Tyr Lys Gln Ser His Ser Ala Leu Thr Ala Phe Gln Thr Glu
                100                 105                 110

Gln Ile Gln Asp Ser Glu His Ser Gly Lys Met Val Ala Lys Arg Gln
            115                 120                 125

Phe Arg Ile Gly Asp Ile Ala Gly Glu His Thr Ser Phe Asp Lys Leu
    130                 135                 140

Pro Glu Gly Gly Arg Ala Thr Tyr Arg Gly Thr Ala Phe Gly Ser Asp
145                 150                 155                 160

Asp Ala Gly Gly Lys Leu Thr Tyr Thr Ile Asp Phe Ala Ala Lys Gln
                165                 170                 175

Gly Asn Gly Lys Ile Glu His Leu Lys Ser Pro Glu Leu Asn Val Asp
            180                 185                 190

Leu Ala Ala Ala Asp Ile Lys Pro Asp Gly Lys Arg His Ala Val Ile
        195                 200                 205

Ser Gly Ser Val Leu Tyr Asn Gln Ala Glu Lys Gly Ser Tyr Ser Leu
    210                 215                 220

Gly Ile Phe Gly Gly Lys Ala Gln Glu Val Ala Gly Ser Ala Glu Val
225                 230                 235                 240

Lys Thr Val Asn Gly Ile Arg His Ile Gly Leu Ala Ala Lys Gln
                245                 250                 255

<210> SEQ ID NO 7
<211> LENGTH: 255
<212> TYPE: PRT
<213> ORGANISM: Artificial sequence
<220> FEATURE:
<223> OTHER INFORMATION: Synthetic polypeptide

<400> SEQUENCE: 7

Cys Ser Ser Gly Gly Gly Val Ala Ala Asp Ile Gly Ala Gly Leu
1               5                   10                  15

Ala Asp Ala Leu Thr Ala Pro Leu Asp His Lys Asp Lys Gly Leu Gln
            20                  25                  30

Ser Leu Thr Leu Asp Gln Ser Val Arg Lys Asn Glu Lys Leu Lys Leu
            35                  40                      45

Ala Ala Gln Gly Ala Glu Lys Thr Tyr Gly Asn Gly Asp Ser Leu Asn
    50                  55                      60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95
```

Gln Val Tyr Lys Gln Ser His Ser Ala Leu Thr Ala Phe Gln Thr Glu
                100                 105                 110

Gln Ile Gln Asp Ser Glu His Ser Gly Lys Met Val Ala Lys Arg Gln
            115                 120                 125

Phe Gly Ile Gly Asp Ile Ala Gly Glu His Thr Ser Phe Asp Lys Leu
        130                 135                 140

Pro Glu Gly Gly Arg Ala Thr Tyr Arg Gly Thr Ala Phe Gly Ser Asp
145                 150                 155                 160

Asp Ala Gly Gly Lys Leu Thr Tyr Thr Ile Asp Phe Ala Ala Lys Gln
                165                 170                 175

Gly Asn Gly Lys Ile Glu His Leu Lys Ser Pro Glu Leu Asn Val Asp
            180                 185                 190

Leu Ala Ala Ala Asp Ile Lys Pro Asp Gly Lys Arg His Ala Val Ile
        195                 200                 205

Ser Gly Ser Val Leu Tyr Asn Gln Ala Glu Lys Gly Ser Tyr Ser Leu
    210                 215                 220

Gly Ile Phe Gly Lys Ala Gln Glu Val Ala Gly Ser Ala Glu Val
225                 230                 235                 240

Lys Thr Val Asn Gly Ile Arg His Ile Gly Leu Ala Ala Lys Gln
                245                 250                 255

<210> SEQ ID NO 8
<211> LENGTH: 255
<212> TYPE: PRT
<213> ORGANISM: Artificial sequence
<220> FEATURE:
<223> OTHER INFORMATION: Synthetic polypeptide

<400> SEQUENCE: 8

Cys Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Gly Leu Gln
                20                  25                  30

Ser Leu Thr Leu Asp Gln Ser Val Arg Lys Asn Glu Lys Leu Lys Leu
            35                  40                  45

Ala Ala Gln Gly Ala Glu Lys Thr Tyr Gly Asn Gly Asp Ser Leu Asn
        50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Val Tyr Lys Gln Ser His Ser Ala Leu Thr Ala Phe Gln Thr Glu
                100                 105                 110

Gln Ile Gln Asp Ser Glu His Ser Gly Lys Met Val Ala Lys Arg Gln
            115                 120                 125

Phe Arg Ile Gly Asp Ile Ala Gly Glu His Thr Ser Phe Asp Lys Leu
        130                 135                 140

Pro Glu Gly Gly Arg Ala Thr Tyr Arg Gly Thr Ala Phe Gly Ser Asp
145                 150                 155                 160

Asp Ala Gly Gly Lys Leu Thr Tyr Thr Ile Asp Phe Ala Ala Lys Gln
                165                 170                 175

Gly Asn Gly Lys Ile Glu His Leu Lys Ser Pro Glu Leu Asn Val Asp
            180                 185                 190

Leu Ala Ala Ala Asp Ile Lys Pro Asp Gly Lys Arg His Ala Val Ile
        195                 200                 205

```
Ser Gly Ser Val Leu Tyr Asn Gln Ala Glu Lys Gly Ser Tyr Arg Leu
    210                 215                 220

Gly Ile Phe Gly Gly Lys Ala Gln Glu Val Ala Gly Ser Ala Glu Val
225                 230                 235                 240

Lys Thr Val Asn Gly Ile Arg His Ile Gly Leu Ala Ala Lys Gln
                245                 250                 255
```

<210> SEQ ID NO 9
<211> LENGTH: 255
<212> TYPE: PRT
<213> ORGANISM: Artificial sequence
<220> FEATURE:
<223> OTHER INFORMATION: Synthetic polypeptide

<400> SEQUENCE: 9

```
Cys Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Gly Leu Gln
                20                  25                  30

Ser Leu Thr Leu Asp Gln Ser Val Arg Lys Asn Glu Lys Leu Lys Leu
            35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Val Tyr Lys Gln Ser His Ser Ala Leu Thr Ala Phe Gln Thr Glu
            100                 105                 110

Gln Ile Gln Asp Ser Glu His Ser Gly Lys Met Val Ala Lys Arg Gln
    115                 120                 125

Phe Arg Ile Gly Asp Ile Ala Gly Glu His Thr Ser Phe Asp Lys Leu
130                 135                 140

Pro Glu Gly Gly Arg Ala Thr Tyr Arg Gly Thr Ala Phe Gly Ser Asp
145                 150                 155                 160

Asp Ala Gly Gly Lys Leu Thr Tyr Thr Ile Asp Phe Ala Ala Lys Gln
                165                 170                 175

Gly Asn Gly Lys Ile Glu His Leu Lys Ser Pro Glu Leu Asn Val Asp
            180                 185                 190

Leu Ala Ala Ala Asp Ile Lys Pro Asp Gly Lys Arg His Ala Val Ile
    195                 200                 205

Ser Gly Ser Val Leu Tyr Asn Gln Ala Glu Lys Gly Ser Tyr Ser Leu
    210                 215                 220

Gly Ile Phe Gly Gly Lys Ala Gln Glu Val Ala Gly Ser Ala Glu Val
225                 230                 235                 240

Lys Thr Val Asn Gly Ile Arg Leu Ile Gly Leu Ala Ala Lys Gln
                245                 250                 255
```

<210> SEQ ID NO 10
<211> LENGTH: 254
<212> TYPE: PRT
<213> ORGANISM: Artificial sequence
<220> FEATURE:
<223> OTHER INFORMATION: Synthetic polypeptide

<400> SEQUENCE: 10

```
Cys Ser Ser Gly Gly Gly Gly Val Ala Ala Asp Ile Gly Ala Gly Leu
1               5                   10                  15
```

Ala Asp Ala Leu Thr Ala Pro Leu Asp His Lys Asp Lys Ser Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Ile Tyr Lys Gln Asp His Ser Ala Val Val Ala Leu Gln Ile Glu
            100                 105                 110

Lys Ile Ile Asn Pro Asp Lys Ile Asp Ser Leu Ile Asn Gln Arg Ser
        115                 120                 125

Phe Leu Val Ser Gly Leu Gly Gly Glu His Thr Ala Phe Asn Gln Leu
    130                 135                 140

Pro Ser Gly Lys Ala Glu Tyr His Gly Lys Ala Phe Ser Ser Asp Asp
145                 150                 155                 160

Pro Asn Gly Arg Leu His Tyr Ser Ile Asp Phe Thr Lys Lys Gln Gly
                165                 170                 175

Tyr Gly Arg Ile Glu His Leu Lys Thr Pro Glu Gln Asn Val Glu Leu
            180                 185                 190

Ala Ser Ala Glu Leu Lys Ala Asp Glu Lys Ser His Ala Val Ile Leu
        195                 200                 205

Gly Asp Thr Arg Tyr Gly Glu Glu Lys Gly Thr Tyr His Leu Ala
    210                 215                 220

Leu Phe Gly Asp Arg Ala Gln Glu Ile Ala Gly Ser Ala Thr Val Lys
225                 230                 235                 240

Ile Arg Glu Lys Val His Glu Ile Gly Ile Ala Gly Lys Gln
                245                 250

<210> SEQ ID NO 11
<211> LENGTH: 254
<212> TYPE: PRT
<213> ORGANISM: Artificial sequence
<220> FEATURE:
<223> OTHER INFORMATION: Synthetic polypeptide

<400> SEQUENCE: 11

Cys Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Ser Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Ile Tyr Lys Gln Asp His Ser Ala Val Val Ala Leu Gln Ile Glu
            100                 105                 110

Lys Ile Asn Asn Pro Asp Lys Ile Gly Ser Leu Ile Asn Gln Arg Ser
        115                 120                 125

```
Phe Leu Val Ser Gly Leu Gly Gly Glu His Thr Ala Phe Asn Gln Leu
    130                 135                 140

Pro Ser Gly Lys Ala Glu Tyr His Gly Lys Ala Phe Ser Ser Asp Asp
145                 150                 155                 160

Pro Asn Gly Arg Leu His Tyr Ser Ile Asp Phe Thr Lys Lys Gln Gly
                165                 170                 175

Tyr Gly Arg Ile Glu His Leu Lys Thr Pro Glu Gln Asn Val Glu Leu
            180                 185                 190

Ala Ser Ala Glu Leu Lys Ala Asp Glu Lys Ser His Ala Val Ile Leu
        195                 200                 205

Gly Asp Thr Arg Tyr Gly Glu Glu Lys Gly Thr Tyr His Leu Ala
    210                 215                 220

Leu Phe Gly Asp Arg Ala Gln Glu Ile Ala Gly Ser Ala Thr Val Lys
225                 230                 235                 240

Ile Arg Glu Lys Val His Glu Ile Gly Ile Ala Gly Lys Gln
                245                 250

<210> SEQ ID NO 12
<211> LENGTH: 254
<212> TYPE: PRT
<213> ORGANISM: Artificial sequence
<220> FEATURE:
<223> OTHER INFORMATION: Synthetic polypeptide

<400> SEQUENCE: 12

Cys Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Ser Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Ile Tyr Lys Gln Asp His Ser Ala Val Val Ala Leu Gln Ile Glu
            100                 105                 110

Lys Ile Asn Asn Pro Asp Lys Ile Asp Ser Leu Ile Asn Gln Arg Thr
        115                 120                 125

Phe Leu Val Ser Gly Leu Gly Gly Glu His Thr Ala Phe Asn Gln Leu
    130                 135                 140

Pro Ser Gly Lys Ala Glu Tyr His Gly Lys Ala Phe Ser Ser Asp Asp
145                 150                 155                 160

Pro Asn Gly Arg Leu His Tyr Ser Ile Asp Phe Thr Lys Lys Gln Gly
                165                 170                 175

Tyr Gly Arg Ile Glu His Leu Lys Thr Pro Glu Gln Asn Val Glu Leu
            180                 185                 190

Ala Ser Ala Glu Leu Lys Ala Asp Glu Lys Ser His Ala Val Ile Leu
        195                 200                 205

Gly Asp Thr Arg Tyr Gly Glu Glu Lys Gly Thr Tyr His Leu Ala
    210                 215                 220

Leu Phe Gly Asp Arg Ala Gln Glu Ile Ala Gly Ser Ala Thr Val Lys
225                 230                 235                 240
```

Ile Arg Glu Lys Val His Glu Ile Gly Ile Ala Gly Lys Gln
            245                 250

<210> SEQ ID NO 13
<211> LENGTH: 254
<212> TYPE: PRT
<213> ORGANISM: Artificial sequence
<220> FEATURE:
<223> OTHER INFORMATION: Synthetic polypeptide

<400> SEQUENCE: 13

Cys Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Ser Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Ile Tyr Lys Gln Asp His Ser Ala Val Val Ala Leu Gln Ile Glu
            100                 105                 110

Lys Ile Asn Asn Pro Asp Lys Ile Asp Ser Leu Ile Asn Gln Arg Ser
        115                 120                 125

Phe Leu Asp Ser Gly Leu Gly Gly Glu His Thr Ala Phe Asn Gln Leu
    130                 135                 140

Pro Ser Gly Lys Ala Glu Tyr His Gly Lys Ala Phe Ser Ser Asp Asp
145                 150                 155                 160

Pro Asn Gly Arg Leu His Tyr Ser Ile Asp Phe Thr Lys Lys Gln Gly
                165                 170                 175

Tyr Gly Arg Ile Glu His Leu Lys Thr Pro Glu Gln Asn Val Glu Leu
            180                 185                 190

Ala Ser Ala Glu Leu Lys Ala Asp Glu Lys Ser His Ala Val Ile Leu
        195                 200                 205

Gly Asp Thr Arg Tyr Gly Gly Glu Glu Lys Gly Thr Tyr His Leu Ala
    210                 215                 220

Leu Phe Gly Asp Arg Ala Gln Glu Ile Ala Gly Ser Ala Thr Val Lys
225                 230                 235                 240

Ile Arg Glu Lys Val His Glu Ile Gly Ile Ala Gly Lys Gln
                245                 250

<210> SEQ ID NO 14
<211> LENGTH: 254
<212> TYPE: PRT
<213> ORGANISM: Artificial sequence
<220> FEATURE:
<223> OTHER INFORMATION: Synthetic polypeptide

<400> SEQUENCE: 14

Cys Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Ser Leu Gln
            20                  25                  30

Ser Leu Thr Leu Asp Gln Ser Val Arg Lys Asn Glu Lys Leu Lys Leu

```
                35                  40                  45
Ala Ala Gln Gly Ala Glu Lys Thr Tyr Gly Asn Gly Asp Ser Leu Asn
 50                  55                  60

Thr Gly Lys Leu Lys Asn Asp Lys Val Ser Arg Phe Asp Phe Ile Arg
 65                  70                  75                  80

Gln Ile Glu Val Asp Gly Gln Leu Ile Thr Leu Glu Ser Gly Glu Phe
                 85                  90                  95

Gln Ile Tyr Lys Gln Asp His Ser Ala Val Val Ala Leu Gln Ile Glu
            100                 105                 110

Lys Ile Asn Asn Pro Asp Lys Ile Asp Ser Leu Ile Asn Gln Arg Ser
        115                 120                 125

Phe Leu Val Ser Gly Leu Gly Gly Glu His Thr Ala Phe Asn Gln Leu
130                 135                 140

Pro Ser Gly Lys Ala Glu Tyr His Gly Lys Ala Phe Ser Ser Asp Asp
145                 150                 155                 160

Pro Asn Gly Arg Leu His Tyr Ser Ile Asp Phe Thr Lys Lys Gln Gly
                165                 170                 175

Tyr Gly Arg Ile Glu His Leu Lys Thr Pro Glu Gln Asn Val Glu Leu
            180                 185                 190

Ala Ser Ala Glu Leu Lys Ala Asp Glu Lys Ser His Ala Val Ile Leu
        195                 200                 205

Gly Asp Thr Arg Tyr Gly Gly Glu Glu Asn Gly Thr Tyr His Leu Ala
210                 215                 220

Leu Phe Gly Asp Arg Ala Gln Glu Ile Ala Gly Ser Ala Thr Val Lys
225                 230                 235                 240

Ile Arg Glu Lys Val His Glu Ile Gly Ile Ala Gly Lys Gln
                245                 250

<210> SEQ ID NO 15
<211> LENGTH: 254
<212> TYPE: PRT
<213> ORGANISM: Artificial sequence
<220> FEATURE:
<223> OTHER INFORMATION: Synthetic polypeptide

<400> SEQUENCE: 15

Cys Ser Ser Gly Gly Gly Gly Val Ala Ala Asp Ile Gly Ala Gly Leu
 1               5                  10                  15

Ala Asp Ala Leu Thr Ala Pro Leu Asp His Lys Asp Lys Ser Leu Gln
                 20                  25                  30

Ser Leu Thr Leu Asp Gln Ser Val Arg Lys Asn Glu Lys Leu Lys Leu
            35                  40                  45

Ala Ala Gln Gly Ala Glu Lys Thr Tyr Gly Asn Gly Asp Ser Leu Asn
 50                  55                  60

Thr Gly Lys Leu Lys Asn Asp Lys Val Ser Arg Phe Asp Phe Ile Arg
 65                  70                  75                  80

Gln Ile Glu Val Asp Gly Gln Leu Ile Thr Leu Glu Ser Gly Glu Phe
                 85                  90                  95

Gln Ile Tyr Lys Gln Asp His Ser Ala Val Val Ala Leu Gln Ile Glu
            100                 105                 110

Lys Ile Asn Asn Pro Asp Lys Ile Asp Ser Leu Ile Asn Gln Arg Ser
        115                 120                 125

Phe Leu Val Ser Gly Leu Gly Gly Glu His Thr Ala Phe Asn Gln Leu
130                 135                 140

Pro Ser Gly Lys Ala Glu Tyr His Gly Lys Ala Phe Ser Ser Asp Asp
```

```
145                 150                 155                 160

Pro Asn Gly Arg Leu His Tyr Ser Ile Asp Phe Thr Lys Lys Gln Gly
                165                 170                 175

Tyr Gly Arg Ile Glu His Leu Lys Thr Pro Glu Gln Asn Val Glu Leu
                180                 185                 190

Ala Ser Ala Glu Leu Lys Ala Asp Glu Lys Ser His Ala Val Ile Leu
                195                 200                 205

Gly Asp Thr Arg Tyr Gly Gly Glu Lys Ser Thr Tyr His Leu Ala
210                 215                 220

Leu Phe Gly Asp Arg Ala Gln Glu Ile Ala Gly Ser Ala Thr Val Lys
225                 230                 235                 240

Ile Arg Glu Lys Val His Glu Ile Gly Ile Ala Gly Lys Gln
                245                 250
```

<210> SEQ ID NO 16
<211> LENGTH: 260
<212> TYPE: PRT
<213> ORGANISM: Artificial sequence
<220> FEATURE:
<223> OTHER INFORMATION: Synthetic polypeptide

<400> SEQUENCE: 16

```
Cys Ser Ser Gly Gly Gly Ser Gly Gly Gly Val Thr Ala Asp
1               5                   10                  15

Ile Gly Thr Gly Leu Ala Asp Ala Leu Thr Ala Pro Leu Asp His Lys
                20                  25                  30

Asp Lys Gly Leu Lys Ser Leu Thr Leu Glu Asp Ser Ile Ser Gln Asn
            35                  40                  45

Gly Thr Leu Thr Leu Ser Ala Gln Gly Ala Glu Lys Thr Tyr Gly Asn
    50                  55                  60

Gly Asp Ser Leu Asn Thr Gly Lys Leu Lys Asn Asp Lys Val Ser Arg
65                  70                  75                  80

Phe Asp Phe Ile Arg Gln Ile Glu Val Asp Gly Gln Leu Ile Thr Leu
                85                  90                  95

Lys Ser Gly Glu Phe Gln Val Tyr Lys Gln Ser His Ser Ala Leu Thr
                100                 105                 110

Ala Leu Gln Thr Glu Gln Glu Gln Asp Pro Glu His Ser Glu Lys Met
            115                 120                 125

Val Ala Lys Arg Arg Phe Arg Ile Gly Asp Ile Ala Gly Glu His Thr
    130                 135                 140

Ser Phe Asp Lys Leu Pro Lys Asp Val Met Ala Thr Tyr Arg Gly Thr
145                 150                 155                 160

Ala Phe Gly Ser Asp Asp Ala Gly Gly Lys Leu Thr Tyr Thr Ile Asp
                165                 170                 175

Phe Ala Ala Lys Gln Gly His Gly Lys Ile Glu His Leu Lys Ser Pro
                180                 185                 190

Glu Leu Asn Val Asp Leu Ala Val Ala Tyr Ile Lys Pro Asp Glu Lys
            195                 200                 205

His His Ala Val Ile Ser Gly Ser Val Leu Tyr Asn Gln Asp Glu Lys
    210                 215                 220

Gly Ser Tyr Ser Leu Gly Ile Phe Gly Glu Lys Ala Gln Glu Val Ala
225                 230                 235                 240

Gly Ser Ala Glu Val Glu Thr Ala Asn Gly Ile His His Ile Gly Leu
                245                 250                 255

Ala Ala Lys Gln
```

<210> SEQ ID NO 17
<211> LENGTH: 260
<212> TYPE: PRT
<213> ORGANISM: Artificial sequence
<220> FEATURE:
<223> OTHER INFORMATION: Synthetic polypeptide

<400> SEQUENCE: 17

```
Cys Ser Ser Gly Gly Gly Ser Gly Gly Gly Gly Val Thr Ala Asp
1               5                   10                  15

Ile Gly Thr Gly Leu Ala Asp Ala Leu Thr Ala Pro Leu Asp His Lys
            20                  25                  30

Asp Lys Gly Leu Lys Ser Leu Thr Leu Glu Asp Ser Ile Ser Gln Asn
        35                  40                  45

Gly Thr Leu Thr Leu Ser Ala Gln Gly Ala Glu Lys Thr Tyr Gly Asn
    50                  55                  60

Gly Asp Ser Leu Asn Thr Gly Lys Leu Lys Asn Asp Lys Val Ser Arg
65                  70                  75                  80

Phe Asp Phe Ile Arg Gln Ile Glu Val Asp Gly Gln Leu Ile Thr Leu
                85                  90                  95

Glu Ser Gly Glu Phe Gln Val Tyr Lys Gln Ser His Ser Ala Leu Thr
            100                 105                 110

Ala Leu Gln Thr Glu Gln Glu Gln Asp Pro Glu His Ser Glu Lys Met
        115                 120                 125

Val Ala Lys Arg Arg Phe Arg Ile Gly Asp Ile Ala Gly Glu His Thr
130                 135                 140

Ser Phe Asp Lys Leu Pro Lys Asp Val Met Ala Thr Tyr Arg Gly Thr
145                 150                 155                 160

Ala Phe Gly Ser Asp Asp Ala Gly Lys Leu Thr Tyr Thr Ile Asp
                165                 170                 175

Phe Ala Ala Lys Gln Gly His Gly Lys Ile Glu His Leu Lys Ser Pro
            180                 185                 190

Glu Leu Asn Val Asp Leu Ala Val Ala Tyr Ile Lys Pro Asp Glu Lys
        195                 200                 205

His His Ala Val Ile Ser Gly Ser Val Leu Tyr Asn Gln Asp Glu Lys
    210                 215                 220

Gly Ser Tyr Arg Leu Gly Ile Phe Gly Glu Lys Ala Gln Glu Val Ala
225                 230                 235                 240

Gly Ser Ala Glu Val Glu Thr Ala Asn Gly Ile His His Ile Gly Leu
                245                 250                 255

Ala Ala Lys Gln
            260
```

<210> SEQ ID NO 18
<211> LENGTH: 260
<212> TYPE: PRT
<213> ORGANISM: Artificial sequence
<220> FEATURE:
<223> OTHER INFORMATION: Synthetic polypeptide

<400> SEQUENCE: 18

```
Cys Ser Ser Gly Gly Gly Ser Gly Gly Gly Gly Val Thr Ala Asp
1               5                   10                  15

Ile Gly Thr Gly Leu Ala Asp Ala Leu Thr Ala Pro Leu Asp His Lys
            20                  25                  30
```

Asp Lys Gly Leu Lys Ser Leu Thr Leu Glu Asp Ser Ile Ser Gln Asn
            35                  40                  45

Gly Thr Leu Thr Leu Ser Ala Gln Gly Ala Glu Lys Thr Tyr Gly Asn
 50                  55                  60

Gly Asp Ser Leu Asn Thr Gly Lys Leu Lys Asn Asp Lys Val Ser Arg
 65                  70                  75                  80

Phe Asp Phe Ile Arg Gln Ile Glu Val Asp Gly Gln Leu Ile Thr Leu
                 85                  90                  95

Glu Ser Gly Glu Phe Gln Val Tyr Lys Gln Ser His Ser Ala Leu Thr
            100                 105                 110

Ala Leu Gln Thr Glu Gln Glu Gln Asp Pro Glu His Ser Glu Lys Met
            115                 120                 125

Val Ala Lys Arg Arg Phe Arg Ile Gly Asp Ile Ala Gly Glu His Thr
130                 135                 140

Ser Phe Asp Lys Leu Pro Lys Asp Val Met Ala Thr Tyr Arg Gly Thr
145                 150                 155                 160

Ala Phe Gly Ser Asp Asp Ala Gly Gly Lys Leu Thr Tyr Thr Ile Asp
                165                 170                 175

Phe Ala Ala Lys Gln Gly His Gly Lys Ile Glu His Leu Lys Ser Pro
                180                 185                 190

Glu Leu Asn Val Asp Leu Ala Val Ala Tyr Ile Lys Pro Asp Glu Lys
            195                 200                 205

His His Ala Val Ile Ser Gly Ser Val Leu Tyr Asn Gln Asp Glu Lys
            210                 215                 220

Gly Ser Tyr Ser Leu Gly Ile Phe Gly Glu Lys Ala Gln Glu Val Ala
225                 230                 235                 240

Gly Ser Ala Glu Val Glu Thr Ala Asn Gly Ile His Leu Ile Gly Leu
                245                 250                 255

Ala Ala Lys Gln
            260

<210> SEQ ID NO 19
<211> LENGTH: 255
<212> TYPE: PRT
<213> ORGANISM: Artificial sequence
<220> FEATURE:
<223> OTHER INFORMATION: Synthetic polypeptide

<400> SEQUENCE: 19

Cys Ser Ser Gly Gly Gly Val Ala Ala Asp Ile Gly Ala Gly Leu
1               5                   10                  15

Ala Asp Ala Leu Thr Ala Pro Leu Asp His Lys Asp Lys Gly Leu Gln
            20                  25                  30

Ser Leu Thr Leu Asp Gln Ser Val Ser Lys Asn Glu Lys Leu Lys Leu
            35                  40                  45

Ala Ala Gln Gly Ala Glu Lys Thr Tyr Gly Asn Gly Asp Ser Leu Asn
 50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Val Tyr Lys Gln Ser His Ser Ala Leu Thr Ala Phe Gln Thr Glu
            100                 105                 110

Gln Ile Gln Asp Ser Glu His Ser Gly Lys Met Val Ala Lys Arg Gln
            115                 120                 125

Phe Arg Ile Gly Asp Ile Ala Gly Glu His Thr Ser Phe Asp Lys Leu
    130                 135                 140

Pro Glu Gly Gly Arg Ala Thr Tyr Arg Gly Thr Ala Phe Gly Ser Asp
145                 150                 155                 160

Asp Ala Gly Gly Lys Leu Thr Tyr Thr Ile Asp Phe Ala Ala Lys Gln
                165                 170                 175

Gly Asn Gly Lys Ile Glu His Leu Lys Ser Pro Glu Leu Asn Val Asp
                180                 185                 190

Leu Ala Ala Ala Asp Ile Lys Pro Asp Gly Lys Arg His Ala Val Ile
            195                 200                 205

Ser Gly Ser Val Leu Tyr Asn Gln Ala Glu Lys Gly Ser Tyr Arg Leu
    210                 215                 220

Gly Ile Phe Gly Gly Lys Ala Gln Glu Val Ala Gly Ser Ala Glu Val
225                 230                 235                 240

Lys Thr Val Asn Gly Ile Arg His Ile Gly Leu Ala Ala Lys Gln
                245                 250                 255

<210> SEQ ID NO 20
<211> LENGTH: 255
<212> TYPE: PRT
<213> ORGANISM: Artificial sequence
<220> FEATURE:
<223> OTHER INFORMATION: Synthetic polypeptide

<400> SEQUENCE: 20

Cys Ser Ser Gly Gly Gly Val Ala Ala Asp Ile Gly Ala Gly Leu
1               5                   10                  15

Ala Asp Ala Leu Thr Ala Pro Leu Asp His Lys Asp Lys Gly Leu Gln
                20                  25                  30

Ser Leu Thr Leu Asp Gln Ser Val Ser Lys Asn Glu Lys Leu Lys Leu
            35                  40                  45

Ala Ala Gln Gly Ala Glu Lys Thr Tyr Gly Asn Gly Asp Ser Leu Asn
        50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Val Tyr Lys Gln Ser His Ser Ala Leu Thr Ala Phe Gln Thr Glu
                100                 105                 110

Gln Ile Gln Asp Ser Glu His Ser Gly Lys Met Val Ala Lys Arg Gln
            115                 120                 125

Phe Arg Ile Gly Asp Ile Ala Gly Glu His Thr Ser Phe Asp Lys Leu
    130                 135                 140

Pro Glu Gly Gly Arg Ala Thr Tyr Arg Gly Thr Ala Phe Gly Ser Asp
145                 150                 155                 160

Asp Ala Gly Gly Lys Leu Thr Tyr Thr Ile Asp Phe Ala Ala Lys Gln
                165                 170                 175

Gly Asn Gly Lys Ile Glu His Leu Lys Ser Pro Glu Leu Asn Val Asp
                180                 185                 190

Leu Ala Ala Ala Asp Ile Lys Pro Asp Gly Lys Arg His Ala Val Ile
            195                 200                 205

Ser Gly Ser Val Leu Tyr Asn Gln Ala Glu Lys Gly Ser Tyr Ser Leu
    210                 215                 220

Gly Ile Phe Gly Gly Lys Ala Gln Glu Val Ala Gly Ser Ala Glu Val
225                 230                 235                 240

```
Lys Thr Val Asn Gly Ile Arg Leu Ile Gly Leu Ala Ala Lys Gln
            245                 250                 255

<210> SEQ ID NO 21
<211> LENGTH: 255
<212> TYPE: PRT
<213> ORGANISM: Artificial sequence
<220> FEATURE:
<223> OTHER INFORMATION: Synthetic polypeptide

<400> SEQUENCE: 21

Cys Ser Ser Gly Gly Gly Val Ala Ala Asp Ile Gly Ala Gly Leu
1               5                   10                  15

Ala Asp Ala Leu Thr Ala Pro Leu Asp His Lys Asp Lys Gly Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Val Tyr Lys Gln Ser His Ser Ala Leu Thr Ala Phe Gln Thr Glu
            100                 105                 110

Gln Ile Gln Asp Ser Glu His Ser Gly Lys Met Val Ala Lys Arg Gln
        115                 120                 125

Phe Arg Ile Gly Asp Ile Ala Gly Glu His Thr Ser Phe Asp Lys Leu
    130                 135                 140

Pro Glu Gly Gly Arg Ala Thr Tyr Arg Gly Thr Ala Phe Gly Ser Asp
145                 150                 155                 160

Asp Ala Gly Gly Lys Leu Thr Tyr Thr Ile Asp Phe Ala Ala Lys Gln
                165                 170                 175

Gly Asn Gly Lys Ile Glu His Leu Lys Ser Pro Glu Leu Asn Val Asp
            180                 185                 190

Leu Ala Ala Ala Asp Ile Lys Pro Asp Gly Lys Arg His Ala Val Ile
        195                 200                 205

Ser Gly Ser Val Leu Tyr Asn Gln Ala Glu Lys Gly Ser Tyr Arg Leu
    210                 215                 220

Gly Ile Phe Gly Gly Lys Ala Gln Glu Val Ala Gly Ser Ala Glu Val
225                 230                 235                 240

Lys Thr Val Asn Gly Ile Arg Leu Ile Gly Leu Ala Ala Lys Gln
                245                 250                 255

<210> SEQ ID NO 22
<211> LENGTH: 254
<212> TYPE: PRT
<213> ORGANISM: Artificial sequence
<220> FEATURE:
<223> OTHER INFORMATION: Synthetic polypeptide

<400> SEQUENCE: 22

Cys Ser Ser Gly Gly Gly Val Ala Ala Asp Ile Gly Ala Gly Leu
1               5                   10                  15

Ala Asp Ala Leu Thr Ala Pro Leu Asp His Lys Asp Lys Ser Leu Gln
            20                  25                  30

Ser Leu Thr Leu Asp Gln Ser Val Arg Lys Asn Glu Lys Leu Lys Leu
        35                  40                  45
```

Ala Ala Gln Gly Ala Glu Lys Thr Tyr Gly Asn Gly Asp Ser Leu Asn
            50                  55                  60

Thr Gly Lys Leu Lys Asn Asp Lys Val Ser Arg Phe Asp Phe Ile Arg
 65                  70                  75                  80

Gln Ile Glu Val Asp Gly Gln Leu Ile Thr Leu Glu Ser Gly Glu Phe
                85                  90                  95

Gln Ile Tyr Lys Gln Asp His Ser Ala Val Val Ala Leu Gln Ile Glu
            100                 105                 110

Lys Ile Asn Asn Pro Asp Lys Ile Asp Ser Leu Ile Asn Gln Arg Ser
            115                 120                 125

Phe Arg Val Ser Asp Leu Gly Gly Glu His Thr Ala Phe Asn Gln Leu
            130                 135                 140

Pro Ser Gly Lys Ala Glu Tyr His Gly Lys Ala Phe Ser Ser Asp Asp
145                 150                 155                 160

Pro Asn Gly Arg Leu His Tyr Ser Ile Asp Phe Thr Lys Lys Gln Gly
            165                 170                 175

Tyr Gly Arg Ile Glu His Leu Lys Thr Pro Glu Gln Asn Val Glu Leu
            180                 185                 190

Ala Ser Ala Glu Leu Lys Ala Asp Glu Lys Ser His Ala Val Ile Leu
            195                 200                 205

Gly Asp Thr Arg Tyr Gly Gly Glu Lys Gly Thr Tyr His Leu Ala
210                 215                 220

Leu Phe Gly Asp Arg Ala Gln Glu Ile Ala Gly Ser Ala Thr Val Lys
225                 230                 235                 240

Ile Arg Glu Lys Val His Glu Ile Gly Ile Ala Gly Lys Gln
            245                 250

<210> SEQ ID NO 23
<211> LENGTH: 254
<212> TYPE: PRT
<213> ORGANISM: Artificial sequence
<220> FEATURE:
<223> OTHER INFORMATION: Synthetic polypeptide

<400> SEQUENCE: 23

Cys Ser Ser Gly Gly Gly Val Ala Ala Asp Ile Gly Ala Gly Leu
 1               5                  10                  15

Ala Asp Ala Leu Thr Ala Pro Leu Asp His Lys Asp Lys Ser Leu Gln
            20                  25                  30

Ser Leu Thr Leu Asp Gln Ser Val Arg Lys Asn Glu Lys Leu Lys Leu
            35                  40                  45

Ala Ala Gln Gly Ala Glu Lys Thr Tyr Gly Asn Gly Asp Ser Leu Asn
            50                  55                  60

Thr Gly Lys Leu Lys Asn Asp Lys Val Ser Arg Phe Asp Phe Ile Arg
 65                  70                  75                  80

Gln Ile Glu Val Asp Gly Gln Leu Ile Thr Leu Glu Ser Gly Glu Phe
                85                  90                  95

Gln Ile Tyr Lys Gln Asp His Ser Ala Val Val Ala Leu Gln Ile Glu
            100                 105                 110

Lys Ile Asn Asn Pro Asp Lys Ile Asp Ser Leu Ile Asn Gln Arg Ser
            115                 120                 125

Phe Arg Val Ser Asp Leu Gly Gly Glu His Thr Ala Phe Asn Gln Leu
            130                 135                 140

Pro Ser Gly Lys Ala Glu Tyr His Gly Lys Ala Phe Ser Ser Asp Asp
145                 150                 155                 160

Pro Asn Gly Arg Leu His Tyr Ser Ile Asp Phe Thr Lys Lys Gln Gly
            165                 170                 175

Tyr Gly Arg Ile Glu His Leu Lys Thr Pro Glu Gln Asn Val Glu Leu
        180                 185                 190

Ala Ser Ala Glu Leu Lys Ala Asp Glu Lys Ser His Ala Val Ile Leu
        195                 200                 205

Gly Asp Thr Arg Tyr Gly Gly Glu Asn Gly Thr Tyr His Leu Ala
        210                 215                 220

Leu Phe Gly Asp Arg Ala Gln Glu Ile Ala Gly Ser Ala Thr Val Lys
225                 230                 235                 240

Ile Arg Glu Lys Val His Glu Ile Gly Ile Ala Gly Lys Gln
            245                 250

<210> SEQ ID NO 24
<211> LENGTH: 254
<212> TYPE: PRT
<213> ORGANISM: Artificial sequence
<220> FEATURE:
<223> OTHER INFORMATION: Synthetic polypeptide

<400> SEQUENCE: 24

Cys Ser Ser Gly Gly Gly Val Ala Ala Asp Ile Gly Ala Gly Leu
1               5                   10                  15

Ala Asp Ala Leu Thr Ala Pro Leu Asp His Lys Asp Lys Ser Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Ile Tyr Lys Gln Asp His Ser Ala Val Val Ala Leu Gln Ile Glu
            100                 105                 110

Lys Ile Asn Asn Pro Asp Lys Ile Asp Ser Leu Ile Asn Gln Arg Ser
        115                 120                 125

Phe Arg Val Ser Asp Leu Gly Gly Glu His Thr Ala Phe Asn Gln Leu
    130                 135                 140

Pro Ser Gly Lys Ala Glu Tyr His Gly Lys Ala Phe Ser Ser Asp Asp
145                 150                 155                 160

Pro Asn Gly Arg Leu His Tyr Ser Ile Asp Phe Thr Lys Lys Gln Gly
                165                 170                 175

Tyr Gly Arg Ile Glu His Leu Lys Thr Pro Glu Gln Asn Val Glu Leu
            180                 185                 190

Ala Ser Ala Glu Leu Lys Ala Asp Glu Lys Ser His Ala Val Ile Leu
        195                 200                 205

Gly Asp Thr Arg Tyr Gly Gly Glu Lys Ser Thr Tyr His Leu Ala
        210                 215                 220

Leu Phe Gly Asp Arg Ala Gln Glu Ile Ala Gly Ser Ala Thr Val Lys
225                 230                 235                 240

Ile Arg Glu Lys Val His Glu Ile Gly Ile Ala Gly Lys Gln
            245                 250

<210> SEQ ID NO 25

```
<211> LENGTH: 174
<212> TYPE: PRT
<213> ORGANISM: Neisseria meningitidis

<400> SEQUENCE: 25

Met Lys Lys Ala Leu Ala Thr Leu Ile Ala Leu Ala Leu Pro Ala Ala
1               5                   10                  15

Ala Leu Ala Glu Gly Ala Ser Gly Phe Tyr Val Gln Ala Asp Ala Ala
            20                  25                  30

His Ala Lys Ala Ser Ser Ser Leu Gly Ser Ala Lys Gly Phe Ser Pro
        35                  40                  45

Arg Ile Ser Ala Gly Tyr Arg Ile Asn Asp Leu Arg Phe Ala Val Asp
    50                  55                  60

Tyr Thr Arg Tyr Lys Asn Tyr Lys Ala Pro Ser Thr Asp Phe Lys Leu
65                  70                  75                  80

Tyr Ser Ile Gly Ala Ser Ala Ile Tyr Asp Phe Asp Thr Gln Ser Pro
                85                  90                  95

Val Lys Pro Tyr Leu Gly Ala Arg Leu Ser Leu Asn Arg Ala Ser Val
            100                 105                 110

Asp Leu Gly Gly Ser Asp Ser Phe Ser Gln Thr Ser Ile Gly Leu Gly
        115                 120                 125

Val Leu Thr Gly Val Ser Tyr Ala Val Thr Pro Asn Val Asp Leu Asp
    130                 135                 140

Ala Gly Tyr Arg Tyr Asn Tyr Ile Gly Lys Val Asn Thr Val Lys Asn
145                 150                 155                 160

Val Arg Ser Gly Glu Leu Ser Val Gly Val Arg Val Lys Phe
                165                 170

<210> SEQ ID NO 26
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 26

Tyr Pro Tyr Asp Val Pro Asp Tyr Ala
1               5

<210> SEQ ID NO 27
<211> LENGTH: 8
<212> TYPE: PRT
<213> ORGANISM: Artificial sequence
<220> FEATURE:
<223> OTHER INFORMATION: Synthetic polypeptide

<400> SEQUENCE: 27

Asp Tyr Lys Asp Asp Asp Asp Lys
1               5

<210> SEQ ID NO 28
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 28

Glu Gln Lys Leu Ile Ser Glu Glu Asp Leu
1               5                   10
```

UNITED STATES PATENT AND TRADEMARK OFFICE
CERTIFICATE OF CORRECTION

| | | |
|---|---|---|
| PATENT NO. | : 11,834,476 B2 | Page 1 of 1 |
| APPLICATION NO. | : 17/065386 | |
| DATED | : December 5, 2023 | |
| INVENTOR(S) | : Peter T. Beernink et al. | |

It is certified that error appears in the above-identified patent and that said Letters Patent is hereby corrected as shown below:

In the Specification

In Column 1, Lines 19-22, please replace the STATEMENT OF GOVERNMENT SUPPORT section with the following:
-- This invention was made with government support under grant R01 AI099125 awarded by the National Institutes of Health. The government has certain rights in this invention. --

Signed and Sealed this
Eleventh Day of June, 2024

Katherine Kelly Vidal
*Director of the United States Patent and Trademark Office*